US010960186B2

(12) United States Patent
Harding et al.

(10) Patent No.: US 10,960,186 B2
(45) Date of Patent: Mar. 30, 2021

(54) MULTI-USE BLOOD CONTROL SAFETY CATHETER ASSEMBLY

(71) Applicant: Becton, Dickinson and Company, Franklin Lakes, NJ (US)

(72) Inventors: Weston Harding, Lehi, UT (US); Siddarth Shevgoor, Laguna Beach, CA (US); Lawrence Trainer, Murray, UT (US); Yiping Ma, Layton, UT (US); Sivaramakrishnan Balasubramanian, Morrisville, NC (US); Patrick Downie, Apex, NC (US); Jon Burkholz, Salt Lake City, UT (US); Shawn Isaacson, Layton, UT (US); Jeff O'Bryan, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 507 days.

(21) Appl. No.: 15/567,056

(22) PCT Filed: Apr. 15, 2016

(86) PCT No.: PCT/US2016/027955
§ 371 (c)(1),
(2) Date: Oct. 16, 2017

(87) PCT Pub. No.: WO2016/168745
PCT Pub. Date: Oct. 20, 2016

(65) Prior Publication Data
US 2018/0093077 A1 Apr. 5, 2018

Related U.S. Application Data

(63) Continuation-in-part of application No. PCT/US2015/026536, filed on Apr. 17, 2015, and a
(Continued)

(51) Int. Cl.
*A61M 25/06* (2006.01)
*A61M 25/00* (2006.01)
(Continued)

(52) U.S. Cl.
CPC ........ *A61M 25/0618* (2013.01); *A61M 5/158* (2013.01); *A61M 5/3202* (2013.01);
(Continued)

(58) Field of Classification Search
CPC ............ A61M 2039/266; A61M 39/06; A61M 39/24; A61M 39/26; A61M 2039/062; A61M 25/0618; A61M 5/158
See application file for complete search history.

(56) References Cited

U.S. PATENT DOCUMENTS 3,585,996 A    6/1971  Reynolds et al.
4,332,249 A    6/1982  Joslin
(Continued)

FOREIGN PATENT DOCUMENTS

AU    2006203664 A1    2/2008
CN       1871043 A     11/2006
(Continued)

OTHER PUBLICATIONS

US 5,755,409 A, 08/1979, Sigmund (withdrawn)
(Continued)

*Primary Examiner* — Nathan R Price
*Assistant Examiner* — Melissa A Snyder
(74) *Attorney, Agent, or Firm* — Dickinson Wright PLLC

(57) ABSTRACT

A valve actuator that moves in a catheter assembly between a first position where a valve is closed and a second position where the valve is open, the valve actuator including a shaft portion at a distal end of the valve actuator that is configured to pierce the valve, a mating portion at a proximal end of the valve actuator that is configured to engage a Luer device, a
(Continued)

diameter reduction region that connects the shaft portion and the mating portion, and a plurality of windows that extend through the valve actuator for flushing fluid, the plurality of windows being disposed in the diameter reduction region, wherein each of the plurality of windows does not extend a full length of the diameter reduction region.

19 Claims, 55 Drawing Sheets

Related U.S. Application Data continuation-in-part of application No. PCT/US2015/026542, filed on Apr. 17, 2015, and a continuation-in-part of application No. PCT/US2015/026534, filed on Apr. 17, 2015.

(51) Int. Cl.
*A61M 39/24* (2006.01)
*A61M 5/32* (2006.01)
*A61M 5/158* (2006.01)
*A61M 5/34* (2006.01)
*A61M 39/06* (2006.01)
*A61M 39/22* (2006.01)

(52) U.S. Cl.
CPC ........ *A61M 5/3213* (2013.01); *A61M 5/3232* (2013.01); *A61M 5/34* (2013.01); *A61M 25/0097* (2013.01); *A61M 25/0606* (2013.01); *A61M 25/0631* (2013.01); *A61M 39/24* (2013.01); *A61M 5/3273* (2013.01); *A61M 2039/064* (2013.01); *A61M 2039/066* (2013.01); *A61M 2039/0673* (2013.01); *A61M 2039/226* (2013.01)

(56) References Cited

U.S. PATENT DOCUMENTS

| | | | |
|---|---|---|---|
| 4,387,879 A | 6/1983 | Tauschinski | |
| 4,524,805 A | 6/1985 | Hoffman | |
| 4,622,964 A | 11/1986 | Flynn | |
| 4,762,516 A | 8/1988 | Luther et al. | |
| 4,809,679 A | 3/1989 | Shimonaka et al. | |
| 4,842,591 A | 6/1989 | Luther | |
| 4,850,961 A | 7/1989 | Wanderer et al. | |
| 4,917,668 A | 4/1990 | Haindl | |
| 4,946,133 A | 8/1990 | Johnson et al. | |
| 4,948,092 A | 8/1990 | Kasper et al. | |
| 4,978,344 A | 12/1990 | Dombrowski et al. | |
| 5,000,740 A | 3/1991 | Ducharme et al. | |
| 5,032,116 A | 7/1991 | Peterson et al. | |
| 5,053,014 A | 10/1991 | Van Heugten | |
| 5,092,845 A | 3/1992 | Chang | |
| 5,215,528 A | 6/1993 | Purdy et al. | |
| 5,228,453 A | 7/1993 | Sepetka | |
| 5,290,246 A | 3/1994 | Yamamoto et al. | |
| 5,328,482 A | 7/1994 | Sircom et al. | |
| 5,348,544 A | 9/1994 | Sweeney et al. | |
| 5,391,152 A | 2/1995 | Patterson | |
| 5,405,323 A | 4/1995 | Rogers et al. | |
| 5,419,766 A | 5/1995 | Chang et al. | |
| 5,423,766 A | 6/1995 | Di Cesare | |
| 5,458,658 A | 10/1995 | Sircom | |
| 5,501,675 A | 3/1996 | Erskine | |
| 5,538,508 A | 7/1996 | Steyn | |
| 5,558,651 A | 9/1996 | Crawford et al. | |
| 5,575,777 A | 11/1996 | Cover et al. | |
| 5,584,809 A | 12/1996 | Gaba | |
| 5,596,996 A | 1/1997 | Johanson | |
| 5,697,907 A | 12/1997 | Gaba | |
| 5,718,688 A | 2/1998 | Wozencroft | |
| 5,772,636 A | 6/1998 | Brimhall et al. | |
| 5,817,069 A | 10/1998 | Arnett | |
| 5,851,196 A | 12/1998 | Arnett | |
| 5,858,002 A | 1/1999 | Jesch | |
| 5,911,710 A | 6/1999 | Barry et al. | |
| 5,954,698 A | 9/1999 | Pike | |
| 5,967,490 A * | 10/1999 | Pike | A61M 39/26 251/149.1 |
| 6,001,080 A | 12/1999 | Kuracina et al. | |
| 6,042,876 A | 3/2000 | Deem | |
| 6,117,108 A | 9/2000 | Woehr et al. | |
| 6,213,978 B1 | 4/2001 | Voyten | |
| 6,221,047 B1 | 4/2001 | Greene et al. | |
| 6,224,569 B1 | 5/2001 | Brimhall et al. | |
| 6,379,333 B1 | 4/2002 | Brimhall et al. | |
| 6,425,884 B1 | 7/2002 | Wemmert et al. | |
| 6,506,181 B2 | 1/2003 | Meng et al. | |
| 6,595,981 B2 | 7/2003 | Huet | |
| 6,616,630 B1 | 9/2003 | Woehr et al. | |
| 6,652,486 B2 | 11/2003 | Bialecki et al. | |
| 6,709,419 B2 | 3/2004 | Woehr | |
| 6,972,002 B2 | 12/2005 | Thorne | |
| RE38,996 E | 2/2006 | Crawford et al. | |
| 7,008,404 B2 | 3/2006 | Nakajima | |
| 7,029,492 B1 | 4/2006 | Mitsudou et al. | |
| 7,226,434 B2 | 6/2007 | Carlyon et al. | |
| 7,267,661 B2 | 9/2007 | Susi | |
| 7,597,681 B2 | 10/2009 | Sutton et al. | |
| 7,651,476 B2 | 1/2010 | Kohler | |
| 7,682,340 B2 | 3/2010 | Funamura et al. | |
| 7,736,332 B2 | 6/2010 | Carlyon et al. | |
| 7,736,339 B2 | 6/2010 | Woehr et al. | |
| 7,988,664 B2 | 8/2011 | Fiser et al. | |
| 7,998,134 B2 * | 8/2011 | Fangrow | A61M 39/1011 604/535 |
| 8,308,691 B2 | 11/2012 | Woehr et al. | |
| 8,328,762 B2 | 12/2012 | Woehr et al. | |
| 8,333,735 B2 | 12/2012 | Woehr et al. | |
| 8,337,463 B2 | 12/2012 | Woehr et al. | |
| 8,348,893 B2 | 1/2013 | Carlyon | |
| 8,357,119 B2 | 1/2013 | Stout et al. | |
| 8,361,020 B2 | 1/2013 | Stout | |
| 8,361,038 B2 | 1/2013 | McKinnon et al. | |
| 8,382,718 B2 | 2/2013 | Woehr | |
| 8,388,583 B2 | 3/2013 | Stout et al. | |
| 8,419,688 B2 | 4/2013 | Woehr et al. | |
| 8,460,247 B2 | 6/2013 | Woehr et al. | |
| 8,469,928 B2 | 6/2013 | Stout et al. | |
| 8,496,623 B2 | 7/2013 | Burkholz | |
| 8,540,728 B2 | 9/2013 | Woehr et al. | |
| 8,591,468 B2 | 11/2013 | Woehr et al. | |
| 8,597,249 B2 | 12/2013 | Woehr et al. | |
| 8,679,063 B2 | 3/2014 | Stout et al. | |
| 8,740,859 B2 | 6/2014 | McKinnon et al. | |
| 8,764,711 B2 | 7/2014 | Kuracina et al. | |
| 8,926,564 B2 | 1/2015 | King et al. | |
| 8,939,938 B2 | 1/2015 | Funamura et al. | |
| 8,951,230 B2 | 2/2015 | Tanabe et al. | |
| 9,089,671 B2 | 7/2015 | Stout et al. | |
| 9,114,241 B2 | 8/2015 | Stout et al. | |
| 9,149,625 B2 | 10/2015 | Woehr et al. | |
| 9,149,626 B2 | 10/2015 | Woehr et al. | |
| 8,932,259 B2 | 11/2015 | Stout et al. | |
| 9,358,364 B2 | 6/2016 | Isaacson et al. | |
| 9,370,641 B2 | 6/2016 | Woehr et al. | |
| 9,408,632 B2 | 8/2016 | Erskine | |
| 9,592,152 B2 | 3/2017 | Griffis et al. | |
| 9,717,886 B2 | 8/2017 | Kuehn et al. | |
| 2001/0053895 A1 | 12/2001 | Vaillancourt | |
| 2002/0128604 A1 | 9/2002 | Nakajima | |
| 2002/0169418 A1 | 11/2002 | Menzi et al. | |
| 2003/0195471 A1 | 10/2003 | Woehr et al. | |
| 2004/0116856 A1 | 6/2004 | Woehr et al. | |
| 2004/0204689 A1 | 10/2004 | Lynn | |
| 2004/0225260 A1 | 11/2004 | Villa et al. | |
| 2005/0010176 A1 | 1/2005 | Dikeman et al. | |
| 2005/0043684 A1 | 2/2005 | Basta et al. | |
| 2005/0075609 A1 | 4/2005 | Latona | |
| 2005/0113755 A1 | 5/2005 | Greene et al. | |

(56) References Cited

U.S. PATENT DOCUMENTS

| | | |
|---|---|---|
| 2006/0074384 A1 | 4/2006 | Kohler |
| 2006/0155245 A1 | 7/2006 | Woehr |
| 2006/0178635 A1 | 8/2006 | Callaway |
| 2006/0200080 A1 | 9/2006 | Abulhaj |
| 2007/0038186 A1 | 2/2007 | Sutton et al. |
| 2007/0083162 A1 | 4/2007 | O'Reagan et al. |
| 2007/0129689 A1 | 6/2007 | Woehr et al. |
| 2007/0176414 A1 | 8/2007 | McBee et al. |
| 2007/0270754 A1 | 11/2007 | Soderholm et al. |
| 2008/0097343 A1 | 4/2008 | Woehr |
| 2008/0140011 A1 | 6/2008 | Hager et al. |
| 2008/0208132 A1 | 8/2008 | Funamura et al. |
| 2008/0243086 A1 | 10/2008 | Hager et al. |
| 2009/0163861 A1 | 6/2009 | Carlyon |
| 2009/0182280 A1 | 7/2009 | Glowacki et al. |
| 2009/0312711 A1 | 12/2009 | Brimhall |
| 2010/0137803 A1 | 6/2010 | Funamura et al. |
| 2010/0191189 A1 | 7/2010 | Harding et al. |
| 2010/0204648 A1 | 8/2010 | Stout et al. |
| 2010/0204660 A1 | 8/2010 | McKinnon et al. |
| 2010/0217208 A1 | 8/2010 | Snow |
| 2010/0222746 A1 | 9/2010 | Burkholz |
| 2011/0046570 A1* | 2/2011 | Stout ................ A61M 39/0693 604/246 |
| 2011/0054403 A1 | 3/2011 | Tanabe et al. |
| 2011/0160662 A1 | 6/2011 | Stout et al. |
| 2011/0288482 A1 | 11/2011 | Farrell et al. |
| 2011/0301551 A1 | 12/2011 | Koehler et al. |
| 2012/0065612 A1 | 3/2012 | Stout et al. |
| 2012/0078200 A1 | 3/2012 | Woehr et al. |
| 2012/0123354 A1 | 5/2012 | Woehr |
| 2012/0136311 A1 | 5/2012 | Knutsson et al. |
| 2012/0220957 A1 | 8/2012 | Kuracina et al. |
| 2012/0238966 A1 | 9/2012 | Kuracina et al. |
| 2012/0277679 A1 | 11/2012 | Steube |
| 2013/0030370 A1 | 1/2013 | Walker et al. |
| 2013/0090607 A1 | 4/2013 | McKinnon et al. |
| 2013/0090609 A1 | 4/2013 | Sonderegger et al. |
| 2013/0178807 A1 | 7/2013 | Baid |
| 2013/0184645 A1 | 7/2013 | Baid |
| 2013/0226141 A1 | 8/2013 | King et al. |
| 2013/0245567 A1 | 9/2013 | Tremblay |
| 2013/0253443 A1 | 9/2013 | Woehr et al. |
| 2013/0324930 A1 | 12/2013 | Fuchs et al. |
| 2014/0012203 A1 | 1/2014 | Woehr et al. |
| 2014/0018738 A1 | 1/2014 | Steube |
| 2014/0276434 A1 | 9/2014 | Woehr et al. |
| 2014/0364809 A1 | 12/2014 | Isaacson et al. |
| 2015/0151088 A1 | 6/2015 | Lim et al. |
| 2016/0114137 A1 | 4/2016 | Woehr et al. |
| 2017/0348518 A1 | 12/2017 | Ma et al. |

FOREIGN PATENT DOCUMENTS

| | | | |
|---|---|---|---|
| CN | 202682467 U | 1/2013 | |
| CN | 106470607 A | 3/2017 | |
| EP | 0352928 A1 | 1/1990 | |
| EP | 2228093 A1 | 9/2010 | |
| EP | 2343095 A1 | 7/2011 | |
| EP | 2489393 A1 | 8/2012 | |
| EP | 2566543 A1 | 3/2013 | |
| JP | H1057497A A | 3/1998 | |
| JP | 2001-514943 A | 9/2001 | |
| JP | 2002126080 A | 5/2002 | |
| JP | 2002263197 A | 9/2002 | |
| JP | 3786312 B2 | 3/2006 | |
| JP | 2008-173206 A | 7/2008 | |
| JP | 4518609 B2 | 5/2010 | |
| JP | 2010099534 A | 5/2010 | |
| JP | 2011-115630 A | 6/2011 | |
| JP | 3170612 | 9/2011 | |
| JP | 2012-517326 A | 8/2012 | |
| JP | 2013192868 A | 9/2013 | |
| JP | 2015160061 A | 9/2015 | |
| JP | 2015173972 A | 10/2015 | |
| SG | 173383 A1 | 8/2011 | |
| WO | WO-1993005840 A2 | 4/1993 | |
| WO | WO-1995022364 A1 | 8/1995 | |
| WO | 9924092 | 5/1999 | |
| WO | WO-2001012249 A1 | 2/2001 | |
| WO | 0193040 A2 | 12/2001 | |
| WO | 0195958 A1 | 12/2001 | |
| WO | WO-2003011381 A1 | 2/2003 | |
| WO | WO-2004004819 A1 | 1/2004 | |
| WO | WO-2005/042073 A1 | 5/2005 | |
| WO | 2008064332 A2 | 5/2008 | |
| WO | 2009154824 A1 | 12/2009 | |
| WO | WO-2012020633 A1 * | 2/2012 | ............ A61M 5/158 |
| WO | WO-2013/014639 A1 | 1/2013 | |
| WO | WO-2013/051242 A1 | 4/2013 | |
| WO | WO-2013052666 A1 | 4/2013 | |
| WO | WO-2013137348 A1 | 9/2013 | |
| WO | WO-2014/054166 A1 | 4/2014 | |
| WO | WO-2014126865 A1 | 8/2014 | |
| WO | 2015161296 A1 | 10/2015 | |

OTHER PUBLICATIONS

Singapore Office Action dated Jan. 29, 2020 in Singapore Patent Application No. 11201708370P.

Japanese Office Action dated Jan. 28, 2020 in Japanese Patent Application No. 2017-554341.

Singapore Office Action dated Nov. 12, 2019 in Singapore Patent Application No. 11201708371S.

Brazilian Office Action dated Feb. 4, 2020 in Brazilian Patent Application No. 112015030658-6.

Medikit Co.,Ltd., Dual Protection Safety I.V. Catheter—Supercath 5: A New Generation of Safety I.V. Catheter, Medikit, Manufacturer Togo Medikit Co., Ltd., IVBB080001-B61G2S, Approximately 2008 (3 Pages Total).

* cited by examiner

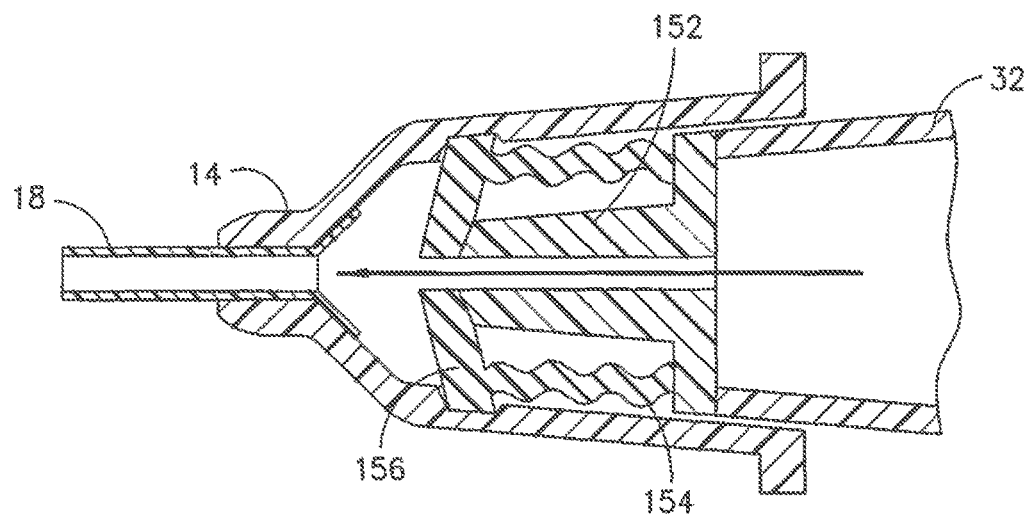
FIG.21A
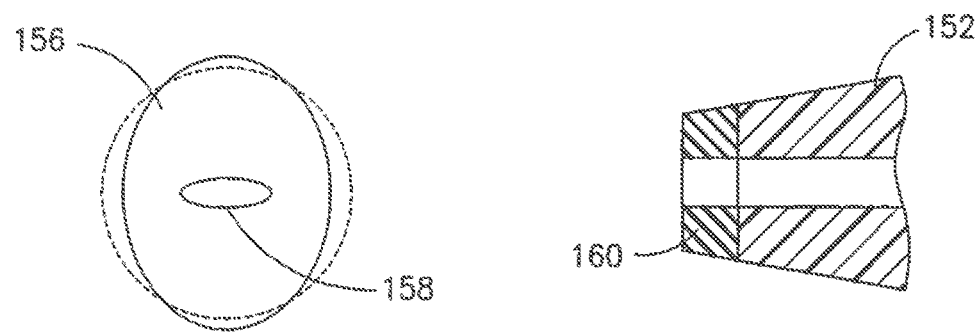
FIG.21B
FIG.21C

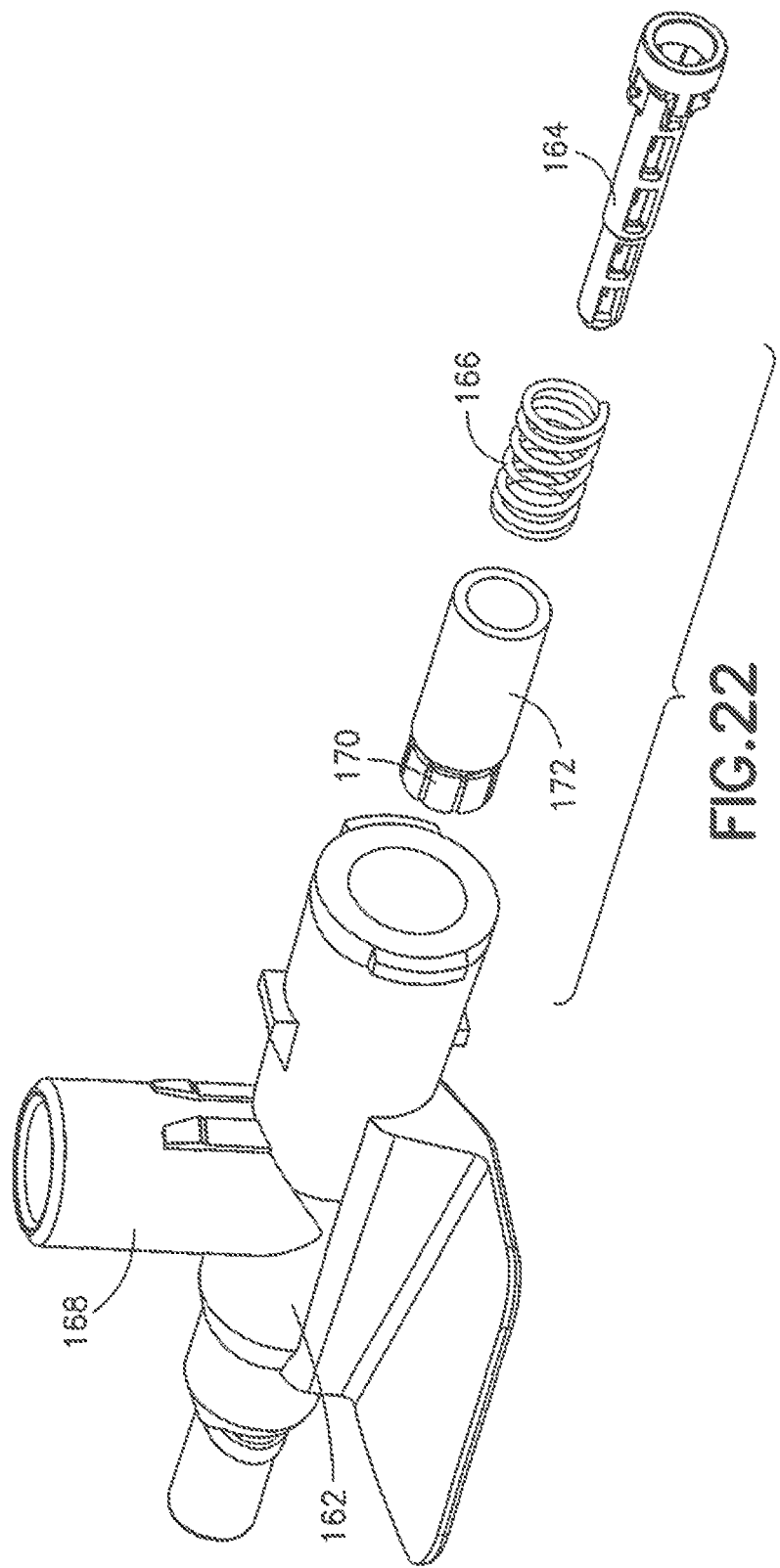

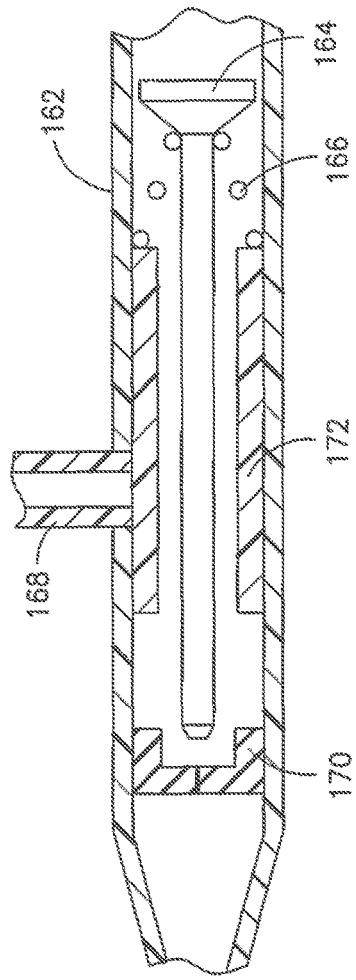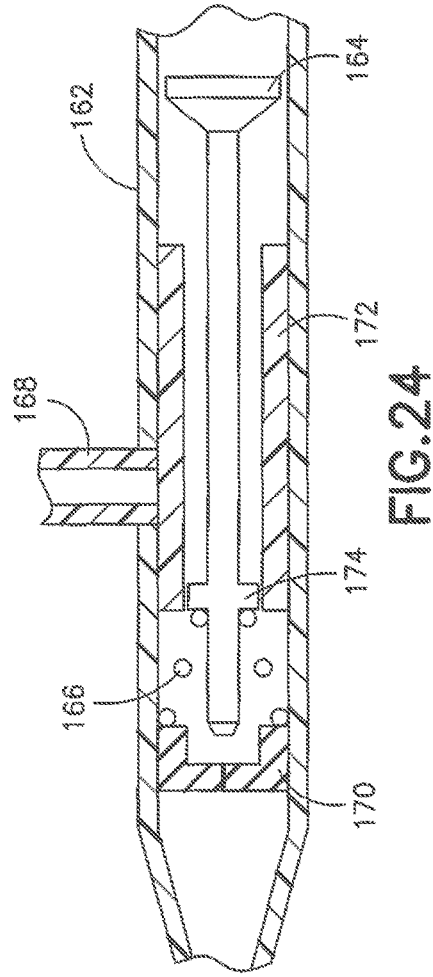

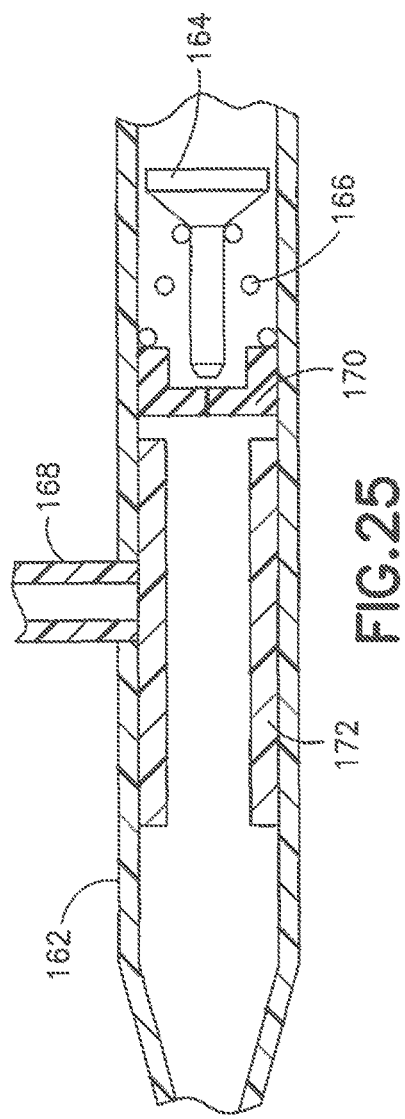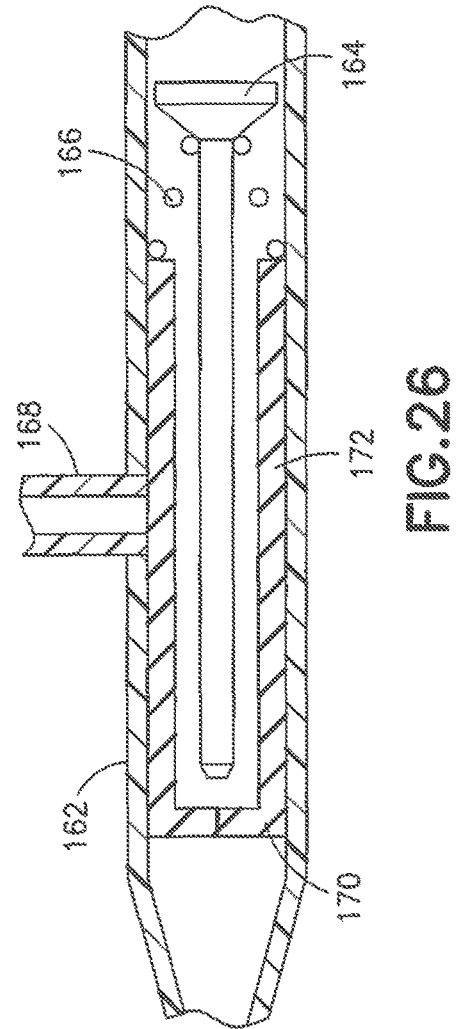

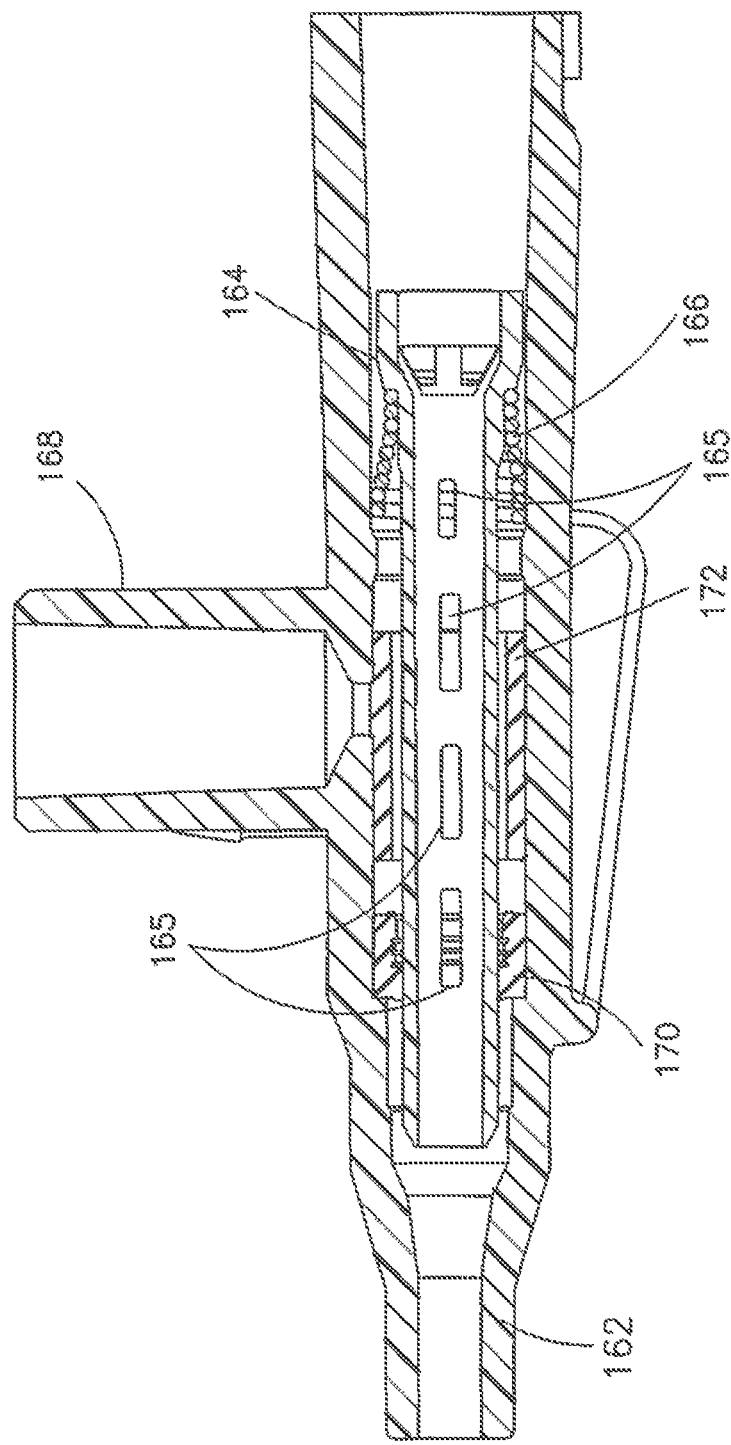

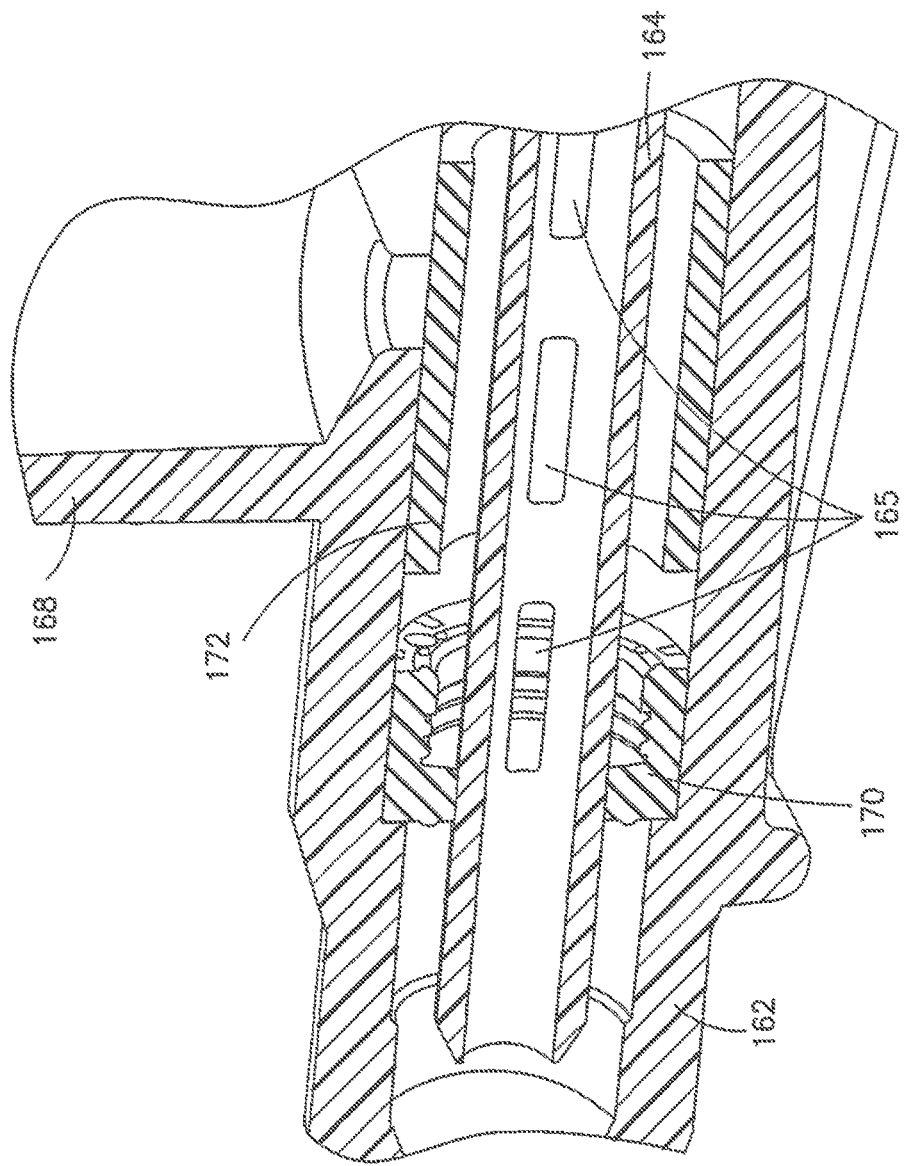

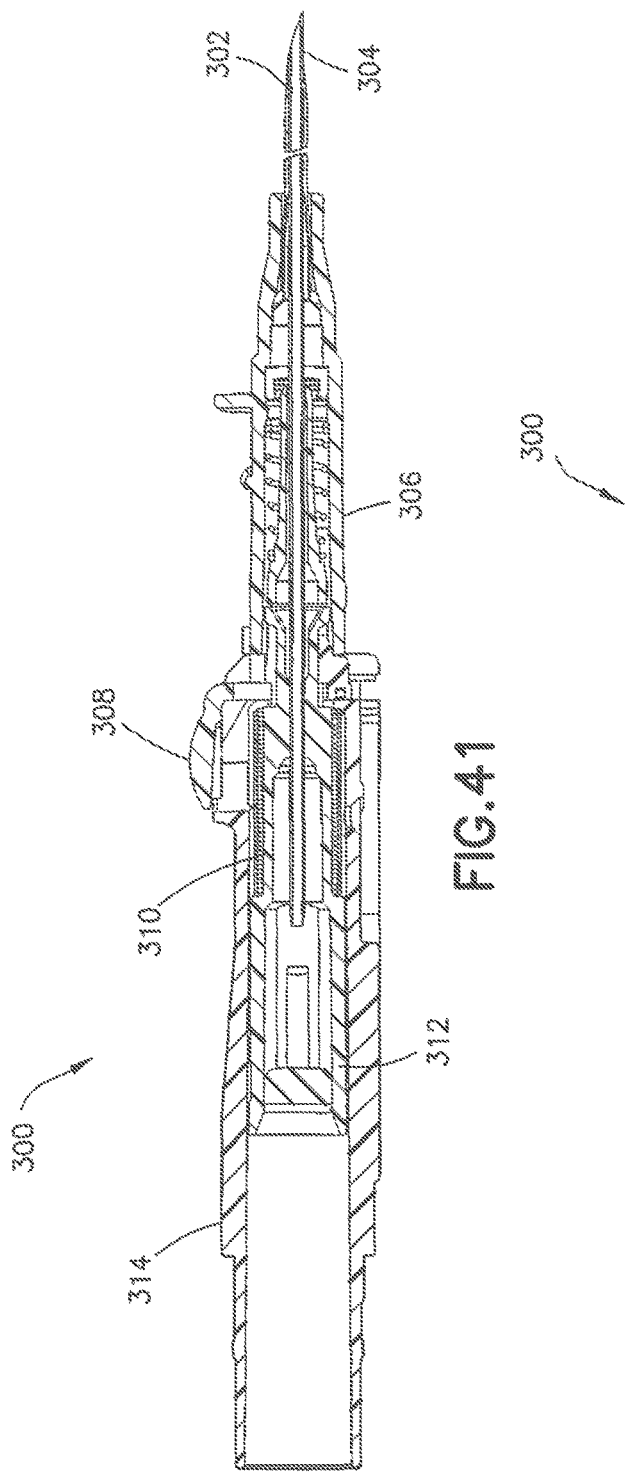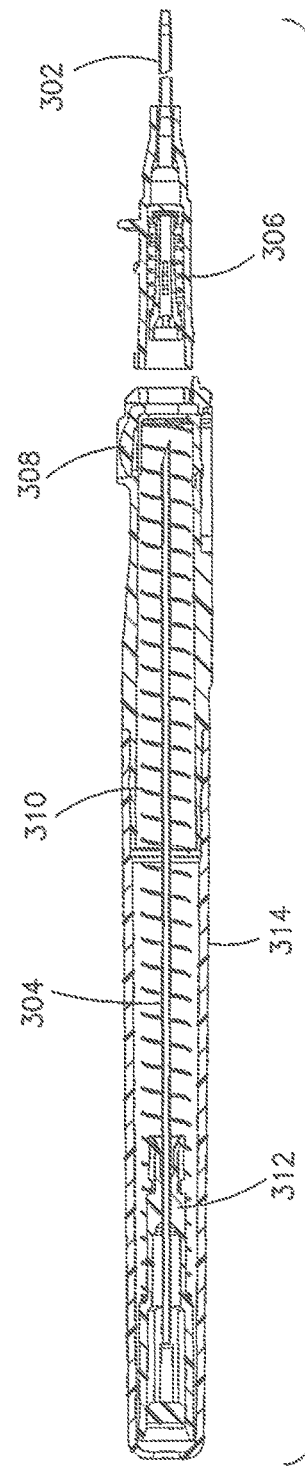
FIG. 41
FIG. 42

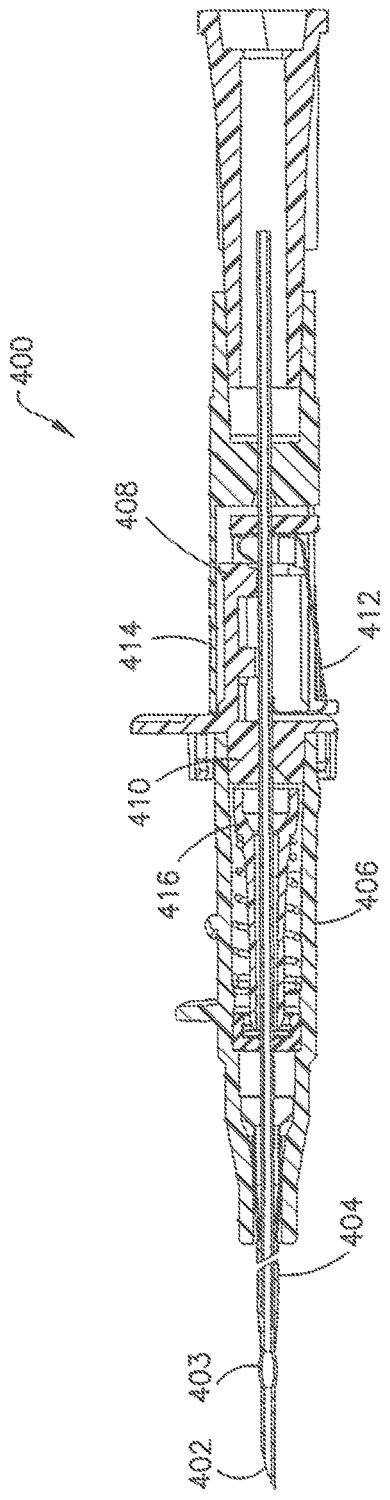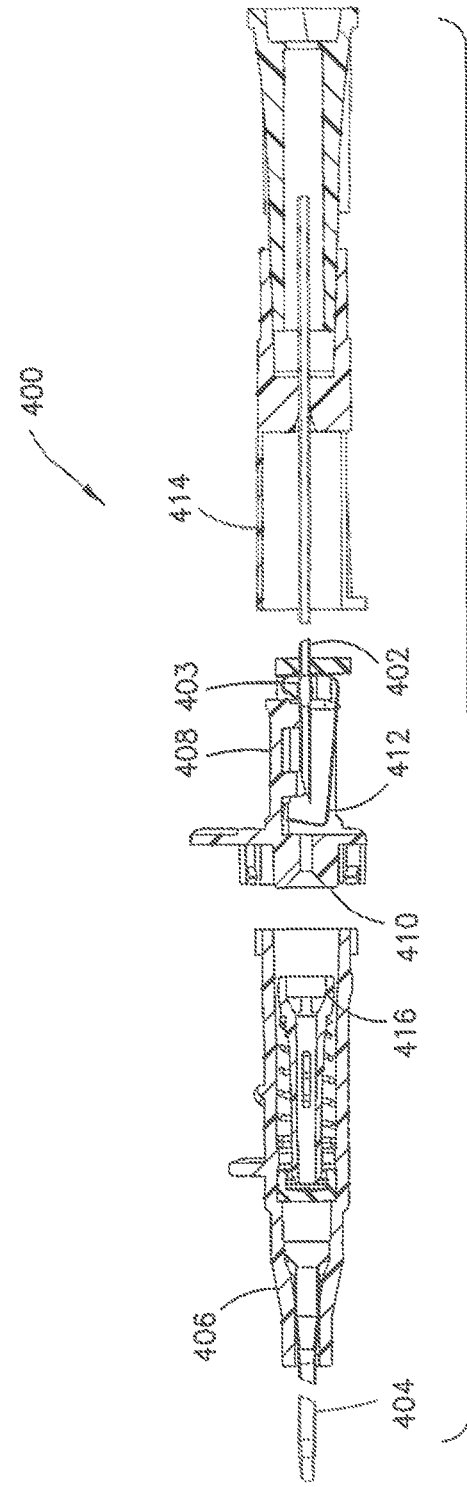

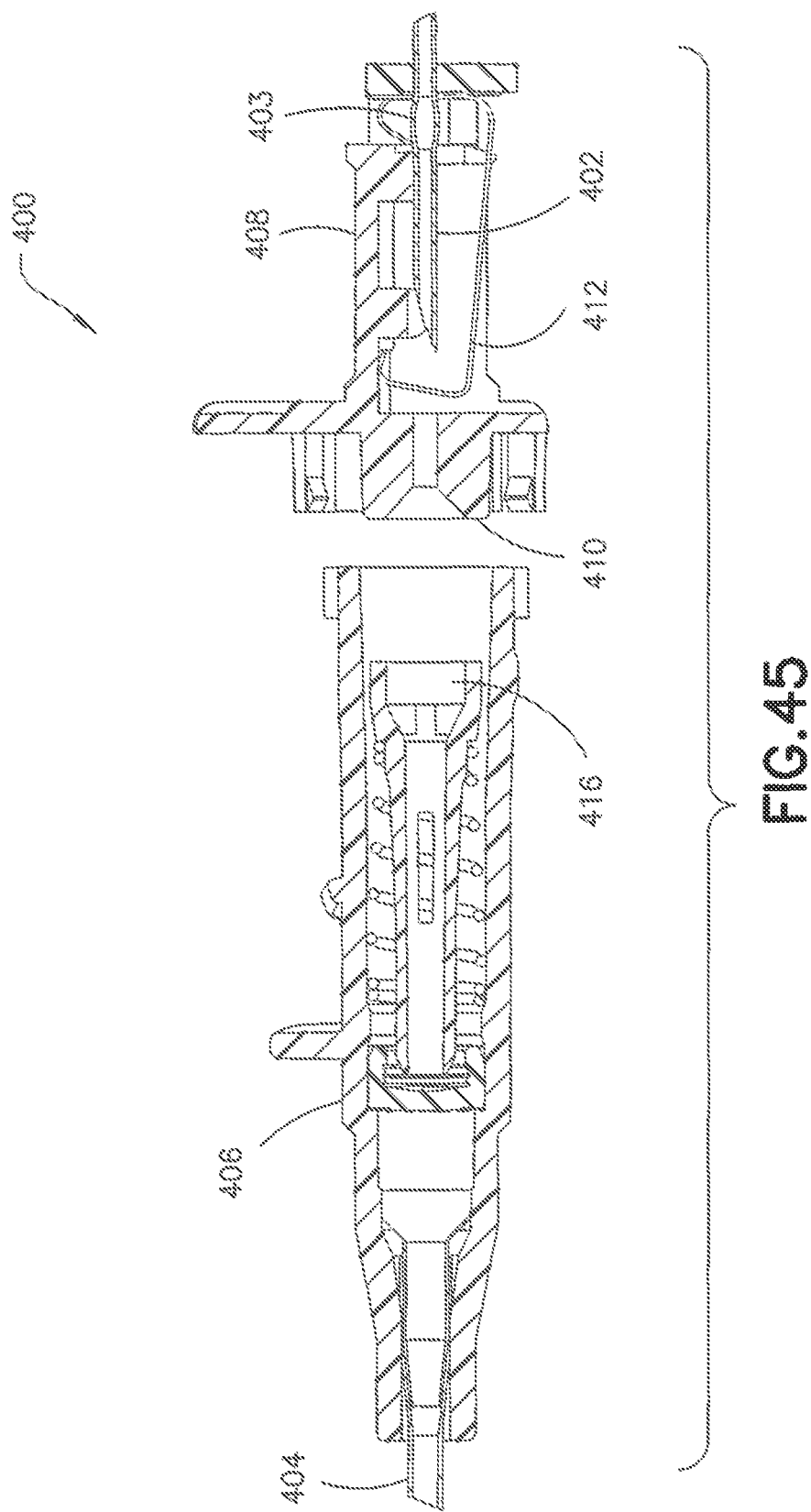

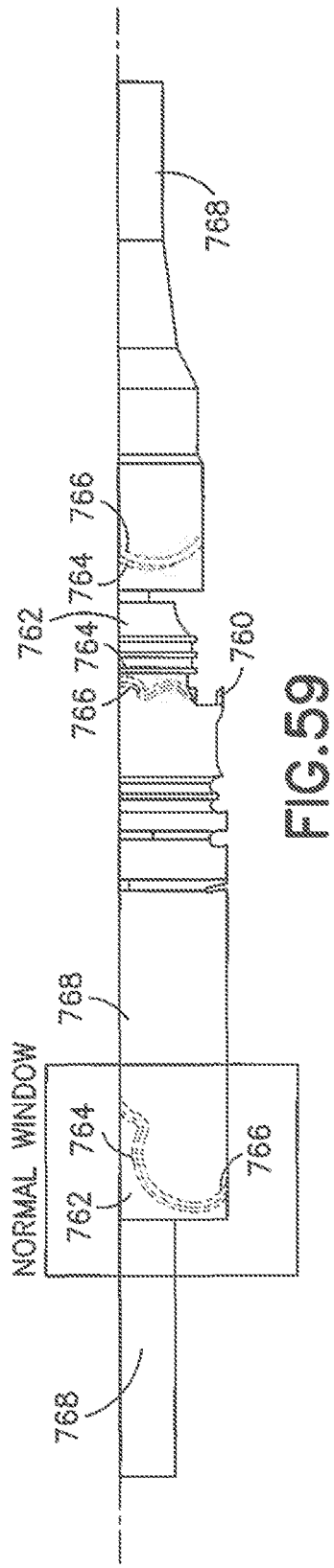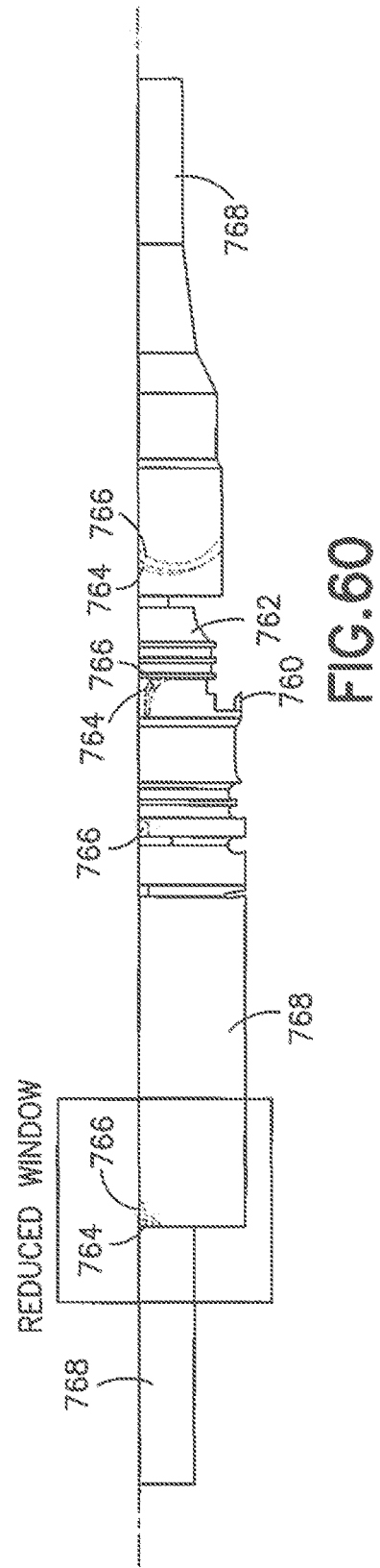

MULTI-USE BLOOD CONTROL SAFETY CATHETER ASSEMBLY

RELATED APPLICATIONS

This application claims the benefit of, and for the United States, is a continuation-in-part of, International Patent Application No. PCT/US2015/026534, filed Apr. 17, 2015, International Patent Application No. PCT/US2015/026536, filed Apr. 17, 2015, and International Patent Application No. PCT/US2015/026542, filed Apr. 17, 2015, all of which are hereby incorporated by reference in their entirety.

FIELD

Various exemplary embodiments of the invention relate to catheter assemblies.

BACKGROUND

Catheter assemblies are used to place a catheter properly into the vascular system of a patient. Once in place, catheters such as intravenous catheters may be used to infuse fluids including normal saline, medicinal compounds, and/or nutritional compositions into a patient in need of such treatment. Catheters additionally enable the removal of fluids from the circulatory system and monitoring of conditions within the vascular system of the patient.

SUMMARY OF THE INVENTION

It is an aspect of the present invention to provide a catheter assembly in which a valve actuator includes a plurality of windows specifically sized and disposed to enhance saline flushing capability. Additionally, a catheter hub includes a floating spring design that improves manufacturability and performance. Finally, the catheter hub also uses one of a plurality of materials to reduce magnetic susceptibility in the spring so that the catheter assembly can be used on a patient during a magnetic resonance imaging (MRI) procedure.

The foregoing and/or other aspects of the present invention can be achieved by providing a valve actuator that moves in a catheter assembly between a first position where a valve is closed and a second position where the valve is open, the valve actuator comprising a shaft portion at a distal end of the valve actuator that is configured to pierce the valve, a mating portion at a proximal end of the valve actuator that is configured to engage a Luer device, a diameter reduction region that connects the shaft portion and the mating portion, and a plurality of windows that extend through the valve actuator for flushing fluid, the plurality of windows being disposed in the diameter reduction region, wherein each of the plurality of windows does not extend a full length of the diameter reduction region.

The foregoing and/or other aspects of the present invention can further be achieved by providing a valve actuator that moves in a catheter assembly between a first position where a valve is closed and a second position where the valve is open, the valve actuator comprising a shaft portion at a distal end of the valve actuator that is configured to pierce the valve, a mating portion at a proximal end of the valve actuator that is configured to engage a Luer device, a diameter reduction region that connects the shaft portion and the mating portion, and a plurality of windows that extends through the valve actuator for flushing fluid, wherein the plurality of windows is disposed outside the diameter reduction region.

The foregoing and/or other aspects of the present invention can also be achieved by providing a catheter assembly comprising a catheter, a needle having a sharp distal tip disposed within the catheter, a catheter hub connected to the catheter having the needle passing therethrough, the catheter hub including a valve that selectively permits or blocks a flow of fluid through the catheter, a valve actuator that moves between a first position and a second position, and a return member that returns the valve actuator from the second position to the first position, and a needle protection member that encloses the sharp distal tip of the needle, wherein the valve actuator includes a diameter reduction region having a plurality of windows, and each of the plurality of windows does not extend a full length of the diameter reduction region.

The foregoing and/or other aspects of the present invention can also be achieved by providing a catheter assembly comprising a catheter, a needle having a sharp distal tip disposed within the catheter, a catheter hub connected to the catheter having the needle passing therethrough, the catheter hub including a valve that selectively permits or blocks a flow of fluid through the catheter, a valve actuator that moves between a first position and a second position, a return member that returns the valve actuator from the second position to the first position, and a needle protection member that encloses the sharp distal tip of the needle, wherein the valve actuator including a diameter reduction region, and a plurality of windows that extends through the valve actuator for flushing fluid, the plurality of windows being disposed outside the diameter reduction region.

The foregoing and/or other aspects of the present invention can also be achieved by providing a catheter assembly comprising a catheter, a needle having a sharp distal tip disposed within the catheter, a catheter hub connected to the catheter having the needle passing therethrough, the catheter hub including an inner diameter, a valve that selectively permits or blocks a flow of fluid through the catheter, a valve actuator that moves between a first position and a second position, and a spring that returns the valve actuator from the second position to the first position, wherein a clearance fit is provided between the spring and the inner diameter.

The foregoing and/or other aspects of the present invention can also be achieved by providing a catheter assembly comprising a catheter, a needle having a sharp distal tip disposed within the catheter, a catheter hub connected to the catheter having the needle passing therethrough, the catheter hub including a valve that selectively permits or blocks a flow of fluid through the catheter, a valve actuator that moves between a first position and a second position, and a return member that returns the valve actuator from the second position to the first position, and a needle protection member that encloses the sharp distal tip of the needle, wherein the return member comprises a metallic member with a magnetic relative permeability of less than 2.0.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 21A illustrates a sectional, side view of another exemplary embodiment of a catheter with an actuator and biasing member and a Luer connector inserted;

FIG. 21B is a front view depiction of the septum of FIG. 21A;

FIG. 21C is a sectional, side view depiction of the actuator of 21A with an elastomer molded to the tip of the actuator;

FIG. 22 is a perspective view of a side-port catheter;

FIG. 23 illustrates a sectional, side view of an exemplary embodiment of catheter with an actuator and a biasing member for a side-port catheter;

FIG. 24 illustrates a sectional, side view of another exemplary embodiment of catheter with an actuator and a biasing member for a side-port catheter;

FIG. 25 illustrates a sectional, side view of another exemplary embodiment of catheter with an actuator and a biasing member for a side-port catheter;

FIG. 26 illustrates a sectional, side view of another exemplary embodiment of catheter with an actuator and a biasing member for a side-port catheter;

FIG. 40B illustrates a sectional view of the catheter hub assembly of FIG. 40A when penetrating a septum;

FIG. 40C illustrates a left perspective sectional view of the catheter hub assembly of FIG. 40A when penetrating a septum;

FIG. 41 illustrates a sectional view of another exemplary embodiment of a catheter assembly in the needle extended position;

FIG. 42 illustrates a sectional view of the catheter assembly of FIG. 41 in the needle retracted position;

FIG. 43 illustrates a sectional view of another exemplary embodiment of a catheter assembly in the needle extended position;

FIG. 44 illustrates a sectional view of the catheter assembly of FIG. 43 in the needle retracted position;

FIG. 45 illustrates a sectional view of the catheter hub assembly and the needle hub assembly of FIG. 44;

FIG. 59 illustrates an amount of blood remaining on the valve actuator of FIG. 3 after a saline flush;

FIG. 60 illustrates an amount of blood remaining in the catheter hub with the valve actuator in the embodiment of FIG. 52 after a saline flush;

DETAILED DESCRIPTION OF EXEMPLARY EMBODIMENTS

Figure 1A:
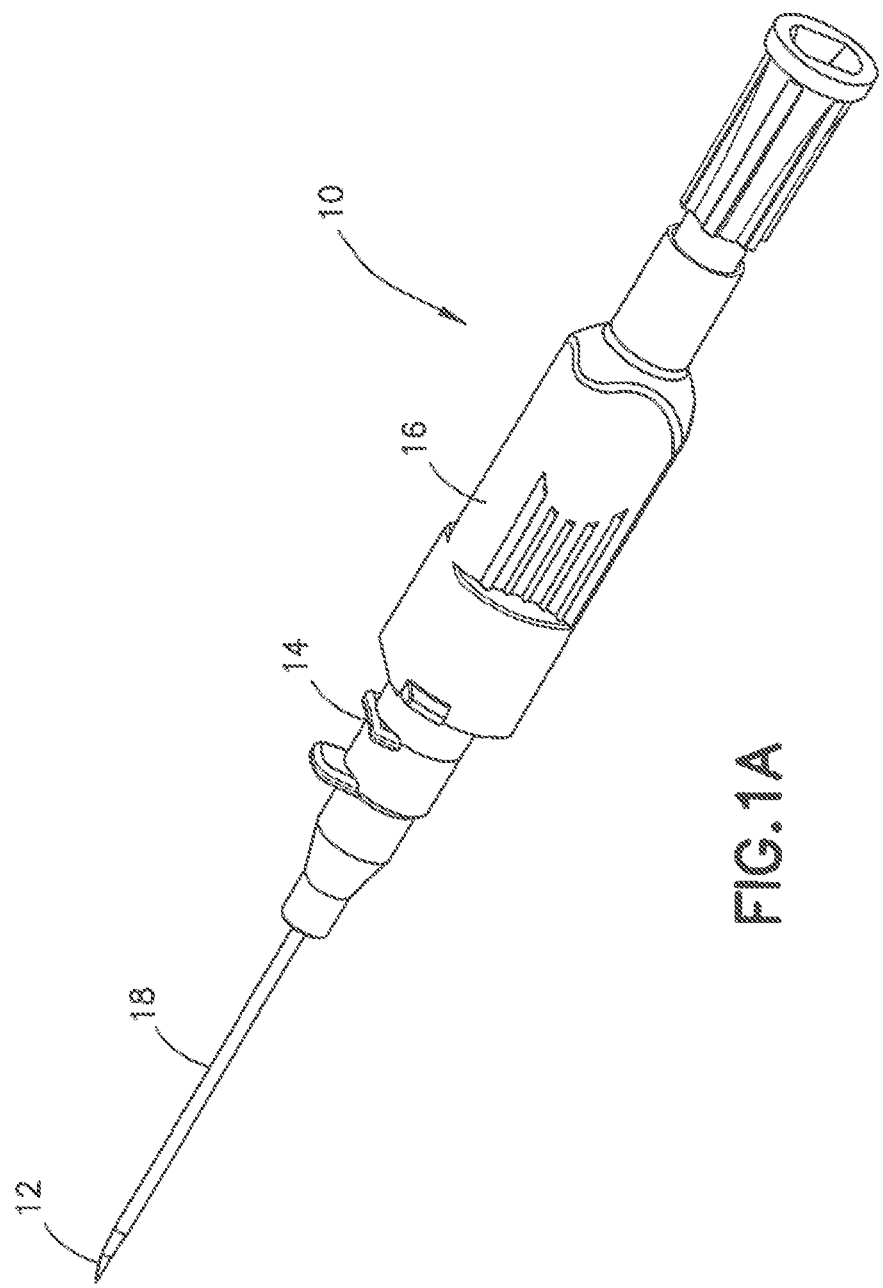
FIG. 1A is a perspective view of an exemplary catheter assembly.
Figure 1B:
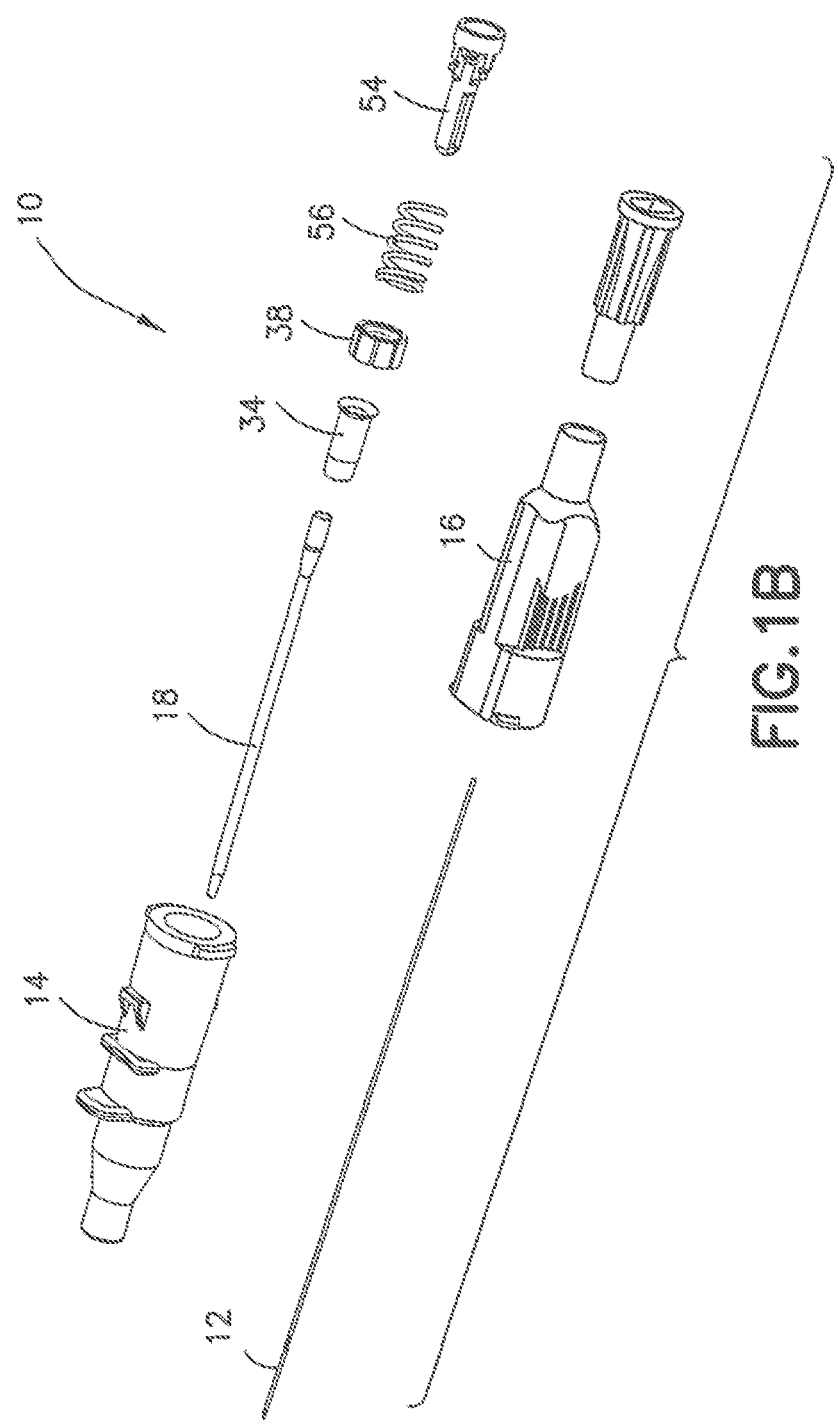
FIG. 1B is an exploded perspective view of the catheter assembly of FIG. 1A.

A catheter assembly 10, as shown in FIGS. 1A and 1B, includes a hollow introducer needle 12, a catheter hub 14, and a needle hub 16. The introducer needle 12 has a sharpened distal end and extends through the catheter hub 14. A flexible catheter tube 18 extends from the distal end of the catheter hub 14, with the needle 12 passing through the catheter tube 18. Initially, the needle 12 is inserted into a patient's vein. The catheter tube 18 is pushed along the needle 12 and into the vein following the needle 12. After the catheter tube 18 is inserted, the needle 12 is removed from the patient's vein and the catheter hub 14, leaving the catheter tube 18 in the patient as the needle 12 is discarded.

Figure 4:
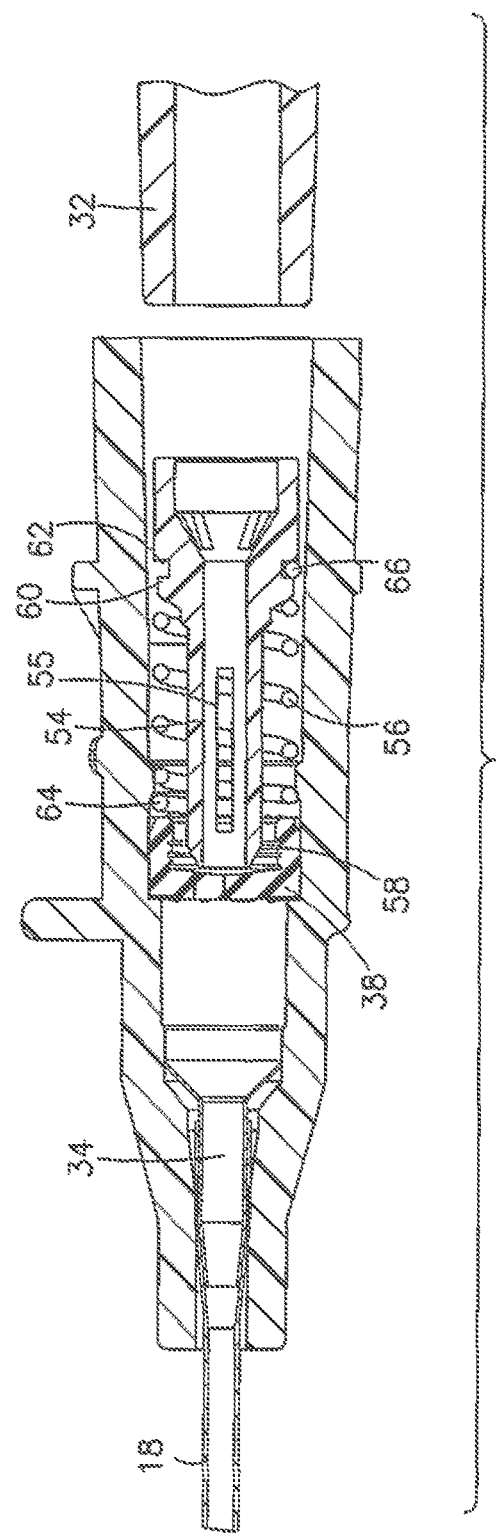
FIG. 4 is a sectional side view of the catheter hub of FIG. 3 with the introducer needle removed.

According to various exemplary embodiments, the catheter hub 14 has a distal end 20, a proximal end 22, an inner surface 24, and an outer surface 26. The distal end 20 includes a catheter opening and the proximal end includes a Luer connector opening. The inner surface 24 surrounds a channel 28 that permits fluid passage through the catheter hub 14. The outer surface 26 includes one or more projections 30 to secure a Luer connector 32 (FIG. 4) to the catheter hub 14. The projections 30 may form a threaded connection with the Luer connector 32 or they may connect to the Luer connector 32 through a snap fit or other twisting connection. One example of a standard connection is a LUER-LOK® connection. Certain types of Luer connectors 32 utilize a slip fit into the catheter hub 14. The catheter hub 14 may be made from a polymer material that is transparent or semi-transparent so that fluid flow through the catheter hub may be observed by a user or it may be made from an opaque material.

The flexible catheter tube 18 extends through the catheter opening. A metal wedge 34 may be positioned in the channel to secure the catheter tube 18 in the catheter opening. The wedge 34 has a first end engaging the catheter tube 18 and a second end engaging the inner surface 24 of the catheter hub 14. The first end of the wedge 34 has a tapered nose that allows it to easily engage the catheter tube 18. As the wedge 34 is inserted into the catheter tube 18, the catheter tube 18 expands, creating an interference fit between the catheter tube 18, the wedge 34, and the inner surface 24 of the catheter hub 14. The second end of the wedge 34 has a substantially frusta-conical shaped portion with an outer edge that engages the inner surface 24 of the catheter hub 14. A wedge flange 36 may be formed on the inner surface 24 to create a limit for distal movement of the wedge 34. A similar shoulder, tab, or groove may limit the distal movement of the wedge 34.

A pre-slit resilient septum 38 is positioned in the channel 28 and functions as a valve that forms a fluid-tight seal and selectively admits fluid to or from the flexible catheter tube 18. In other words, the valve selectively permits or blocks the flow of fluid through the flexible catheter tube 18. The septum 38 may be seated against a septum flange 40 to limit distal movement. Protrusions or other internal structure may form an interference fit with the septum 38 to retain it in place or limit its proximal movement. As best shown in FIG. 2B, the septum 38 has one or more pre-formed openings or slits 42 designed to selectively prevent unwanted fluid flow through the septum 38. The septum 38 preferably has three intersecting slits 42 forming three flaps that open when engaged by a valve actuator or a septum actuator (hereinafter actuator).

The septum 38 further includes a plurality of axial flow channels 39. The flow channels 39 are disposed on an outer circumference of the septum 38. Eight flow channels 39 equidistant from each other are illustrated, although various quantities and positions are contemplated. The flow channels 39 have an appropriate width and depth so that when the septum 38 is not opened, blood can enter and air can escape the space distal of the septum 38 in the front portion of the catheter hub 14. At the same time, the flow channels 39 are sized small enough to prevent the blood from exiting past the septum 38 (at least for some period of time). Such a configuration is possible because the intermolecular forces in the blood are greater than the intermolecular forces in air.

The septum 38 shown in FIG. 2B may be used in any of the embodiments discussed herein. Other septum configurations may be used as would be understood by one of ordinary skill in the art. When the catheter tube 18 is initially inserted into a patient, and the introducer needle 12 is removed, the septum 38 prevents blood from flowing through the channel 28 and out of the distal end. The septum 38 is made of an elastic material to form the valve, for example silicone rubber. Other elastic materials may be used and non-elastic materials may be incorporated in the septum 38 as needed.

Figure 2A:
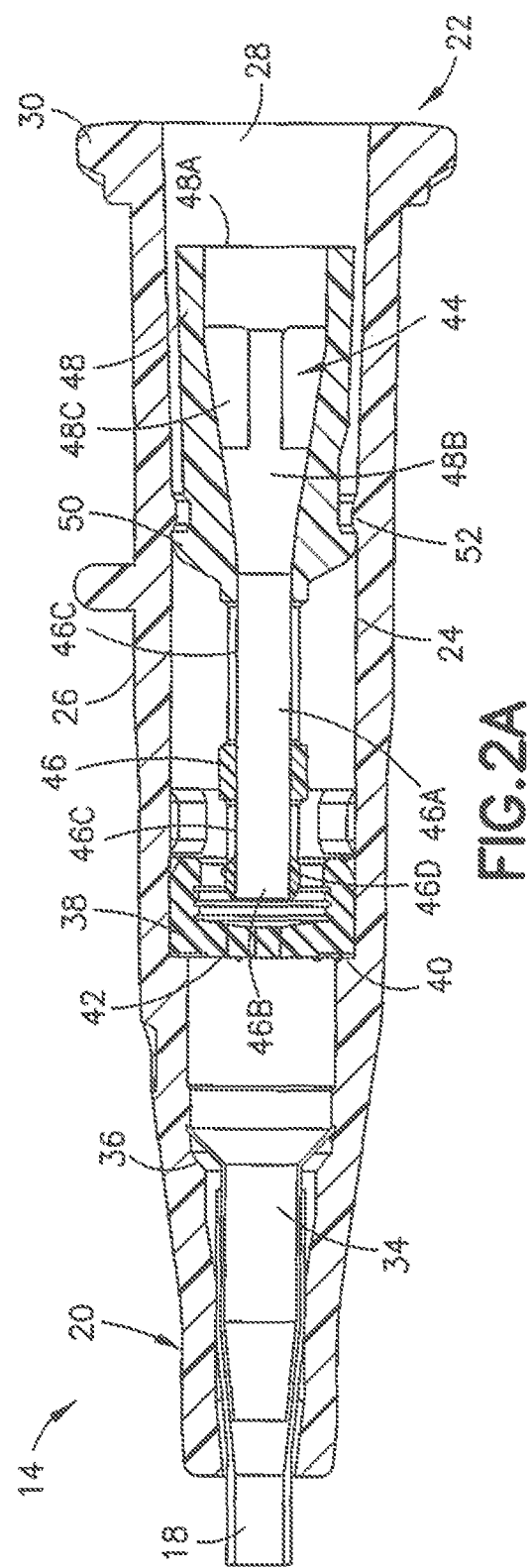
FIG. 2A is a sectional, side view of an exemplary catheter hub and actuator.
Figure 2B:
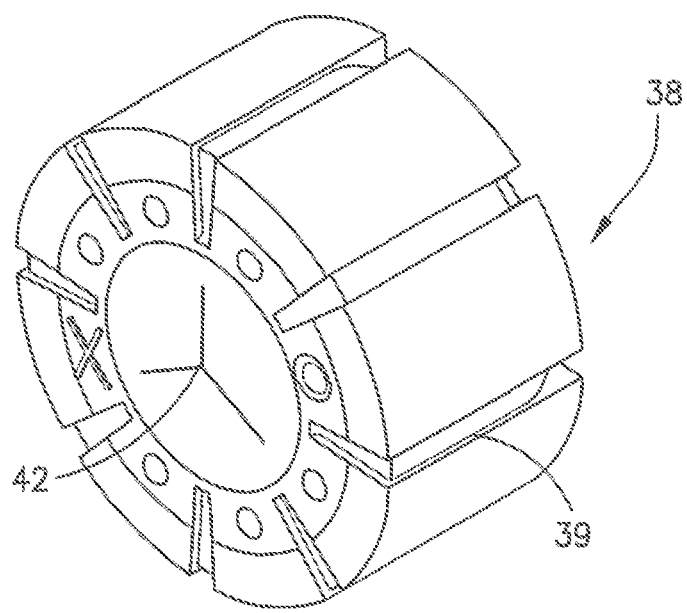
FIG. 2B is a perspective view of an exemplary septum.
Figure 3:
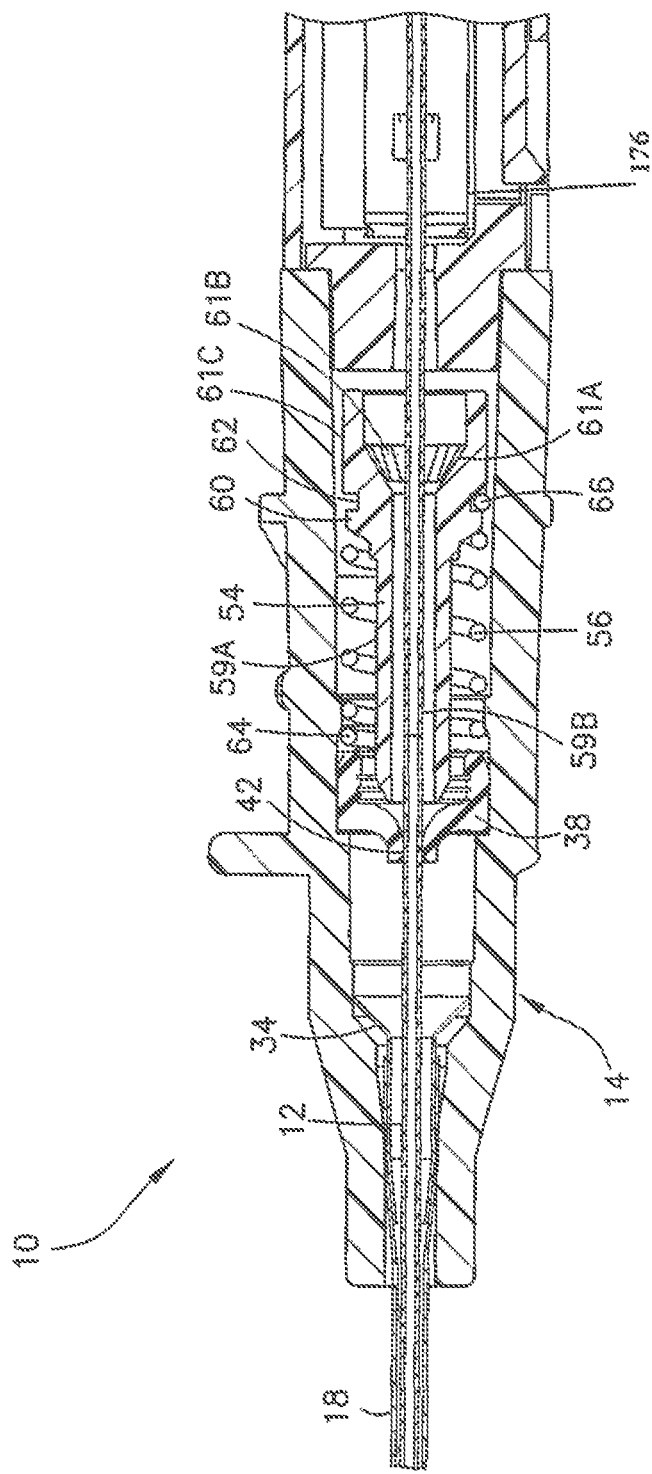
FIG. 3 is a sectional, side view of an exemplary catheter hub, actuator, and spring with an introducer needle inserted through the catheter hub.

FIG. 2A depicts an exemplary embodiment of an actuator 44 having an actuator barrel 46 surrounding an internal passage 46A. Actuators similar to that of FIG. 2A may be used in any of the embodiments described herein. The actuator 44 is positioned in the channel 28 and is axially moveable in the channel 28 to engage and open the slits 42. The actuator barrel 46 is a substantially tubular member and the internal passage 46A is substantially cylindrical to allow fluid to flow through the actuator 44 and through the septum 38 when the septum 38 is opened or penetrated by the actuator 44. The tubular member has a distal opening 46B, one or more side openings 46C, and a distal end 46D that engages and opens the slits 42. The side openings 46C of the actuator 44 allow for fluid flushing.

A conical section 48 forms the proximal end of the actuator 44. The conical section 48 is a substantially frusto-conical member that is tapered towards the actuator barrel 46 and has one or more proximal openings 48A to permit fluid flow. The conical section 48 receives or engages or abuts the end of a Luer connector (not shown). One or more tabs 50 extend from the actuator 44 to engage a respective flange 52 or one or more shoulders on the inner surface 24 of the catheter hub 14. The interaction between the tabs 50 and the flange 52 limits proximal movement of the actuator 44. The proximal opening 48A and an internal passage 48B communicating with the internal passage 46A preferably allow fluid to flow between the Luer connector and the catheter tube 18. Side openings 48C in the conical section 48 allow for fluid flushing. The actuator 44 is preferably made in one piece from a rigid or semi-rigid material, for example a rigid polymer material or a metal.

As a male Luer connector is inserted in the catheter hub 14, the end of the Luer connector slides toward the conical section 48 and abuts the actuator 44. Further movement of the Luer connector moves the actuator 44 axially toward and through the septum 38 with the distal end 46D of the actuator barrel 46 separating the one or more slits 42 to engage and open the septum 38. After the septum 38 is opened by the actuator 44, fluid is permitted to flow from the Luer connector, through the internal passages 48B and 48D of the actuator 44, and into the flexible catheter 18 or vice versa. When the Luer connector 32 is removed, the actuator barrel 46 remains in the septum 38.

FIGS. 3-8 depict an embodiment of the catheter assembly 10 that includes a return member 56 which provides a multi-use function for blood control, for example. The actuator 54 has an actuator barrel 59A surrounding an internal passage 59B. The actuator barrel 59A is a substantially tubular member and the internal passage 59B is substantially cylindrical. The tubular member has one or more openings 55 to permit fluid flow through and around the actuator barrel 59A. The openings 55 advantageously provide increased area for the fluid to move inside the catheter hub assembly. The increased area advantageously allows for fluid flushing and to prevent coagulation of fluid in the proximal and distal ends of the septum 38. Additionally, the openings 55 advantageously minimize the stagnation of fluid and allow for greater mixing.

A first end of the actuator barrel has a nose 58 with a chamfered outer surface to engage the septum 38. A frusto-conical section 61A extends from the second end of the actuator barrel 59A. The gusto-conical section 61A has one or more openings 61B to permit fluid flow therethrough. A cylindrical section 61C extends from the frusto-conical section 61A to engage a male Luer connector 32. One or more hooks 60 having an angled front surface and a slot 62 extend from the actuator barrel 59A.

In the exemplary embodiment shown in FIGS. 3-8, the return member 56 is a biasing member such as a coil spring, for example a helical compression spring with a distal end 64 and a proximal end 66. The spring can be, but is not limited to, rubber, silicone rubber, a thermal plastic, a thermal plastic elastomer, metal, plastic, an elastomeric member such as an elastomer, or another suitable resilient material. The distal end 64 of the spring forms an interference fit with the inner surface 24 of the catheter hub 14. The interference fit may be sufficient to retain the spring, even during loading, or the distal end 64 of the spring may also abut the septum 38. The proximal end 66 of the spring connects to the actuator 54, for example by fitting over the hook 60 and into the slot 62.

In other various embodiments, the actuator 54 and the biasing member 56 are combined to be a unitary structure. In various exemplary embodiments, the inner surface 24 of the catheter hub 14 and/or the outer surface of the actuator 54 and/or biasing member 56 includes undercuts, bumps, projections, tines, or other suitable structure to form a snap connection between the catheter hub 14 and the biasing member 56, and the biasing member 56 and the actuator 54. In further various exemplary embodiments, the biasing member or spring 56 and actuator 54 may be attached to each other via an engagement that does not require a snap connection including a diametric interference fit or a press fit.

FIGS. 3-7 depict the operation of the catheter hub 14 having an actuator 54 and a return member such as a biasing member or spring 56. The return member functions by returning the actuator 54 from a second position engaging the septum 38 (opening or penetrating the septum, for example) to open the valve, to a first position at a proximal end of the septum 38 (not engaging the septum 38) to close the valve. The needle 12 initially extends through the actuator 54, the septum 38, the wedge 34, and the catheter tube 18. After the needle 12 and the catheter tube 18 are inserted into a patient, the needle 12 is withdrawn, closing the septum 38.

There are two basic ways to open the septum 38, either of which can be used in the practice of the present invention. In the first way, the septum 38 can be in an opened state when the actuator 44 contacts or pushes against the slits 42 of the septum 38. When the septum 38 is opened in this way, the actuator 44 does not extend through the septum 38. Rather, the end surface of the actuator 44 is disposed on the slits 42 of the septum 38. Either the resilient slits 42 or flaps of the septum 38, or the spring 56, or both, can cause the actuator 44 to retract when operation is complete and upon removal of the axial pressure on the actuator 44. In the second way, the septum 38 can be in a penetrated state where the actuator 44 extends through the septum 38 causing the septum 38 to open. In this state, the actuator 44 requires an external force, such as the spring 56, to retract the actuator 44 and close the septum 38. In the penetrated state, the resilient slits 42 of the septum 38 cannot retract the actuator 44 on their own. Both septum states can open the septum 38 and allow fluid to be exchanged.

Figure 5:
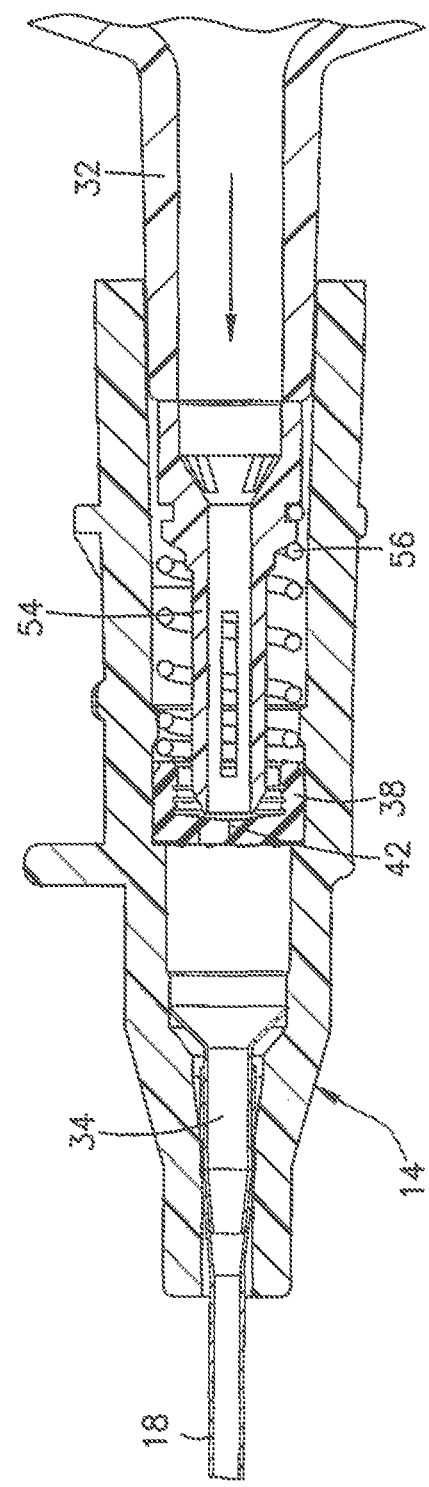
FIG. 5 is a sectional, side view of the catheter hub of FIG. 4 with a Luer connector inserted.
Figure 6:
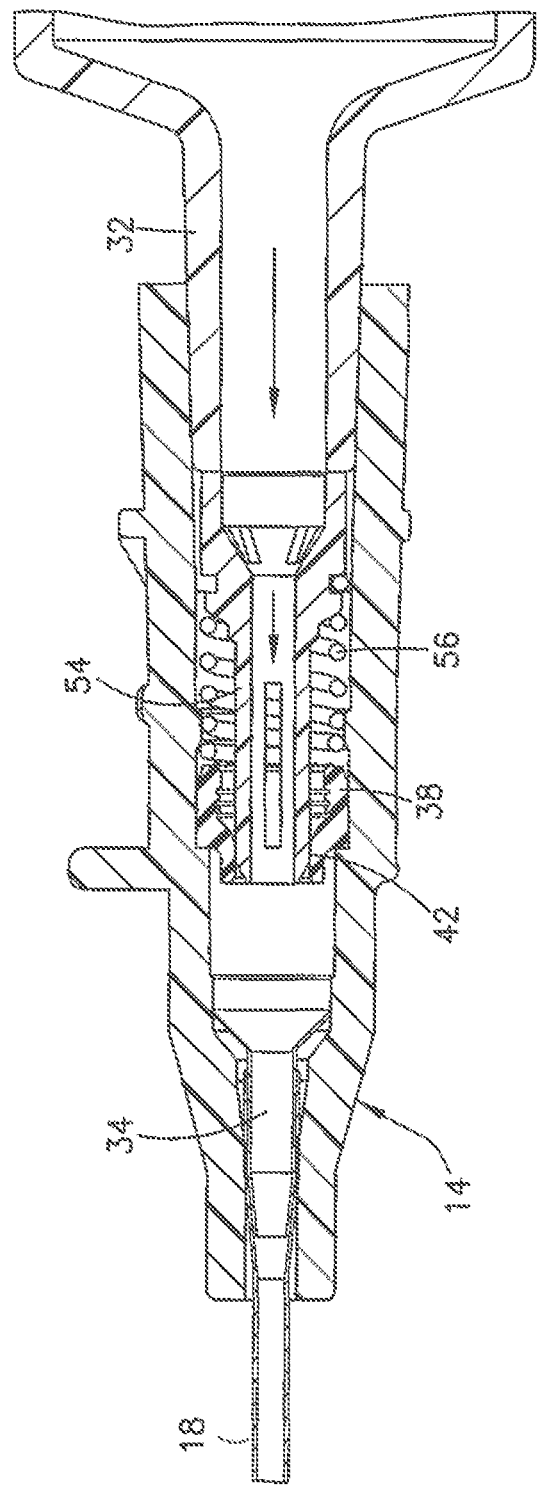
FIG. 6 is a sectional, side view of the catheter hub of FIG. 5 with the Luer connector pushing the actuator through the septum.
Figure 7:
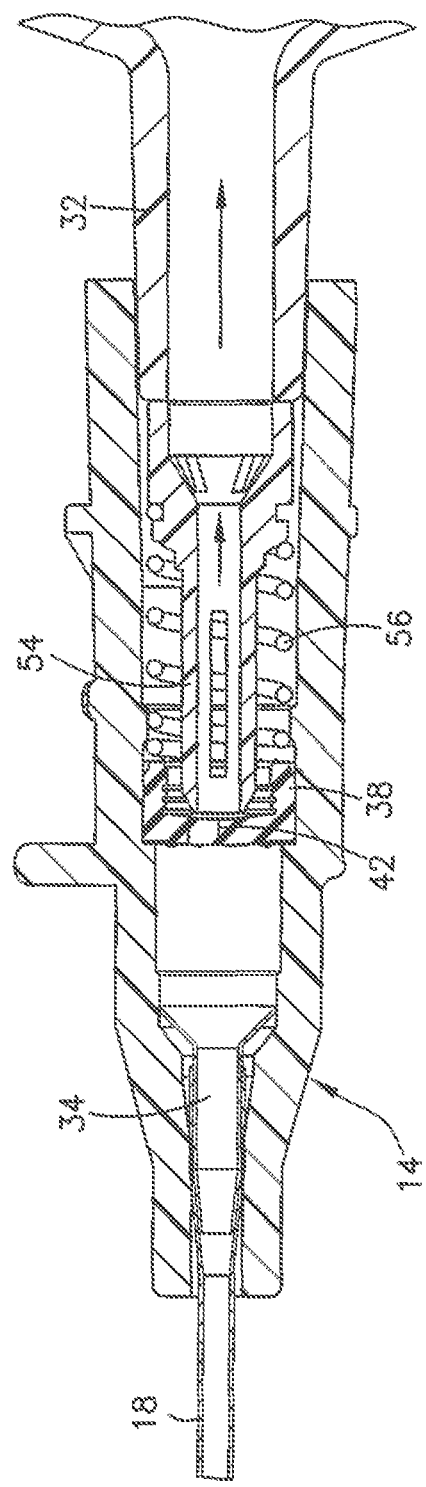
FIG. 7 is a sectional, side view of the catheter hub of FIG. 6 with the Luer connector being removed.
Figure 8:
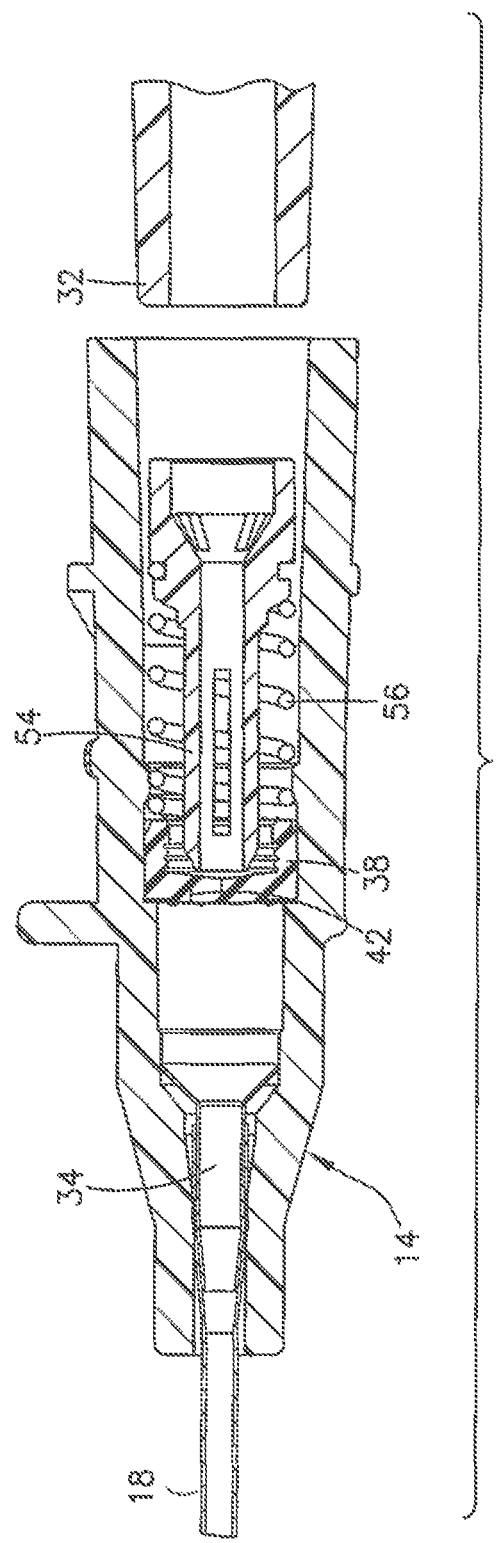
FIG. 8 is a sectional, side view of the catheter hub of FIG. 7 with the Luer connector removed.

As shown in FIGS. 5 and 6, as the male Luer connector 32 is inserted into the catheter hub 14, the Luer connector 32 moves the actuator 54 in the distal direction, compressing the spring 56. Further insertion of the Luer connector 32 moves the actuator 54 through the septum 38, opening the slits 42 and allowing fluid to flow through the catheter hub 14. As best shown in FIGS. 7 and 8, when the Luer connector 32 is removed, the spring 56 removes the actuator 54 from the septum 38, closing the slits 42 and preventing fluid from flowing therethrough. This allows the catheter assembly 10 to be reused through multiple Luer connections, as opposed to a single use catheter where the actuator would remain in the septum 38 after a Luer connector is removed. The features of the exemplary embodiments of FIGS. 3-8 may be combined with features of the other exemplary embodiments disclosed herein as appropriate.

Although the return member 56 is shown as a biasing member (e.g. spring or other resilient member) in all of the embodiments disclosed herein, the invention is not so limited. The return member may be any element or assembly that returns the actuator from its second position to its first position when a Luer connector is removed. When constituted as a biasing member, the return member 56 can be, but is not limited to, rubber, silicone rubber, a thermal plastic, or a thermal plastic elastomer. The return member 56 can also be constituted by the resilient slits 42 or flaps of the septum 38, as discussed above.

Figure 9:
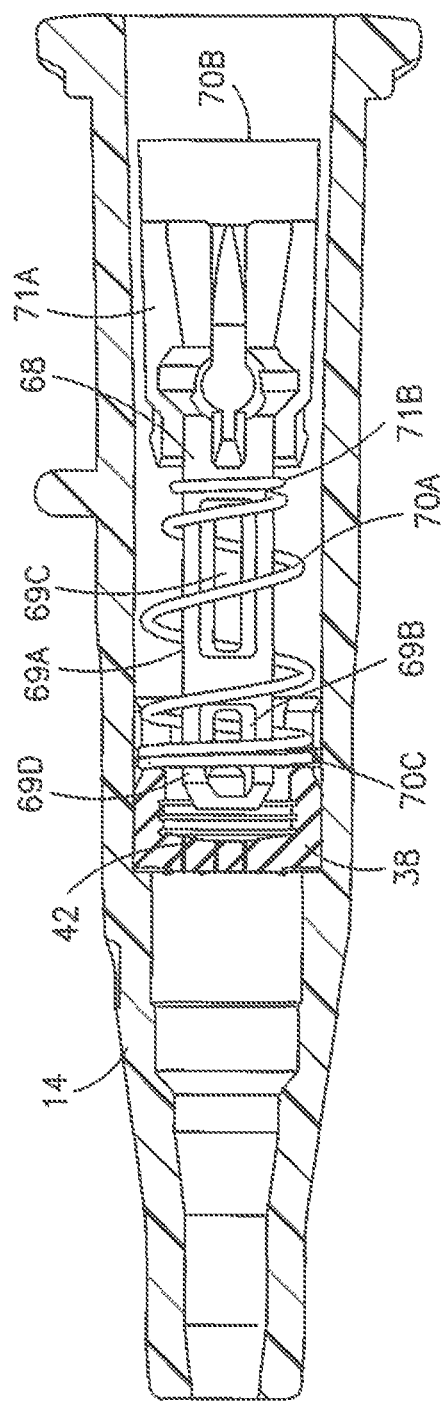
FIG. 9 is a sectional, side view of another exemplary embodiment of a catheter with an actuator and biasing member.

FIG. 9 depicts an alternative embodiment of the actuator 68 and the biasing member 70A. The actuator 68 has an actuator barrel 69A surrounding an internal passage 69B. The actuator barrel 69A is a substantially tubular member and the internal passage 69B is substantially cylindrical. A series of openings 69C are formed in the actuator barrel 69A to allow fluid to flow through and around the actuator 68. The actuator barrel 69A has a distal end 69D that engages and opens the septum 38. The distal end 69D includes a nose having a chamfered outer surface. A conical section 71A extends from the proximal end 71B of the actuator barrel 69A. The conical section 71A is a substantially frusto-conical member receives or engages the end of a Luer connector.

The biasing member is a helical metal compression spring 70A with a distal end 70B and a proximal end 70C. The distal end 70B of the spring 70A has a first outer diameter and a first inner diameter. The proximal end 71B of the spring 70A has a second outer diameter and a second inner diameter. The second outer diameter may be different from the first outer diameter and the second inner diameter may be different from the first inner diameter. The spring 70A may have a general conical shape.

In various exemplary embodiments, the first outer diameter is sized to create a first interference fit with the inner surface of the catheter hub 14. The first interference fit may be sufficient to allow compression of the spring 70A without contact between the spring 70A and the septum 38. In alternative embodiments, the septum 38 may assist in limiting the axial movement of the spring 70A. The second inner diameter is sized to create a second interference fit with the actuator 68, for example the actuator barrel 69A. The second interference fit is sufficient to retain and support the actuator 68 in place in an unstressed condition, both axially and radially, with respect to the catheter hub 14. The second interference fit may be sufficient to allow compression of the spring 70A without contact between the spring 70A and the catheter hub 14. Because of the support provided by the spring 70A, the actuator 68 is held, substantially self-centered and does not touch the inside walls of the catheter hub 14 as shown. The spring 70A retaining the actuator 68 in the catheter hub 14 provides an advantage over the catheter shown in FIG. 2, because the actuator tabs 50 and the corresponding shoulder 52 extending from the inner surface are removed. Removal of the tabs 50 and shoulder 52 reduces complexity of the device. In various alternative embodiments, the tabs 50 are used to retain the actuator and the spring 70A is freely positioned in the catheter hub 14 without an interference fit with the catheter hub 14 or the actuator 68.

In accordance with the illustrated embodiment, the spring's first outer and inner diameters are greater than the second outer and inner diameters. The pitch of the spring 70A also varies from the distal end to the proximal end. The spring 70A may have one or more coils that are touching or very closely positioned at the distal end and one or more coils that are touching or very closely positioned at the proximal end in an unloaded state. The variable pitch of the spring 70A allows stiffness to be concentrated at the distal and proximal ends to assist in retaining the interference fit while also allowing for sufficient compression through the middle of the spring 70A. The features of the exemplary actuator 68 and biasing member 70A depicted in FIG. 10 may be combined with features of the other exemplary embodiments disclosed herein as appropriate.

As a Luer connector (not shown) is inserted in the catheter hub 14, the end of the Luer connector abuts the conical section of the actuator 68. Further movement of the Luer connector moves the actuator 68 axially toward and through the septum 38 with the first end of the actuator barrel separating the one or more slits. Movement of the actuator 68 toward the septum 38 compresses the spring 70A. After the septum 38 is opened, fluid is permitted to flow through the catheter hub 14. The compression of the spring 70A is maintained by the Luer connector. As the Luer connector is removed, the spring 70A returns the actuator to its initial position, removing the actuator 68 from the septum 38. After the actuator 68 is removed, the septum 38 returns to the closed position, preventing fluid from flowing therethrough. The features of the exemplary embodiments of FIG. 9 may be combined with features of the other exemplary embodiments disclosed herein as appropriate.

Figure 10:
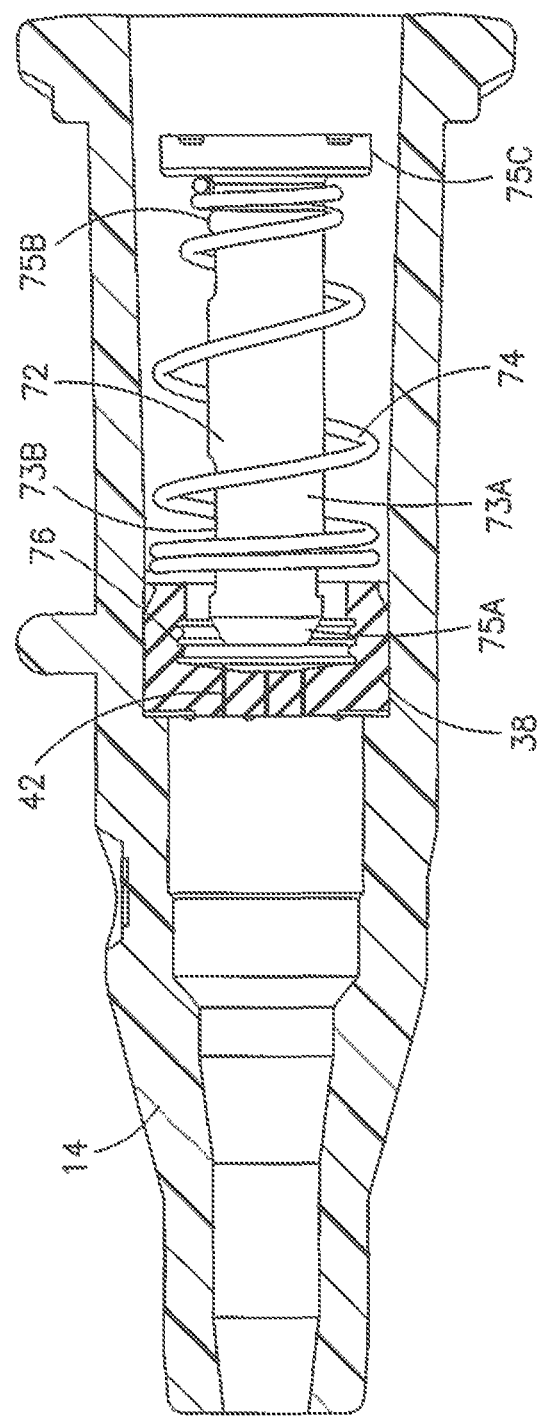
FIG. 10 is a sectional, side view of another exemplary embodiment of a catheter with an actuator and biasing member.

FIG. 10 depicts another alternative embodiment of a catheter hub 14 having an actuator 72 and a return or biasing member 74. The actuator 72 has an actuator barrel 73A surrounding an internal passage. The actuator barrel 73A is a tubular member surrounding a cylindrical internal passage. A series of openings 73B are formed in the tubular member to allow fluid to flow through and around the actuator 72. The actuator barrel 73A has a first end 75A that engages and opens the slits of the septum 38. The first end 75A includes a nose having a chamfered outer surface. A cylindrical section 75C extends from the second end 75B of the tubular portion. The cylindrical section 75C may have a conical aperture for receiving a Luer connector or the aperture may be a continuation of the cylindrical internal passage.

The return or biasing member in FIG. 10 is a helical metal compression spring 74 with a distal end and a proximal end. The distal end is interference fit with the inner surface of the catheter hub 14 and the proximal end is interference fit with the actuator 72. The inner surface may have a channel, groove, slot, or other depression 76 to receive the distal end of the spring 74. The spring 74 depicted in FIG. 10 may be similar to, or the same as, the spring 70A depicted in FIG. 9.

As discussed above, the conical spring 74 supports the actuator end and thereby allows for removal of the actuator tabs 50. The catheter 10 is designed for use with different sized Luer connectors that penetrate the interior channel at different lengths. Because the tabs 50 of the exemplary actuator 44 depicted in FIG. 2 cannot travel through the septum 38, the length of the tubular portion is increased to accommodate the different sized Luer connectors. As best shown in the exemplary embodiment of FIG. 10, by removing the tabs 50, the actuator 72 and the catheter hub 14 can be shortened, reducing the size and the cost of the device. The features of the exemplary embodiments of FIG. 10 may be combined with features of the other exemplary embodiments disclosed herein as appropriate.

Figure 11:
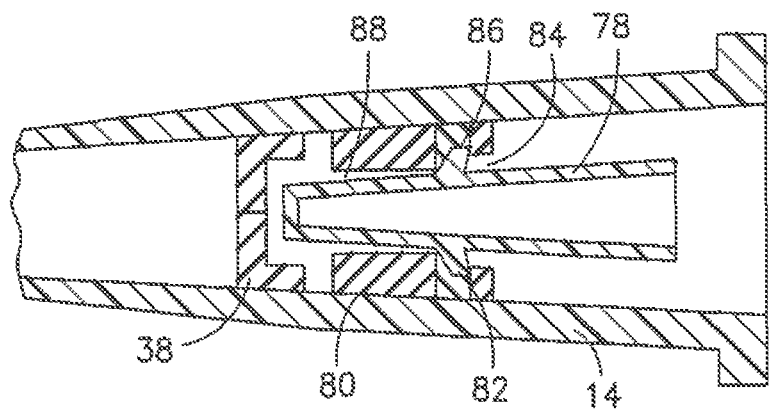
FIG. 11 illustrates a sectional, side view of another exemplary embodiment of a catheter with an actuator and biasing member.

FIG. 11 depicts another alternative embodiment of a catheter hub 14 having an actuator 78 and a return or biasing member 80. The actuator 78 has an actuator barrel surrounding an internal passage. The actuator barrel and the internal passage have a conical shape tapering from the proximal end to the distal end of the catheter hub. The actuator barrel has a first end that engages and opens the slits 42. The first end includes a nose having a chamfered outer surface. One or more protrusions 82 extend radially from the barrel to engage the biasing member 80. The protrusions 82 may be a single, frusto-conical flange extending around the outer surface of the barrel, one or more tabs extending from the barrel, or other similar structure.

The biasing member 80 in FIG. 11 is preferably an elastomer spring having an outer surface engaging the inner surface of the catheter hub 14 and an aperture receiving at least a portion of the actuator 78. The biasing member 80 can also be, but is not limited to, rubber, silicone rubber, a thermal plastic, or a thermal plastic elastomer. In accordance with an exemplary embodiment, the aperture includes a proximal opening 84, a middle opening 86, and a distal opening 88. The proximal opening 84 has a substantially cylindrical shape with a first diameter. The middle opening 86 has a second diameter larger than the first diameter. The middle opening 86 may cylindrical or it may be bound by one or more angled walls to having a substantially frusto-conical shape. For example, the middle opening 86 may be bound by walls having an angle that corresponds to the angle of the actuator protrusions 82. The distal opening 88 has a substantially cylindrical shape and diameter that is smaller than the diameter of the proximal opening 84 and a diameter smaller than the middle opening 86. In various exemplary embodiments, the size, shape, and configuration of the elastomer spring and the openings may vary depending on the catheter hub 14 and the actuator 78.

The actuator 78 is placed into the elastomer spring 80 so that at least a portion of the first end of the actuator barrel extends through and protrudes from the elastomer spring 80. The actuators protrusions 82 sit in the middle opening 86 to retain the actuator 78 in place and resist proximal movement of the actuator 78. The second end of the actuator extends from the proximal opening 84 to receive or engage a male Luer connector (not shown). As a Luer connector is inserted, the actuator 78 is moved in the distal direction against the bias of the elastomer spring 80, elastically deforming the elastomer spring 80. As the Luer connector is removed, the elastomer spring 80 returns the actuator 78 substantially to its initial position. The features of the exemplary actuator and biasing member depicted in FIG. 11 may be combined with features of the other exemplary embodiments disclosed herein.

Figure 12:
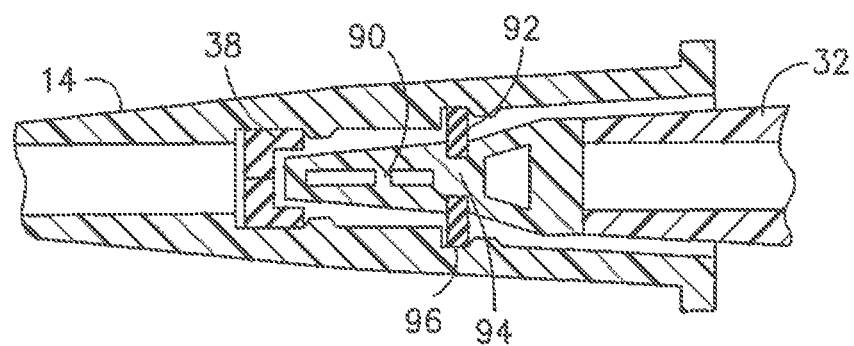
FIG. 12 illustrates a sectional, side view of another exemplary embodiment of a catheter with an actuator and biasing member.

FIG. 12 depicts another alternative embodiment of a catheter hub 14 having an actuator 90 and a return or biasing member 92. A first end of the actuator 90 has an actuator barrel surrounding an internal passage. The actuator barrel has a substantially frusta-conical shape tapering from the distal end to the proximal end of the catheter hub. The actuator barrel has one or more openings permitting fluid flow through the actuator. The actuator 90 includes a second end for receiving or engaging a Luer connector. The second end has a substantially frusto-conical shape. The second end may also include one or more openings and an internal passage. A middle portion 94 connects the first end and the second end of the actuator 90. The middle portion 94 has a substantial cylindrical shape surrounding an internal passage.

The biasing member 92 in FIG. 12 is preferably an elastic washer. The washer 92 has an outer surface that engages the inner surface of the catheter hub 14. The inner surface of the catheter hub may include a slot or groove 96 to receive and retain the washer 92. The washer 92 has an inner diameter that receives the middle portion 94 of the actuator 90. The middle portion 94 may have a diameter that is smaller than the frustum of the second end and smaller than the base of the first end, retaining the washer against a first flange formed by the first end and a second flange formed by the second end. The shape, size, and configuration of the actuator 90 and the washer 92 may vary to accommodate one another.

The actuator 90 is placed into the washer 92 so that the first end of the actuator 90 extends through and protrudes from one side of the washer 92 to engage the septum 38. The second end of the actuator 90 extends from the washer 92 to receive or engage a male Luer connector 32. As the Luer connector 32 is inserted, the actuator 90 is moved in the distal direction against the bias of the washer 92, elastically stretching the washer 92. Further insertion of the Luer connector 32 moves the actuator 90 through the septum 38, opening the slits 42. As the Luer connector 32 is removed, the washer 92 returns the actuator 90 to its initial position. In various additional embodiments, the washer 92 can be, but is not limited to, rubber, silicone rubber, a thermal plastic, a thermal plastic elastomer, a spring washer, an elastomeric washer, a plurality of elastic bands, a compression spring, an extension spring, a disc spring, or other suitable biasing member. The features of the exemplary actuator 90 and biasing member 92 depicted in FIG. 12 may be combined with features of the other exemplary embodiments disclosed herein as appropriate.

Figure 13:
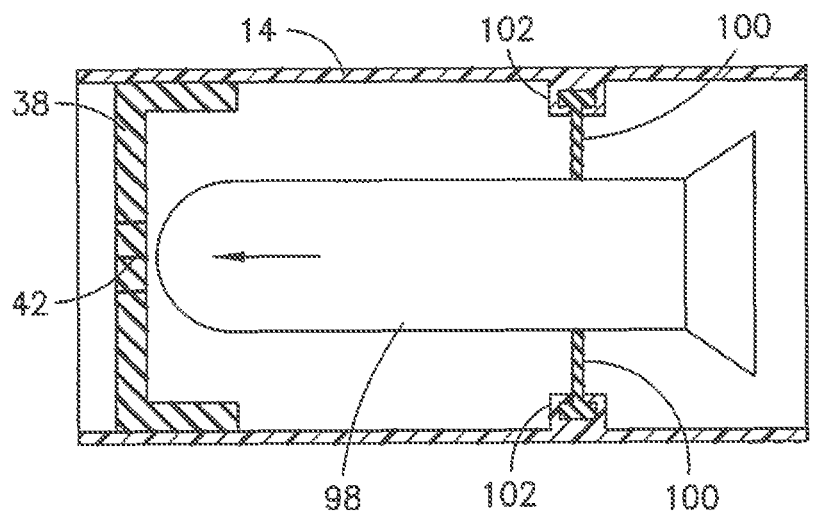
FIG. 13 illustrates a sectional, side view of another exemplary embodiment of a catheter with an actuator and biasing member.

FIG. 13 depicts another alternative embodiment of a catheter hub 14 having an actuator 98 and a return or biasing member 100. The actuator 98 has an actuator barrel surrounding an internal passage. The actuator barrel has a first end that engages and opens the slits 42. The actuator 98 includes a second end for receiving or engaging a male Luer connector (not shown).

The biasing member in FIG. 13 can be, but not limited to, one or more elastic members 100, for example, a circular or radially extending silicone member, a plurality of elastic bands, rubber, silicone rubber, a thermal plastic, or a thermal plastic elastomer. In various exemplary embodiments, the elastic bands are made from silicone or silicone rubber. The biasing member 100 is connected to a fixed support 102 attached to the inner surface of the catheter hub 14. The fixed support may be a single member extending radially around the inner surface or it may be one or more isolated blocks depending on the type of biasing member.

The biasing member 100 receives and/or connects to the actuator 98 to retain the actuator 98 in an unstressed position. As a male Luer connector is inserted, the actuator 98 is moved in the distal direction stretching the biasing member 100. As the Luer connector is removed, the biasing member 100 returns the actuator 98 to its initial position. The features of the exemplary actuator 98 and biasing member 100 depicted in FIG. 13 may be combined with features of the other exemplary embodiment disclosed herein as appropriate.

Figure 14:
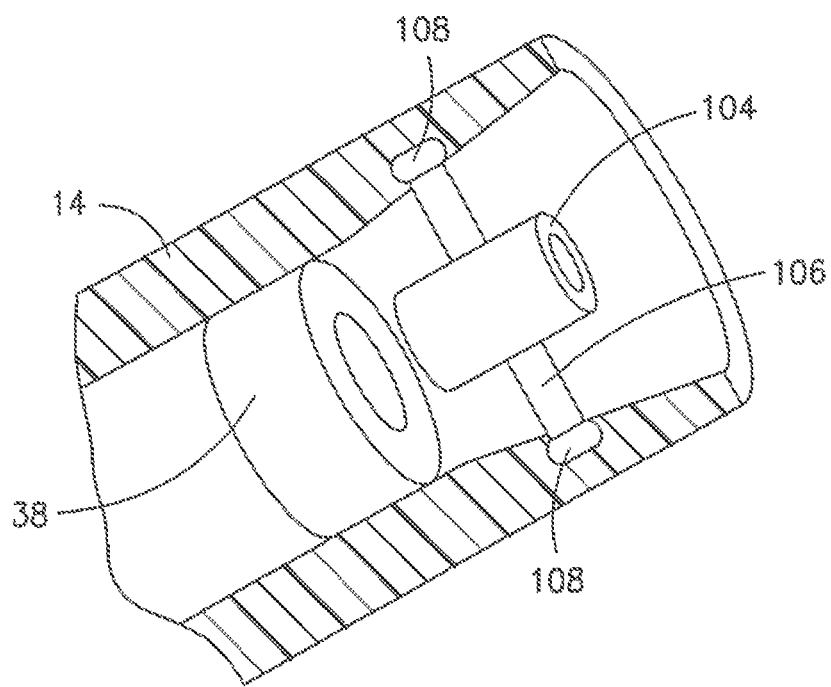
FIG. 14 illustrates a sectional, isometric view of another exemplary embodiment of a catheter with an actuator and biasing member.

FIG. 14 depicts another alternative embodiment of a catheter hub 14 having an actuator 104 and a return or biasing member 106. The biasing member 106 is similar to those discussed above with respect to FIG. 13. The actuator has an actuator barrel surrounding an internal passage. The actuator barrel has a first end that engages and opens the slits 42. The actuator includes a second end for receiving or engaging a Luer connector (not shown). The actuator barrel and catheter hub 14 are shorter than those depicted in other embodiments, although any of the actuators or catheter hubs described herein may be used with this embodiment. The biasing member 106 may be, but is not limited to, rubber, silicone rubber, a thermal plastic, a thermal plastic elastomer, one or more bands, a radially extending member, or other suitable biasing member. The biasing member 106 includes a flange 108 that fits into a groove or slot in the catheter hub 14. The features of the exemplary actuator 104 and biasing member 106 depicted in FIG. 14 may be combined with features of the other exemplary embodiments disclosed herein as appropriate.

Figure 15A:
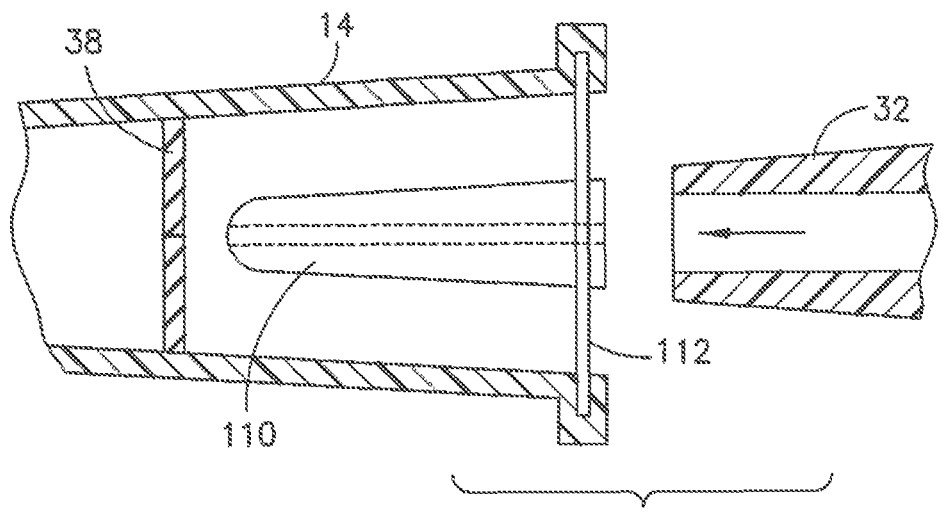
FIG. 15A illustrates a sectional, side view of another exemplary embodiment of a catheter with an actuator and biasing member.
Figure 15B:
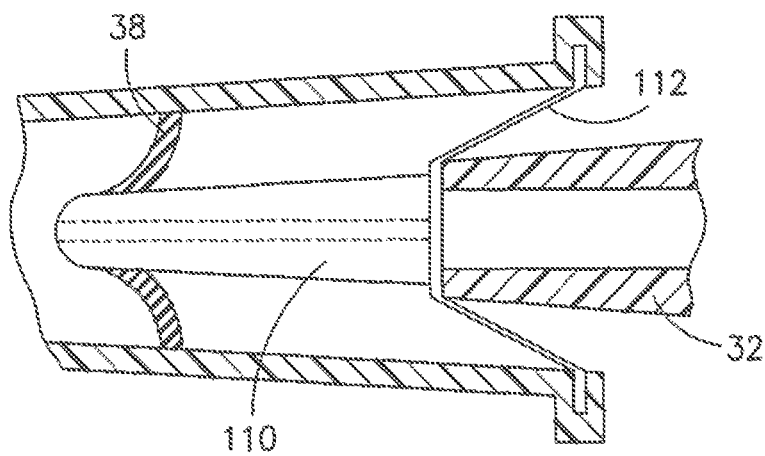
FIG. 15B is a sectional, side view of the catheter of FIG. 15A with a Luer connector inserted.

FIGS. 15A-15B depicts another alternative embodiment of a catheter hub 14 having an actuator 110 and a return or biasing member 112. The actuator 110 has an actuator barrel surrounding an internal passage. The actuator barrel has a first end that engages and opens the slits 42. The first end includes a nose having a chamfered outer surface. The second end of the actuator barrel receives or engages a male Luer connector 32.

The biasing member is an elastic band or disk 112 that is connected near the second end of the actuator 110. The elastic band 112 may be made from, but is not limited to, latex, rubber, silicone rubber, a thermal plastic, a thermal plastic elastomer, or other suitable elastic material. A first end of the elastic band 112 is connected to the catheter hub 14. A second end of the elastic band 112 is connected to the actuator 110, for example by an interference fit, or other mechanical connection, or through a chemical bond such as an adhesive or molded bond. The features of the exemplary actuator 110 and biasing member 112 depicted in FIGS. 15A-B may be combined with features of the other exemplary embodiments disclosed herein as appropriate.

Figure 16:
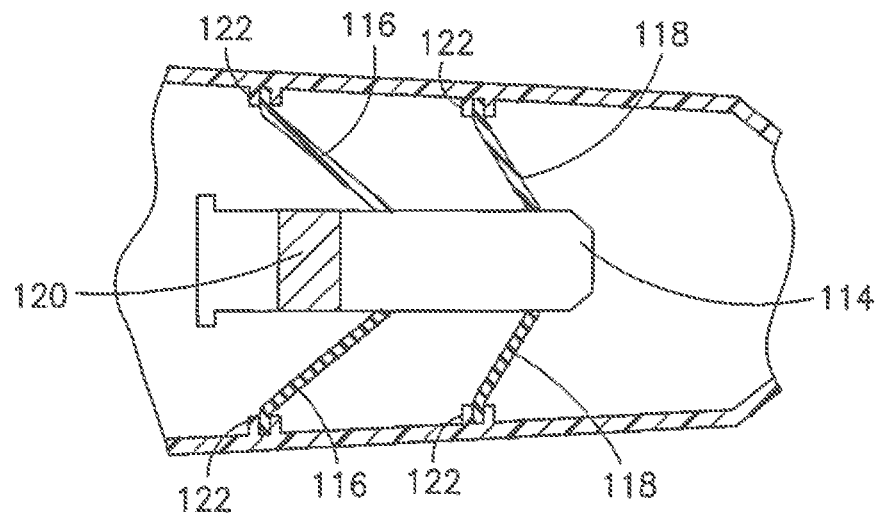
FIG. 16 illustrates a sectional, side view of another exemplary embodiment of a catheter with an actuator and biasing member.

FIG. 16 depicts another alternative embodiment of a catheter hub 14 having an actuator 114 and a return member comprising a first biasing member 116 and a second biasing member 118. The actuator 114 has an actuator barrel surrounding an internal passage. The actuator barrel has a first end that engages and opens the slits 42. The first end includes a nose having a chamfered outer surface, Extending from the second end of the actuator barrel is a cylindrical member for receiving or engaging a Luer connector (not shown). A compressible section 120 is positioned in the actuator barrel. The compressible section 120 is made from a suitable compressible material, for example an elastomer or a polymer.

Similar to the biasing members depicted in FIGS. 13-15B, the first and second biasing members 116, 118 of FIG. 16 may be one or more bands of elastic material, a radially extending member, or other suitable biasing member. In various additional embodiments, the biasing members depicted in FIGS. 13-16 may be, but are not limited to, a spring washer, an elastomeric washer, a plurality of elastic bands, a compression spring, an extension spring, a disc spring, rubber, silicone rubber, a thermal plastic, a thermal plastic elastomer or other suitable biasing member. The first and second biasing members 116, 118 are connected to the catheter hub 14 through one or more support blocks 122. In various exemplary embodiments, only a single biasing member is used.

As a Luer connector is inserted, the Luer connector engages the compressible insert 120 and moves the actuator 114 in the distal direction against the bias of the first and second biasing members 116, 118. Further insertion of the Luer connector moves the actuator through the septum (not shown), opening the slits 42. The first and second biasing member 116, 118 and the compressible insert 120 are configured so that the actuator 114 may advance a certain distance until the resilient force of the biasing members 116, 118 is greater than the force needed to compress the insert 120. At this point, the insert 120 deforms so that further insertion of the Luer connector does not result in further distal movement of the actuator 114. As the Luer connector is removed, the insert 120 expands to its normal volume and the first and second biasing members 116, 118 return the actuator 114 to its initial position. The features of the exemplary actuator 114 and biasing members 116, 118 depicted in FIG. 16 may be combined with features of the other exemplary embodiments disclosed herein.

Figure 17:
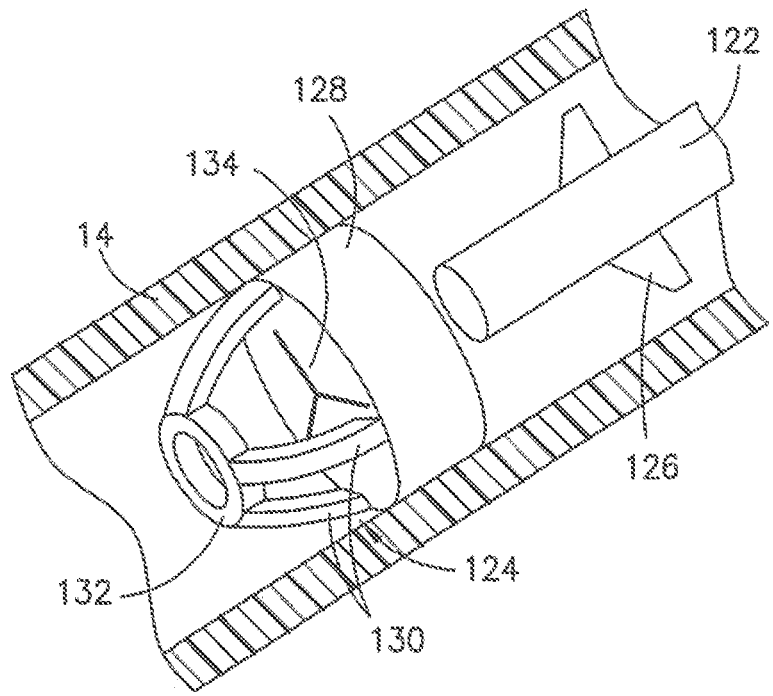
FIG. 17 illustrates a sectional, perspective view of another exemplary embodiment of a catheter with an actuator and biasing member.

FIG. 17 depicts another alternative embodiment of a catheter hub 14 having an actuator 122 and a return or biasing member 124. The actuator 122 has an actuator barrel surrounding an internal passage. The actuator barrel has a first end that engages and opens the slits 42. Extending from the second end of the actuator barrel is a member (not shown) for receiving or engaging a Luer connector. One or more protrusions 126 extend from the actuator radially towards the inner surface of the catheter hub 14. The protrusions 126 engage tabs (not shown) on the catheter hub 14 to limit the axial movement of the actuator 122, similar to the embodiment depicted in FIG. 2.

The biasing member 124 of FIG. 17 extends from the septum 128 in the distal direction. The biasing member 124 includes two or more arms 130 connected to a central hub 132. The central hub 132 is shown as a cylindrical member having an opening. The central hub 132 is configured to engage at least a portion of a front end of the actuator 122. Various sizes, shapes, and configurations of the central hub 132 may be used depending on the catheter hub 14 and the actuator 122. The biasing member 124 is preferably made from an elastic material, for example a silicone rubber. The biasing member 124 can also be made from, but is not limited to, rubber, silicone rubber, a thermal plastic, or a thermal plastic elastomer. The septum 128 and the biasing member 124 may be unitarily formed or the septum 128 and/or slits 42 may be formed separately from the biasing member.

In various exemplary embodiments, the septum 38 is configured to return the actuator to its initial position. As a male Luer connector (not shown) is inserted, the actuator 122 is moved in the distal direction, opening the slits 42 and passing through the septum 128. The septum 38 includes one or more slits 134 with the slits 134 defining two or more flaps. In the exemplary embodiment illustrated in FIG. 17, the septum 38 has three slits 134 defining three triangular flaps. As the actuator 122 is inserted into the septum 38, the flaps move in the distal direction to receive the actuator 122. The flaps are resilient and exert a biasing force on the actuator 122, which may be sufficient, depending on the depth of insertion of the actuator 122, to return the actuator 122 substantially to its initial position or at least to a position that allows the slits 42 to close.

As mentioned above, the length of a Luer connector varies, and the depth of penetration of the Luer connector into the catheter hub 14 and the resulting movement of the actuator 122 varies depending on the Luer connector. At a certain travel distance of the actuator 122 through the septum 38, the septum 38 is not capable of returning the actuator 122 to a position that allows the slits 42 to close. In accordance with the exemplary embodiment, the biasing member 124 is configured to bias the actuator 122 at least to a point where the slits 42 can move the actuator 122 to a position that allows the septum 38 to close. If the penetration of the Luer connector is long enough, the first end of the actuator 122 moves through the septum 38 and engages the biasing member 124, for example the central hub 132. Further movement of the actuator 122 stretches the arms 130. As the Luer connector is removed, the biasing member 124 moves the actuator 122 in the proximal direction until the biasing member 124 is in an unstressed state. At this point, the septum 38 moves the actuator 122 in the proximal direction a sufficient distance to allow the slits 42 to close. The features of the exemplary actuator 122 and biasing member 124 depicted in FIG. 17 may be combined with features of the other exemplary embodiments disclosed herein as appropriate.

Figure 18:
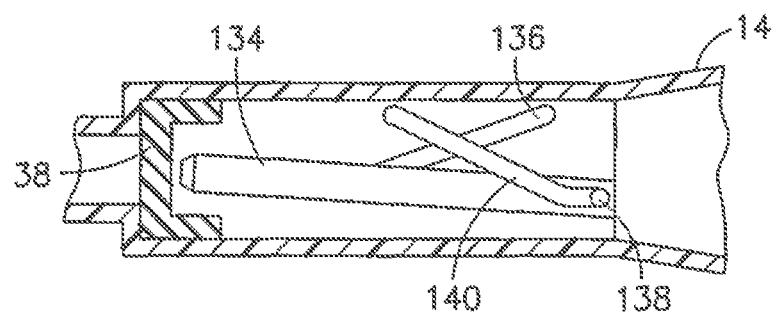
FIG. 18 illustrates a sectional, side view of another exemplary embodiment of a catheter with an actuator and biasing member.

FIG. 18 depicts another alternative embodiment of a catheter hub 14 having an actuator 134 and a return or biasing member 136. The actuator 134 has an actuator barrel surrounding an internal passage. The actuator barrel has a first end that engages and opens a septum 38. The first end includes a nose having a chamfered outer surface. The second end of the actuator barrel receives or engages a Luer connector (not shown). A pin 138 extends radially from the side of the actuator barrel. The pin 138 mates with a slot 140 formed in the catheter hub 14. In an exemplary embodiment, the slot 140 is a cam slot that has a first portion extending substantially in an axial direction of the catheter hub 14 and a second portion extending obliquely, axially in the distal direction and radially upwards, from the first portion.

The biasing member 136 of FIG. 18 can be, but is not limited to, rubber, silicone rubber, a thermal plastic, a thermal plastic elastomer, a spring, leaf spring, an elastic band, or other resilient member. The biasing member 136 may exert a force on the actuator 134 in both the axial and radial directions or only in the radial direction. In an exemplary embodiment, the majority of the force exerted by the biasing member 136 is in the radial direction. As the Luer connector is inserted into the catheter hub 14, the Luer connector moves the actuator 134 in the distal direction. Movement of the actuator 134 causes the pin 138 to slide in the cam slot 140, forcing the actuator 134 to move radially as well as axially. As the Luer connector is removed, the biasing member 136 forces the actuator back down, moving the pin 138 along the cam slot 140 to its initial position. In various exemplary embodiments, the biasing member 136 may only act in the radial direction, for example radially downward in the depicted orientation, with sufficient force to slide the pin 138 along the cam slot 140 to the initial position. The features of the exemplary actuator 134 and biasing member 136 depicted in FIG. 18 may be combined with features of the other exemplary embodiments disclosed herein as appropriate.

Figure 19A:
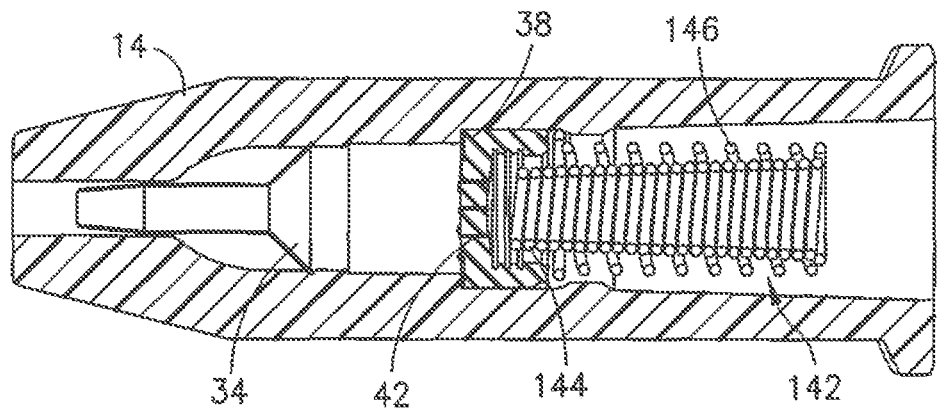
FIG. 19A illustrates a sectional, side view of another exemplary embodiment a catheter with an actuator and biasing member.
Figure 19B:
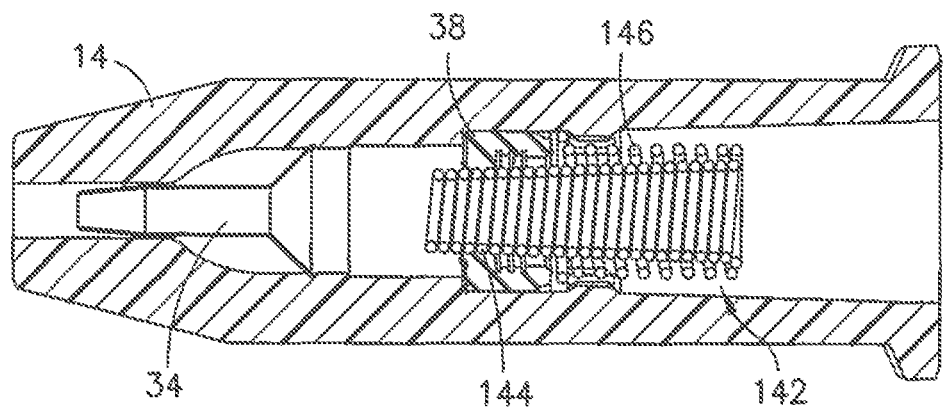
FIG. 19B is a sectional, side view of the catheter of FIG. 19A pushed through the septum.

FIGS. 19A-19B depict another alternative embodiment of a catheter hub 14 wherein the actuator and the return or biasing member are constituted by a single spring 142. The spring 142 has a first series of windings 144 that extend in the axial direction. The first series of windings 144 have a first end that extends through the septum 38. The first series of windings 144 may have a first inner diameter at a distal end and a second inner diameter larger than the first inner diameter at a proximal end. A second series of windings 146 extend around at least a portion of the first series of windings 144. The second series of windings 146 may be coaxial with the first series of windings 144 and have a first inner diameter at a proximal end and a second inner diameter greater than the first inner diameter at a distal end. The second series of windings 146 has at least one coil that forms an interference fit with the catheter hub 14. The catheter hub 14 may have a shoulder extending around the inner surface to limit movement of the first and second windings 144, 146.

As a male Luer connector is inserted, the first series of windings 144 are moved in the distal direction, compressing the second series of windings 146. Further insertion of the Luer connector moves the first set of windings 144 through the septum 38, opening the slits 42. As the Luer connector is removed, the second set of windings 146 return the first set of windings 144 to their initial position. The features of the exemplary actuator and biasing member 142 depicted in FIGS. 19A-19B may be combined with features of the other exemplary embodiments disclosed herein as appropriate.

Figure 20A:
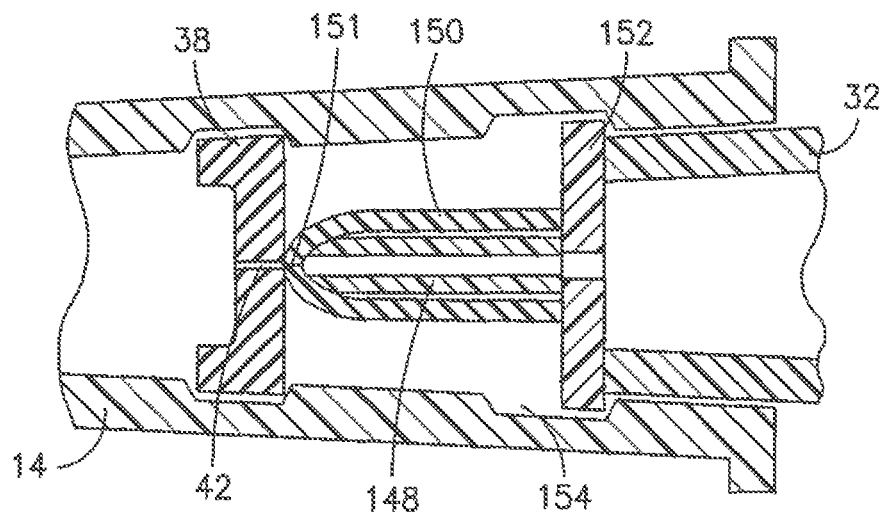
FIG. 20A illustrates a sectional, side view of another exemplary embodiment of a catheter with an actuator and biasing member.
Figure 20B:
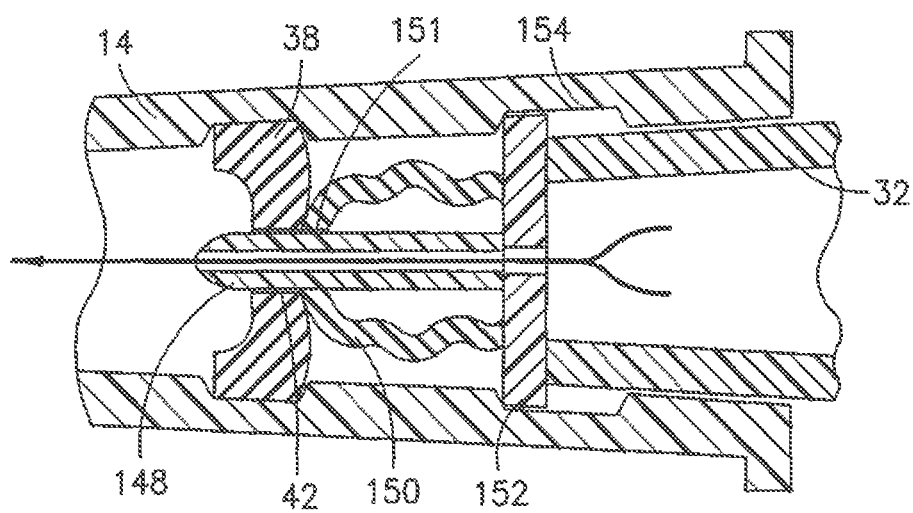
FIG. 20B is the catheter of FIG. 20A with a Luer connector inserted.
Figure 27:
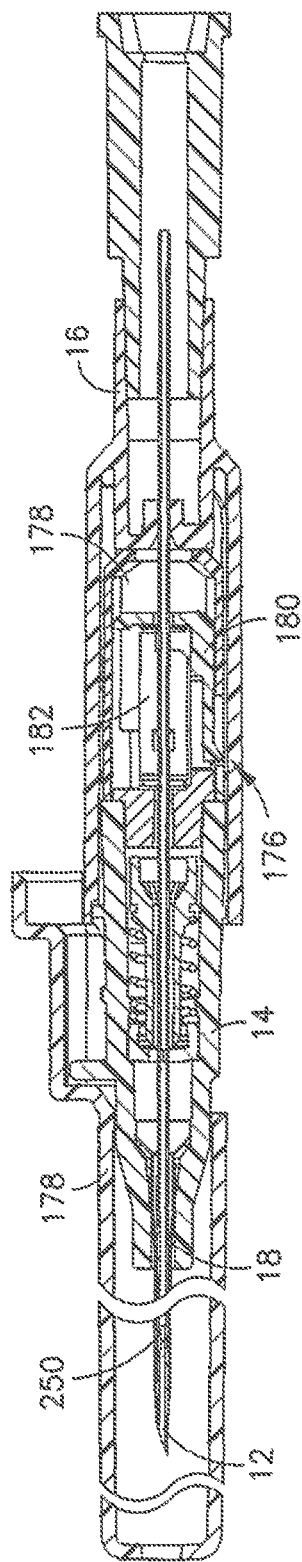
FIG. 27 is a sectional, side view of an exemplary catheter assembly having a needle tip shield.

FIGS. 20A-20B depict another alternative embodiment of a catheter hub 14 having an actuator 148 and a return or biasing member 150. The actuator 148 has an actuator barrel surrounding an internal passage. The actuator barrel has a first end that engages and opens the slits 42. The first end includes a rounded nose. A flange 152 for engaging the Luer connector 32 extends from the second end of the actuator barrel. The flange 152 is positioned in a slot 154 formed in the catheter hub. The engagement of the flange 152 with the slot 154 limits the axial movement of the actuator.

The biasing member in FIGS. 20A-20B is preferably an elastomer tube 150 that is positioned around the actuator barrel. However, the biasing member can also be, but is not limited to, rubber, silicone rubber, a thermal plastic, or a thermal plastic elastomer. In various exemplary embodiments, the elastomer tube 150 is molded to the actuator 148, for example in a multi-shot molding process, although other suitable mechanical and chemical connections may be used. The elastomer tube 150 has one or more slits 151 that open to allow passage of the actuator therethrough.

As a male Luer connector 32 is inserted, the actuator 148 is moved in the distal direction so that the elastomer tube 150 engages the septum 38. Further insertion of the Luer connector 32 causes the actuator barrel to pass through the slits in the elastomer tube 150 and compress the elastomer tube 150 as the actuator 148 moves through the septum 38. As the Luer connector 32 is removed, the elastomer tube 150 returns the actuator 148 to its initial position. In various exemplary embodiments, the septum 38 may assist in moving the actuator 148 in the proximal direction. The features of the exemplary actuator 148 and biasing member 150 depicted in FIGS. 20A-B may be combined with any features of the other exemplary embodiments disclosed herein as appropriate.

FIGS. 21A-21C depict another alternative embodiment of a catheter hub 14 having an actuator 152 and a return or biasing member 154. The actuator 152 has an actuator barrel surrounding an internal passage. The actuator barrel has a first end that engages and opens the slits 42. Extending from the second end of the actuator barrel is a cylindrical member for engaging the male Luer connector 32. The actuator is made from a rigid or semi-rigid material.

The biasing member of FIGS. 21A-21C preferably includes a compressible elastic sleeve 154. However, the biasing member can also be, but is not limited to, rubber, silicone rubber, a thermal plastic, or a thermal plastic elastomer. In various exemplary embodiments, the elastic sleeve 154 is unitarily formed with the septum 156. In a further embodiment, the septum 156 and biasing member 154 are unitarily formed with the actuator 152, for example by a multi-shot molding process that over-molds the septum 156 and biasing member 154 onto the actuator. In other alternative embodiments, the septum 156 and biasing member 154 may be connected, wrapped, or held together by an interference fit, for example with the cylindrical member pressing a portion of the elastic sleeve 154 against the inner surface of the catheter hub 14. The septum 156 and elastic sleeve 154 include a silicone material though other suitable materials may be used.

As best shown in FIG. 21B, the septum 156 has an oval configuration and is formed with a single slit 158. The slit 158 may be formed during molding or cut into the septum 156 after the molding operation. The septum 156 is configured so that the slit is in an open orientation in an unstressed condition. The septum 156 is fit into a slot or groove in the inner surface of the catheter hub 14. The groove is sized to compress the slit into a closed orientation, forming a fluid tight seal. As best shown in FIG. 21C, an elastomer 160 may be over-molded or assembled on the front edge of the conductor.

As a male Luer connector 32 is inserted, the actuator is moved in the distal direction, compressing the sleeve 154. Further insertion of the Luer connector 32 moves the actuator 152 through the septum 156, opening the slits 42. As the Luer connector 32 is removed, the sleeve 154 returns the actuator 152 to its initial position. The septum 38 may also assist in moving the actuator 152 in the proximal direction. The features of the exemplary actuator 152 and biasing member 154 depicted in FIGS. 21A-21C may be combined with features of the other exemplary embodiments disclosed herein as appropriate.

FIG. 22 depicts a side-port catheter hub 162 and FIGS. 23-26 depict various exemplary embodiments of an actuator 164 and a return or biasing member 166 used with a side-port catheter hub 162. The catheter hub 162 includes a channel and a side port 168 extending substantially orthogonal to the channel. A septum 170 forming a first valve is positioned in the channel. A side valve, for example a valve sleeve 172, is also positioned in the channel to form a second valve for the side port 168. The valve sleeve is an elastic member, for example a length of silicone or rubber tubing. The valve sleeve 172 is compression fit in the catheter hub. When fluid is introduced into the side port 168, the valve sleeve 172 deforms in the radial direction, permitting fluid to flow around the valve sleeve 172 and into the channel. Reference is made to U.S. Pat. No. 4,231,367, incorporated by reference herein, for a side port catheter with a valve sleeve of the type described herein.

FIGS. 23-26 depict an actuator 164 having an actuator barrel surrounding an internal passage. The actuator barrel has a first end that engages and opens the valve. A cylindrical or frusto-conical member extends from the second end of the actuator barrel to engage a male Luer connector. The biasing member 166 is depicted as a metal spring. However, the biasing member 166 can also be, but is not limited to, rubber, silicone rubber, a thermal plastic, or a thermal plastic elastomer.

In the exemplary configuration of FIG. 23, the septum 170 is positioned in catheter hub 162 distal to the side valve 172 and the biasing member 166 is positioned in the catheter hub 162 proximal to the side valve 172. The biasing member 166 is connected at a first end to the inner surface of the catheter hub 162 and at a second end to the actuator 164, for example by a pair of interference fits. The biasing member 160 may also abut the side valve 172 to limit distal movement.

In the exemplary configuration of FIG. 24, the septum 170 and the biasing member 166 are positioned distal to the side valve 172. The biasing member 166 is connected at a first end to the inner surface of the catheter hub 162 and at a second end to the actuator 164, for example by a pair of interference fits. The actuator 164 includes a flange 174 or one or more tabs extending radially from the actuator barrel to receive or abut the second end of the biasing member 166.

In the exemplary configuration of FIG. 25, the septum 170 and the biasing member 166 are positioned proximal to the side valve 172. The biasing member 166 is connected at a first end to the inner surface of the catheter hub 162 and at a second end to the actuator 164, for example by a pair of interference fits. The biasing member may also abut the septum 170 to limit distal movement.

In the exemplary configuration of FIG. 26, the septum 170 and the side valve 172 are unitarily formed. The biasing member 166 is connected at a first end to the inner surface of the catheter hub 162 and at a second end to the actuator 164, for example by a pair of interference fits. The biasing member 166 may also abut the side valve 172 to limit distal movement. The features of the exemplary actuator and biasing member depicted in FIGS. 22-26 may be combined with features of the other exemplary embodiments disclosed herein as appropriate.

Any of the catheters described herein can be used in combination with the features as depicted in FIGS. 27-37. The needle hub 14 extends around a needle tip shield 176 and retains a proximal end of a needle 12. A needle cover 178 initially covers the needle 12, the catheter tube 18, and at least a portion of the catheter hub 14. The needle cover 178 can connect to the catheter hub 14 or to the needle hub 16. The needle 12 initially extends through the needle tip shield 176 and the catheter hub 14. The flexible catheter tube 18 extends from the distal end of the catheter hub 14, with the needle 12 passing through the catheter tube 18. Initially, the needle 13 is inserted into a patient's vein. The catheter tube 18 is pushed along the needle 12 and into the vein following the needle 12. After the catheter tube 18 is inserted, the needle 12 is removed from the patient's vein and through the catheter hub 14. The needle tip shield 176 provides protection from being stuck by the needle 12 as it is retracted from the catheter hub.

In accordance with the exemplary embodiments depicted in FIGS. 27-36, the needle tip shield 176 includes an outer sleeve 178, an inner sleeve 180, and a resilient metal clip 182. The outer sleeve 178 connects to the catheter hub 14 and surrounds the inner sleeve 180, and the clip 182. The inner sleeve 180 is positioned in the outer sleeve 178 and is moveable in the axial direction. The clip 182 is connected to, and axially moveable with, the inner sleeve 180.

Figure 28:
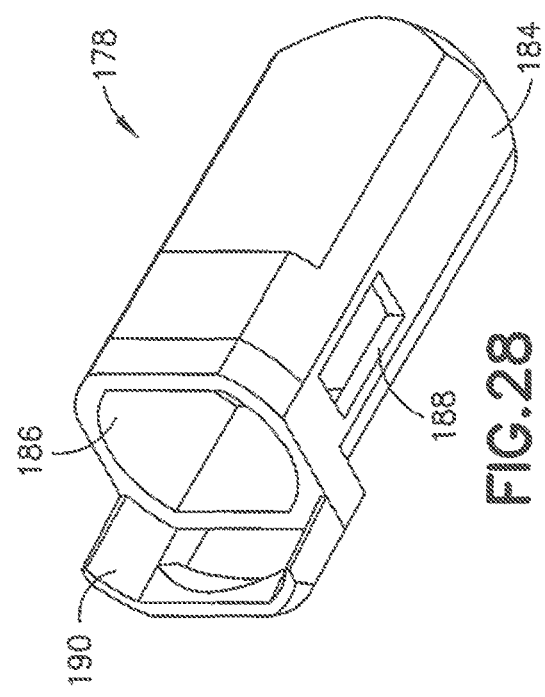
FIG. 28 is a perspective view of an exemplary outer sleeve of the needle tip shield.
Figure 29:
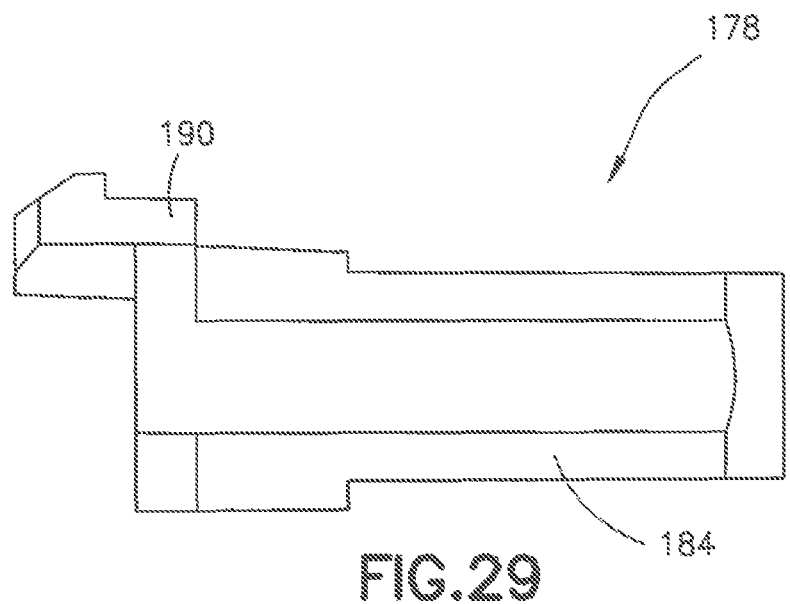
FIG. 29 is a side view of the outer sleeve of FIG. 28.
Figure 30:
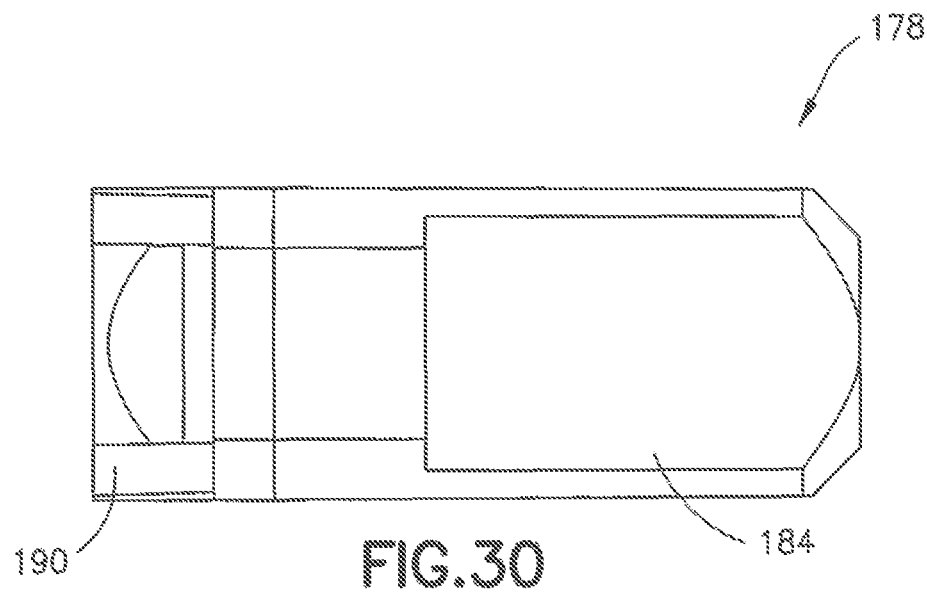
FIG. 30 is a top view of the outer sleeve of FIG. 28.

In accordance with the exemplary embodiments depicted in FIGS. 28-30, the outer sleeve 178 includes an outer surface 184, an inner surface 186, a channel bound by the inner surface 186, a proximal opening, and a distal opening. The outer surface 184 has an octagonal configuration with eight planar sides, although other curvilinear and/or rectilinear shapes may be used. The inner surface 186 has a planar top wall and a planar bottom wall connected by a pair of curved sides. A slot 188 extends through a wall of the outer sleeve 178.

A catch 190 extends from the outer surface to engage a protrusion on the catheter hub 14. In the exemplary embodiment, the catheter hub protrusion is a Luer connector receiving thread, for example a LUER-LOK® style of thread. The catch 190 has a front edge, a back edge, and a pair of side edges. An opening or depression is formed between the front edge and the back edge to receive the catheter hub protrusion. The opening allows the catch 190 to be formed with a clearance approximately equal to, or slightly greater than the height of the projection, allowing the catch 190 to engage the front, back, and/or sides of the connection while minimizing the amount of material and space needed. In various exemplary embodiments, the catch 190 is formed without the opening. The catch 190 resists premature release of the needle tip shield 176 from the catheter hub 14.

Figure 31:
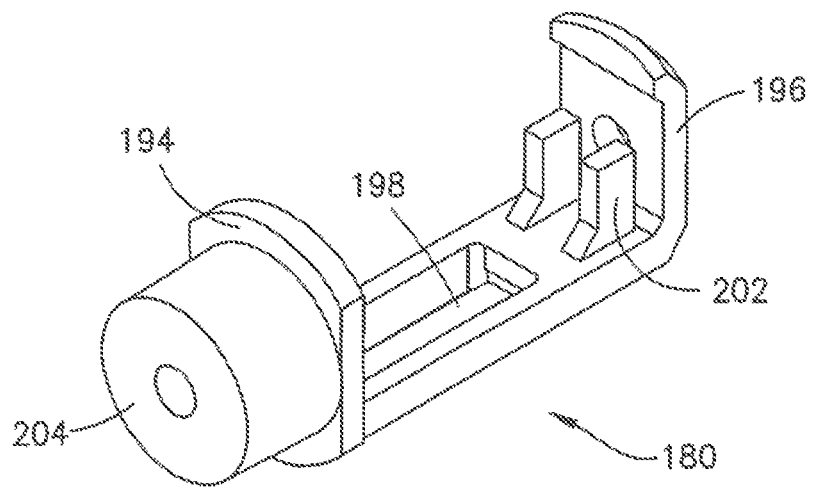
FIG. 31 is a top perspective view of an exemplary inner sleeve of the needle tip shield.
Figure 32:
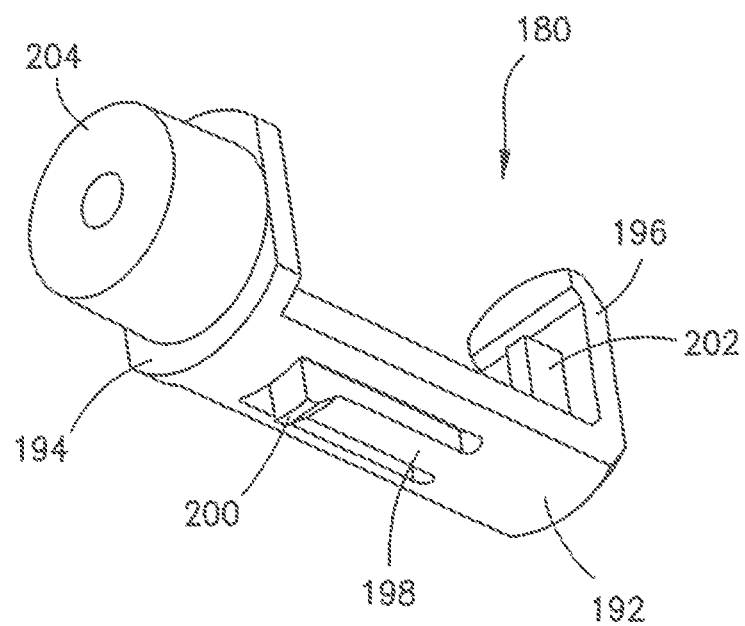
FIG. 32 is a bottom perspective view of the inner sleeve of FIG. 31.

In accordance with the exemplary embodiments depicted in FIGS. 31 and 32, the inner sleeve 180 includes a base 192, a distal side 194, and a proximal side 196. A resilient arm 198 and a tab 200 extend from an outer surface of the base 192. The resilient arm 198 and the tab 200 engage the slot 188 in the outer sleeve 184. One or more clip retainers 202 extend from an inner surface of the base 192. The clip is positioned between the clip retainers 202 and the proximal side 196. An opposing member 204 extends from the distal side 194 in the distal direction. The opposing member 204 is tubular and configured to be inserted into the catheter hub 14. The proximal side 194, distal side 196, and opposing member 204 each have an opening for receiving the needle 12.

Figure 33:
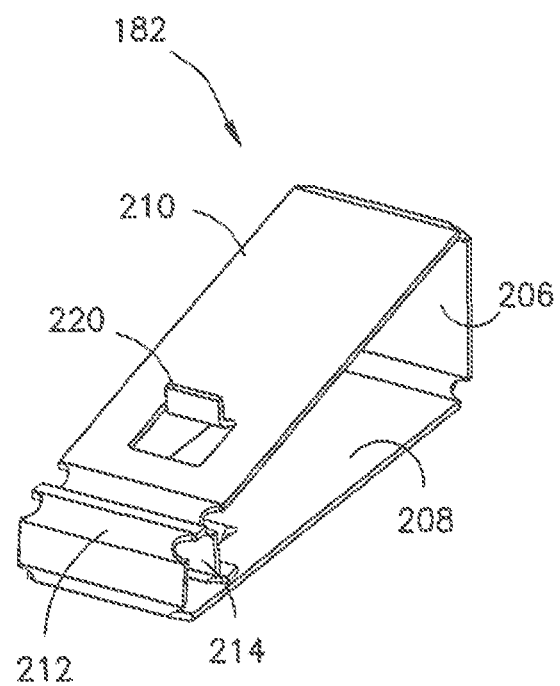
FIG. 33 is a top perspective view of a needle tip shield clip.
Figure 34:
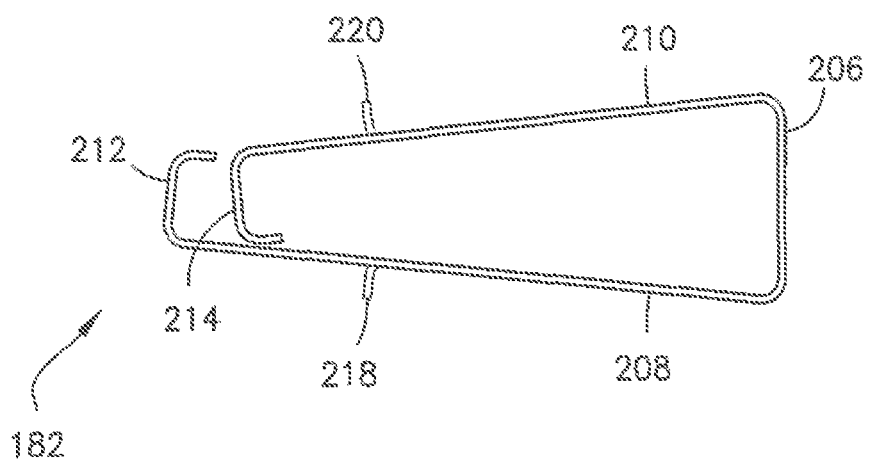
FIG. 34 is a side view of the clip of FIG. 33.

In accordance with the exemplary embodiments depicted in FIGS. 33 and 34, the resilient metal clip 182 includes a base 206 having an opening for receiving the needle 12, a first arm 208, and a second arm 210 extending from the base 206. The first arm 208 extends further in the axial direction than the second arm 210. The first arm 208 has a first hook 212 and the second arm 210 has a second hook 214. A first tab 218 is formed in the first arm 208 and a second tab 220 is formed in the second arm 210.

Initially, the needle 12 passes through the outer sleeve 178, the inner sleeve 178, and the clip 182. The needle 12 biases the clip 182 into an open position, so that the first and second hooks 212, 214 are resting along the needle shaft. In the assembled position, the catch 190 engages the Luer threads on the outer surface of the catheter hub 14 and the opposing member 204 extends into the proximal opening of the catheter hub 14. In order to remove the catch 190 from the catheter hub 14, the outer sleeve 178 of the needle tip shield 176 must be raised so that the catch 190 can slide over the Luer threads. Raising the needle tip shield 176 relative to the catheter hub 14, however, is initially prevented by the opposing member 204 extending into the catheter hub 14.

Figure 37:
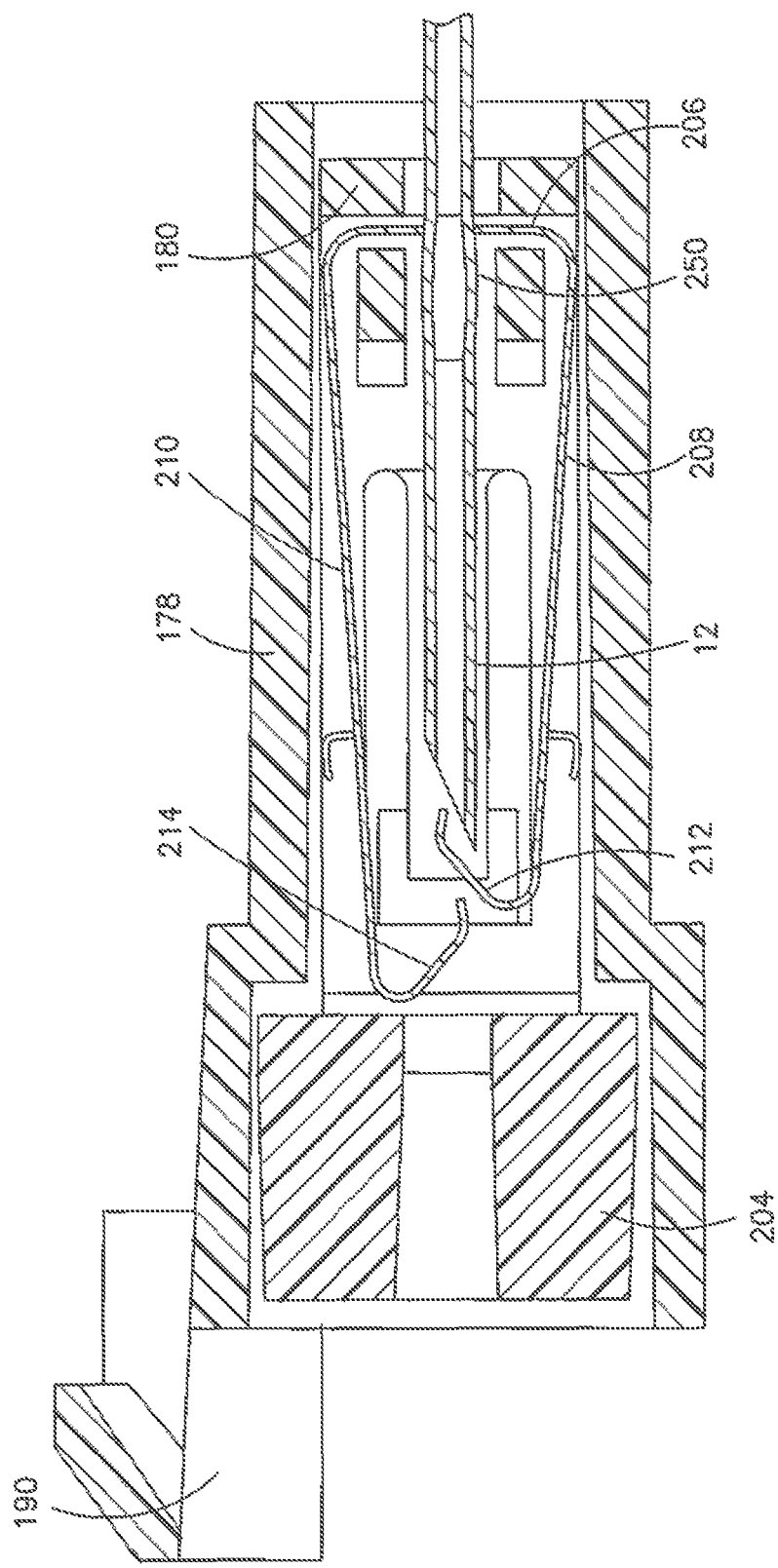
FIG. 37 is a sectional, side view of the needle tip shield with the clip in a closed position.

As the needle 12 is withdrawn from the catheter hub 14, the tip of the needle 12 clears the first and second hooks 212, 214, as illustrated in FIG. 37, causing the first and second arms 208, 210 to close and the first and second hooks 212, 214 to surround the tip of the needle 12. As such, the clip 182 is in a closed position where the distal tip of the needle 12 is blocked. This needle protection mechanism, via the clip 182, operates passively (automatically) when the needle 12 is removed from the catheter hub 14 because user actuation is not required to initiate needle protection.

As the needle 12 is pulled further, the shaft of the needle slides through the needle tip shield 176 until a deformation, for example a crimp or protrusion 250 formed near the distal end of the needle 12 to increase its diameter in at least one direction, engages the clip base 206. The opening in the clip base 206 is sized to interact with the deformation such that the needle shaft passes through, but not the deformation. Accordingly, a sharp distal tip area, which includes the sharp distal tip and the deformation of the needle 12, for example, is enclosed by the clip 182.

Further movement of the needle 12 results in the inner sleeve 180 being drawn further into the outer sleeve 178, removing the opposing member 204 from the catheter hub 14. When the opposing member 204 is withdrawn from the catheter hub 14, the catch 190 may be removed from the Luer thread protrusion and the needle tip shield 176, needle 12, and needle hub 16 separated from the catheter 10.

Figure 35:
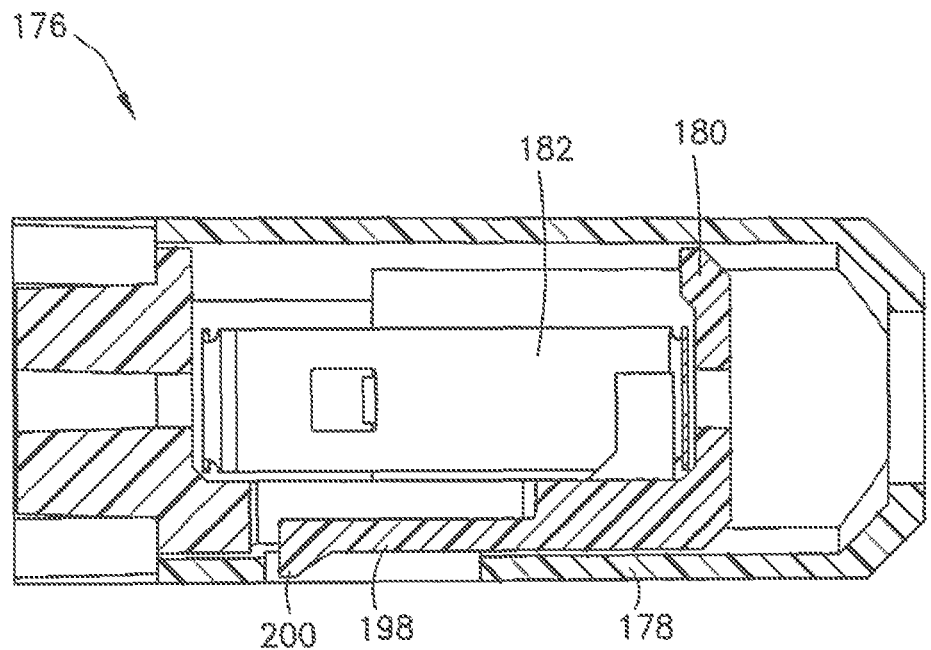
FIG. 35 is a sectional, side view of the needle tip shield of FIG. 27.

FIG. 35 shows the arm 198 and tab 200 of the inner sleeve 180 positioned in the slot 188 of the outer sleeve 178. After the tip of the needle 12 passes the first and second hooks 212, 214 and the first and second arms 208, 210 move into a closed orientation, the tab 200 can engage the slot 188 to resist separation of the inner sleeve 180 and the outer sleeve 178 and possible exposure of the needle 12.

Figure 36:
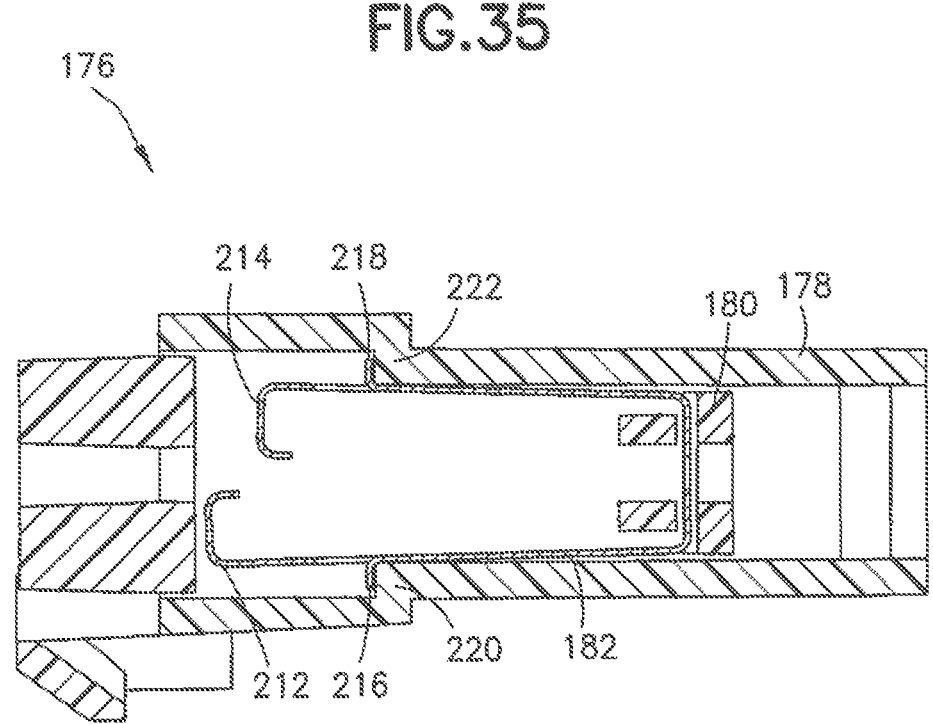
FIG. 36 is another sectional, side view of the needle tip shield of FIG. 27.

FIG. 36 shows the first and second tabs 216, 218 engaging a first shoulder 220 and a second shoulder 222 on the outer sleeve. The tabs 220, 222 help prevent the clip 182 and the inner sleeve 180 from unintentionally sliding into the outer sleeve 178, for example during shipping. The needle 12 biases the first and second arms 208, 210 into an open position so that the tabs 216, 218 engage the outer sleeve 178.

Any of the various exemplary embodiments discussed herein may include an antimicrobial system, such that one or more antimicrobial agents or coatings may be incorporated or applied to any of the components of the catheter discussed herein. For example, the spring may be coated with a UV curable antimicrobial adhesive coating. The coating may be applied spraying, batch tumbling, or during formation of the spring windings. A suitable coating is described in U.S. Pat. No. 8,691,887, the disclosure of which is incorporated by reference. Antimicrobial agents suitable for use in this is type of application included, chlorhexidine gluconate, chlorhexidine diacetate, chloroxylenol, triclosan, hexetidine, and may be included in a actuator lubricant applied to assist in easy penetration and opening of the septum, and return of the actuator to the closed position after Luer connector disengagement.

Figure 38:
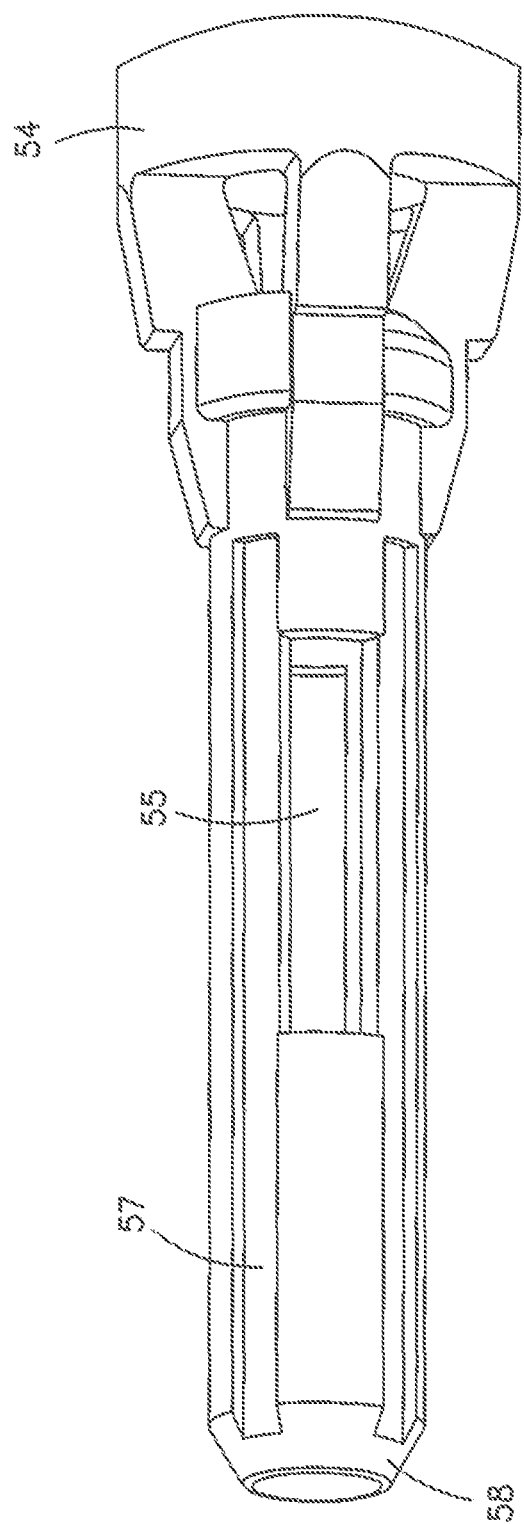
FIG. 38 illustrates a right side view of another exemplary embodiment of an actuator.

FIG. 38 illustrates an exemplary embodiment of an actuator 54. The actuator 54 can be used in any of the embodiments disclosed herein. The actuator 54 includes a nose 58 that reduces friction when the actuator 54 penetrates into a septum 38 of a catheter hub assembly. The actuator 54 further includes openings 55 that extend through the actuator 54 in a direction perpendicular to a centerline of the actuator 54. For example, the actuator 54 can include two rectangular shaped openings 55, although more or less are contemplated.

The actuator 54 also includes a plurality of grooves 57 that extend axially along the distal portion of an outer surface of the actuator 54 in a plane parallel to the centerline of the actuator 54. For example, four grooves 57, substantially radially equidistant from each other, can be present along an external surface of the distal portion of the actuator 54, although more or less grooves 57 are contemplated. The grooves 57 can be of varying depths into the actuator 54. The grooves 57 are different from the openings 55 because the grooves 57 do not extend completely through the thickness of the actuator 54.

The openings 55 and the grooves 57 advantageously provide increased area for the fluid to move inside the catheter hub assembly. The increased area advantageously allows for fluid flushing and to prevent coagulation of fluid in the proximal and distal ends of the septum. Additionally, the openings 55 and the plurality of grooves 57 advantageously minimize the stagnation of fluid and allow for greater mixing. The grooves 57 further prevent the septum from sealing on an outside surface of the actuator during operation. By not forming a sealing interface, the fluid is permitted to leak through the septum via the grooves 57 and provide additional flushing.

Figure 39A:
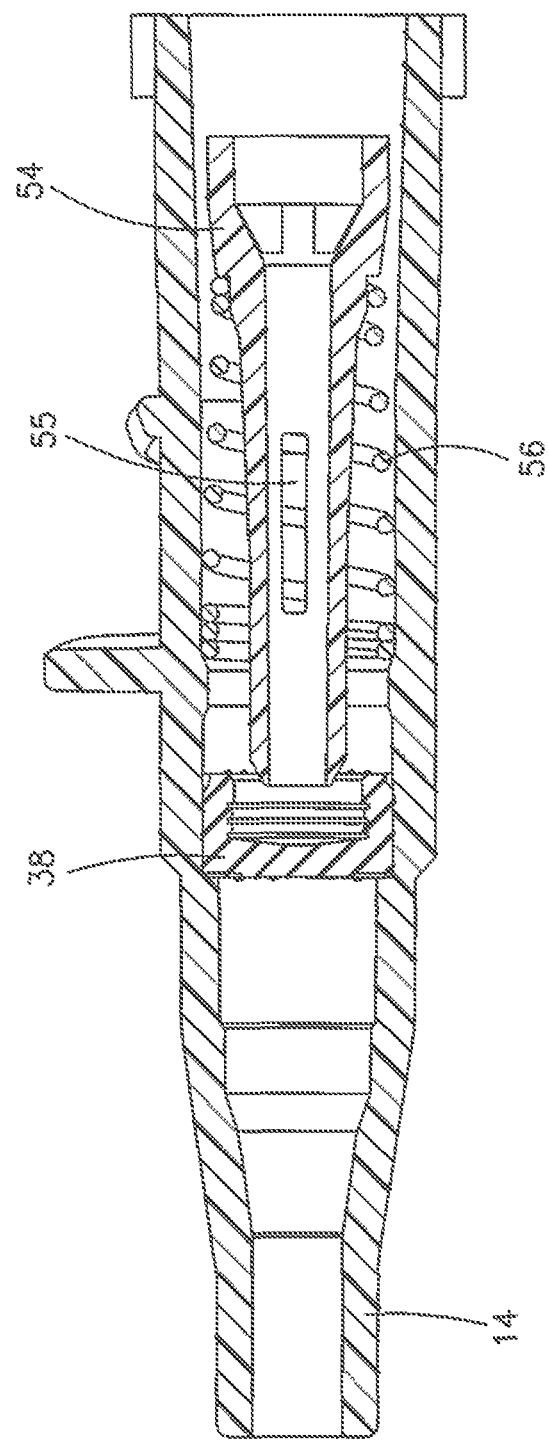
FIG. 39A illustrates a sectional view of the actuator of FIG. 38 in a catheter hub assembly.

FIG. 39A illustrates the actuator 54 of FIG. 38 in the catheter hub assembly. Similar to the embodiments described above, the catheter hub assembly further includes a catheter hub 14, a septum 38 and a biasing member 56. As illustrated, the openings 55 and the grooves 57 of the actuator 54 provide more area for fluid flow inside the catheter hub 14, thus achieving the advantages described above.

Figure 39B:
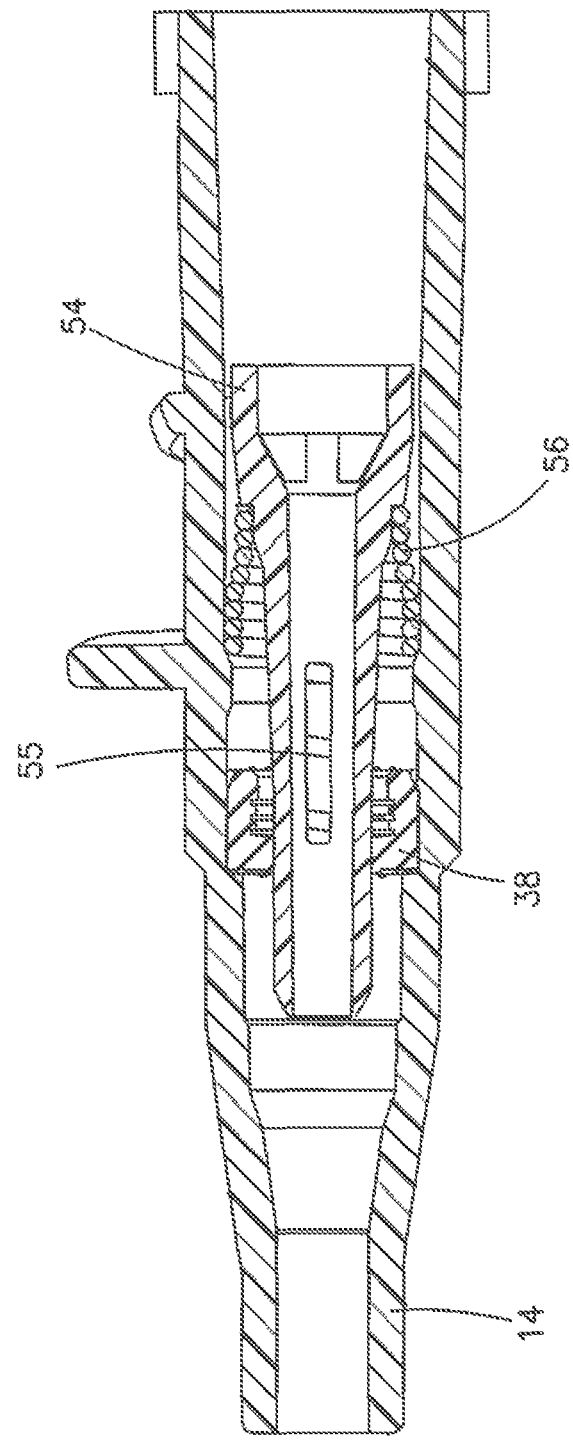
FIG. 39B illustrates a sectional view of the catheter hub assembly of FIG. 39A when penetrating a septum.
Figure 39C:
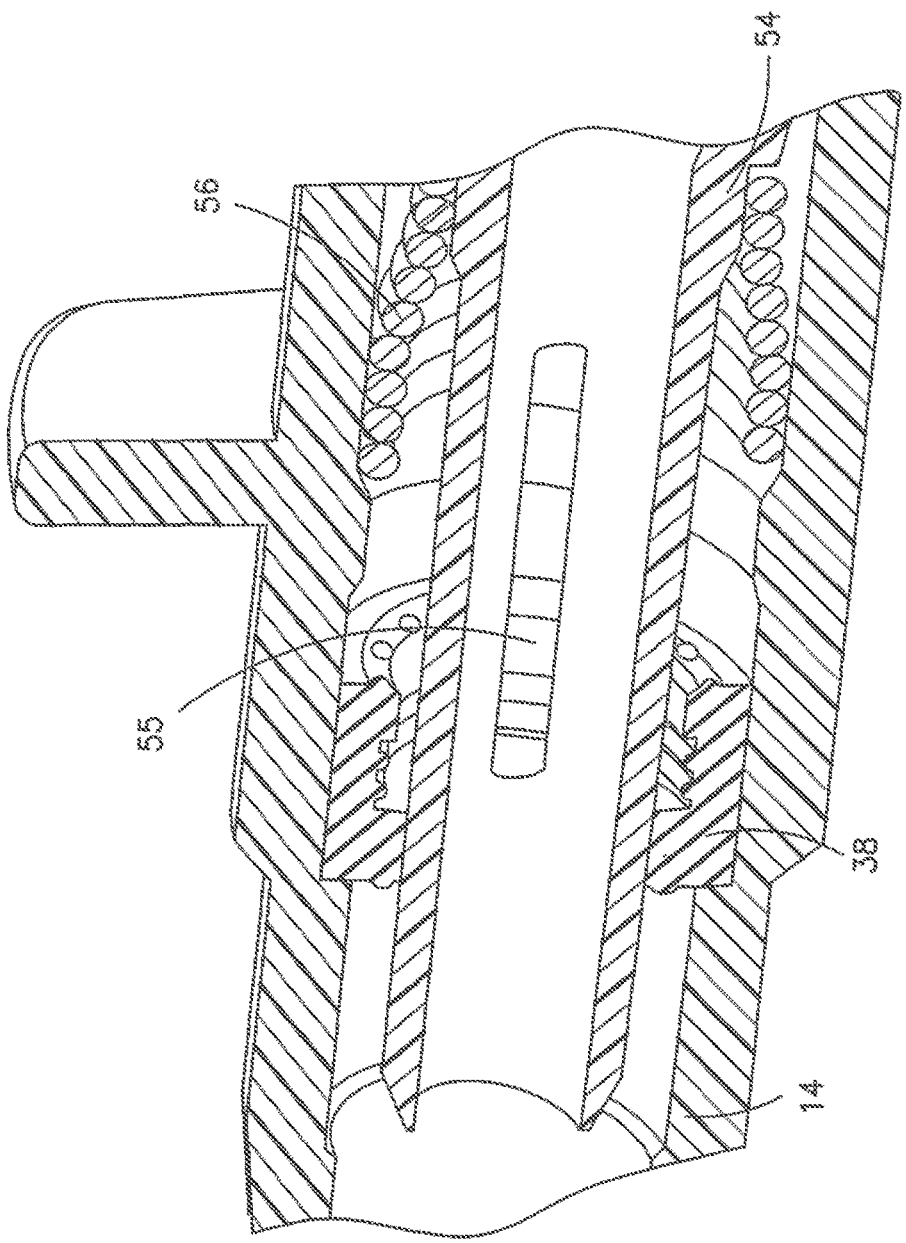
FIG. 39C illustrates a left perspective sectional view of the catheter hub assembly of FIG. 39A when penetrating a septum.

FIGS. 39B and 39C illustrate the catheter hub assembly when the biasing member 56 is compressed and the actuator 54 penetrates the septum 38. The catheter hub assembly may be configured such that the openings 55 and/or the grooves 57 of the actuator 54 optionally penetrate the septum 38. In this embodiment, the openings 55 in the actuator 54 do not penetrate the septum 38. However, the grooves 57 in the actuator 54 penetrate the septum 38. This configuration allows for increased fluid flow from the proximal end to the distal end of the septum 38 through the grooves 57, in addition to the advantages described above. After operation of the catheter assembly is complete, the actuator 54 is retracted from the septum 38 via the force exerted by the biasing member 56. The catheter assembly is configured for multiple uses upon depression of the actuator 54. The features described in this embodiment, such as the actuator, can be used in combination with the features described throughout this application.

Figure 40A:
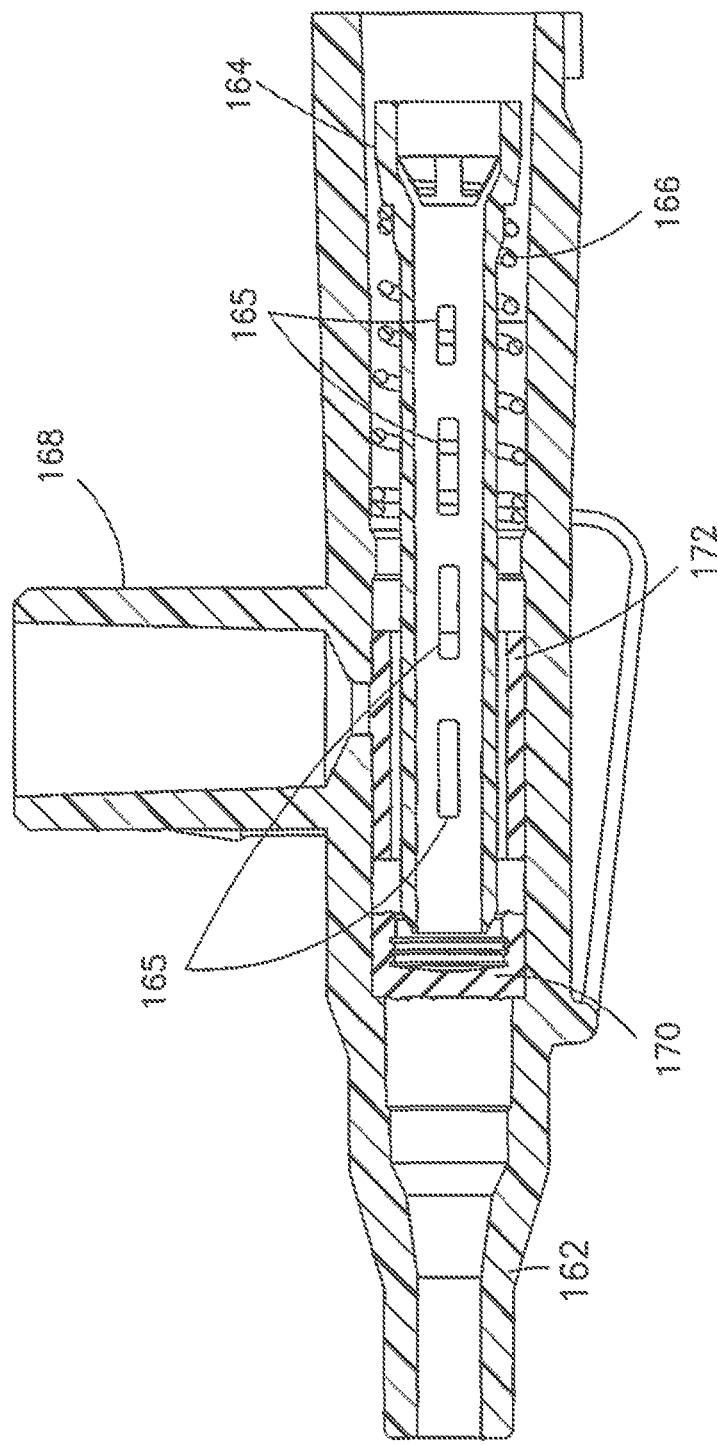
FIG. 40A illustrates a sectional view of another exemplary embodiment of a catheter hub assembly.

FIG. 40A illustrates another embodiment of an actuator 164 in a catheter hub assembly. The catheter hub assembly includes a catheter hub 162 having a side port 168. The side port 168 provides secondary access to the fluid flow in the catheter hub 162. The intersection of the main bore of the catheter hub 162 and the side port 168 includes a sleeve 172. The sleeve 172 provides selective fluid communication between the side port 168 and the catheter hub 162. Specifically, when sufficient fluid pressure is applied through the side port 168, the sleeve 172 compresses. The compression of the sleeve 172 allows for fluid to enter the catheter hub 162. The catheter hub assembly further includes a septum 170 and a biasing member 166 that provides tension to the actuator 164.

The actuator 164 includes a plurality of openings 165 that extend through the actuator 164 in a similar manner as described above. The actuator 164 includes two rows of four openings 165 having different sizes and spacing, although various quantities, sizes and spacing of the openings 165 are contemplated. As illustrated, the openings 165 provide more area for fluid flow inside the catheter hub 14, thus achieving similar advantages described above with respect to FIGS. 38-39C.

FIGS. 40B and 40C illustrate the catheter hub assembly when the actuator 164 penetrates the septum 170 and compresses the biasing member 166. The catheter hub assembly is configured such that the openings 165 of the actuator 164 optionally penetrate the septum 170. In this embodiment, the openings 165 in the actuator 164 do not penetrate the septum 170. This configuration allows for increased fluid flow between the side port 168 and the catheter hub 162 at the proximal end of the septum 38, in addition to the advantages described above. If the openings 165 in the actuator 164 penetrate the septum 170, increased mixing of fluid would also take place at a distal end of the septum 38.

When operation of the catheter assembly is complete, the actuator 164 is retracted from the septum 170 via the force exerted by the biasing member 166. The catheter assembly is configured for multiple uses upon depression of the actuator 164. The features described in this embodiment, such as the actuator, can be used in combination with the features described throughout this application.

FIG. 41 illustrates a cross sectional view of another exemplary embodiment of a catheter assembly 300 with a different type of needle protection mechanism, in this case one that houses the entire needle within a protective tube or barrel, rather than shielding only the needle tip. The catheter assembly 300 employs active (rather than passive or automatic) needle protection because user activation, via depression of an activation button 308, is required to initiate needle protection. However, both active and passive needle protection are within the scope of the present invention.

Operation of the catheter assembly 300 is described as follows. The catheter 302 and the needle 304 are inserted into a vein of a patient. When the needle 304 and catheter 302 are securely disposed, the activation button 308 is depressed. Upon depression of the activation button 308, as illustrated in FIG. 42, an inner needle hub or housing 312 is disengaged from a wall (not shown) of the activation button 308. The needle 304 then retracts into a catheter hub 306. A spring 310 surrounding the inner needle housing 312 is released by the activation button 308 which causes the inner needle housing 312 to travel to the opposite end of the outer needle housing 314. Thus, the needle 304 is now in a retracted position where the complete needle 304 (including its sharp distal tip) is retained in the outer needle housing 314. The inner needle housing 312 holding the needle 304 is retained in the outer needle housing 314 via the force exerted by the spring 310. Accordingly, the combination of the inner needle housing 312, the outer needle housing 314 and the spring 310 is an exemplary needle protection member.

More information regarding the active needle protection mechanism used in this embodiment can be found in U.S. Pat. Nos. 4,747,831, 5,501,675, 5,575,777, 5,700,250, 5,702,367, 5,830,190, 5,911,705, 8,361,038, 8,388,583, 8,469,928, 8,864,715, and 8,932,259, the contents of which are hereby incorporated by reference. The features described in this embodiment, including the active needle protection features, can be used in combination with the catheter assemblies described throughout this application.

FIG. 43 illustrates a cross sectional view of another exemplary embodiment of a catheter assembly 400 with a different type of needle protection mechanism, in this case one like that of FIGS. 27-37 that shields only the needle tip. The needle protection mechanism disclosed in the catheter assembly 400 operates passively (automatically) when the needle 402 is removed from the catheter hub 406 because user actuation is not required to initiate needle protection. Operation of the catheter assembly 400 is described as follows. The catheter 404 and the needle 402 are inserted into a vein of a patient. When the needle 402 and catheter 404 are securely disposed, the needle 402 is withdrawn by a user.

The needle 402 is withdrawn from the catheter 404 when the user pulls the outer needle housing or hub 414. The needle 402 subsequently retracts into the catheter hub 406 and a sharp distal tip of the needle 402 ultimately enters into the inner needle housing 408. Prior to the distal tip of the needle 402 entering into the inner needle housing 408, the needle 402 contacts and biases a longitudinal metal clip 412 into an open position. The longitudinal clip 412 can be, for example, a leaf spring that extends and compresses in a longitudinal direction. When the distal tip of the needle 402 sufficiently enters into the inner needle housing 408, as illustrated in FIG. 44, the clip 412 extends into the inner needle housing 408 towards a centerline of the needle 402. Accordingly, the clip 412 is no longer biased and enters into a closed position where the distal tip of the needle 402 is blocked.

The needle 402 further includes a deformation 403 adjacent to its distal tip. In at least one direction, the diameter of the deformation 403 is greater than the diameter of the remainder of the needle 402. The deformation 403 prevents the needle 402 from exiting the inner needle housing 408 during retraction of the needle 402. Specifically, when the distal tip of the needle 402 is in the inner needle housing 408, the deformation 403 contacts a rear wall of the inner needle housing 408 and prevents the needle 402 from exiting the inner needle housing 408. Thus, the distal tip and the deformation 403 of the needle 402 are enclosed in the inner needle housing 408. The clip 412, needle 402, inner needle housing 408 and outer needle housing 414 are an exemplary needle protection member.

As illustrated in FIG. 45, when the user continues to pull the outer needle housing 414, the inner needle housing 408 and the catheter hub 406 disengage and separate. Specifically, a boss 410 of the inner needle housing 408 disengages from a bore in the catheter hub 406.

After the needle 402 is used, the inner needle housing 408 enclosing the tip of the needle 402 and the outer needle housing 414 are discarded. The catheter hub assembly can be subsequently used. Specifically, the user can engage a Luer connector 416 with the catheter hub 406 to cause the actuator to open or penetrate the septum and establish fluid communication.

More information regarding the needle tip protection mechanism used in this embodiment can be found in U.S. Pat. Nos. 5,215,528 and 5,558,651, the contents of which are hereby incorporated by reference. The features described in this embodiment, including the passive needle protection, can be used in combination with the catheters described throughout this application.

Figure 46:
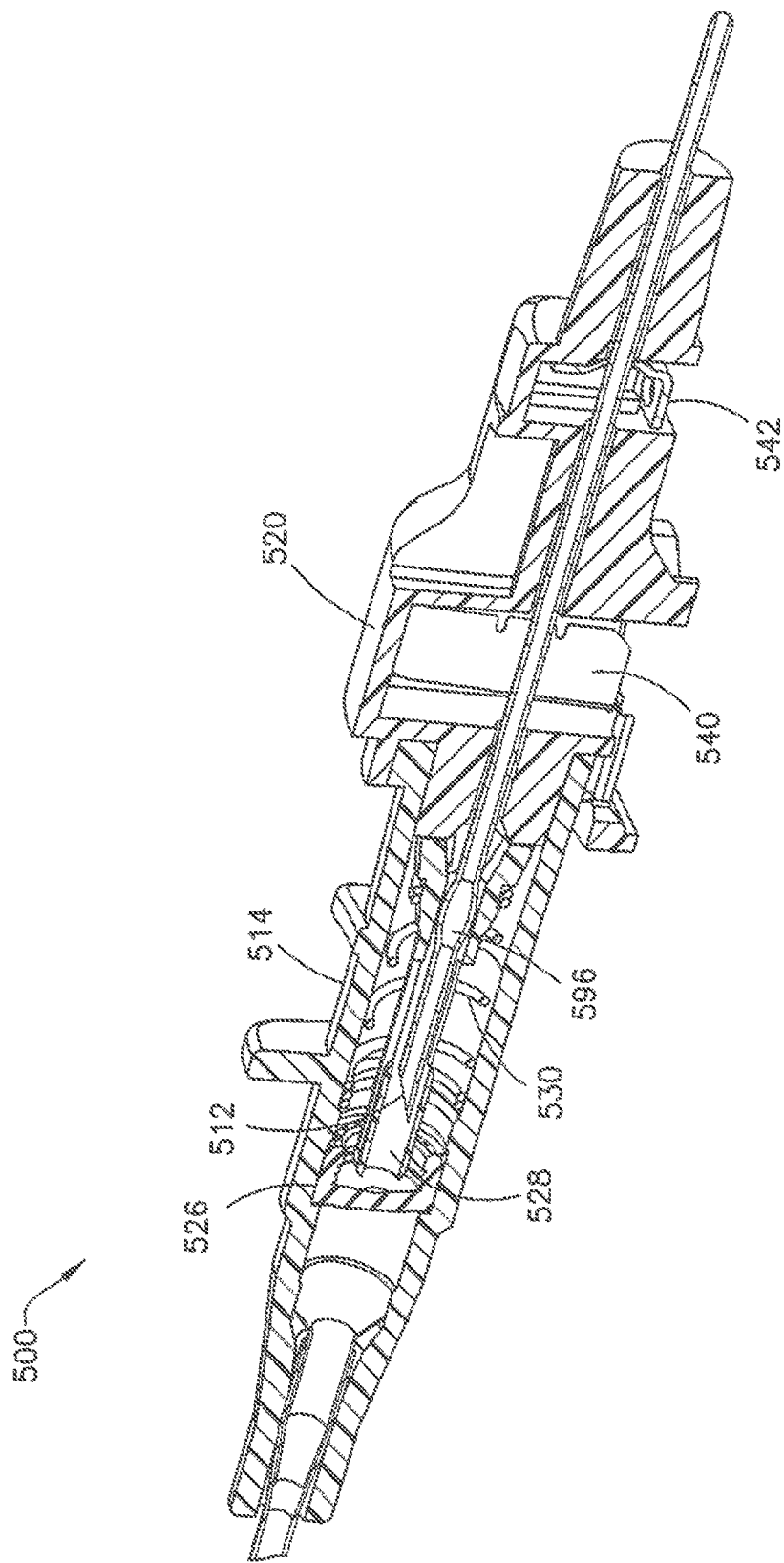
FIG. 46 illustrates a sectional view of another exemplary embodiment of a catheter assembly in the needle extended position.

FIG. 46 illustrates a cross sectional view of another exemplary embodiment of a catheter assembly 500 with a needle tip shield. The needle protection mechanism disclosed in the catheter assembly 500 operates passively (automatically) when the needle 512 is removed from the catheter hub 514 because user actuation is not required to initiate needle protection. Operation of the catheter assembly 500 is described as follows. During operation, a needle 512 extends through an actuator 528 that pierces a septum 526 in a catheter hub 514, as similarly described in the embodiments above. A V-clip 540, located in a needle tip shield 520, is biased by the needle 512 into an open position (the V-clip 540 is collapsed) to allow the needle 512 to pass beyond the V-clip 540. The V-clip 540 comprises a resilient metal clip. After operation of the catheter assembly 500, the biasing member 530 retracts the actuator 528 into the catheter hub 514.

Figure 47:
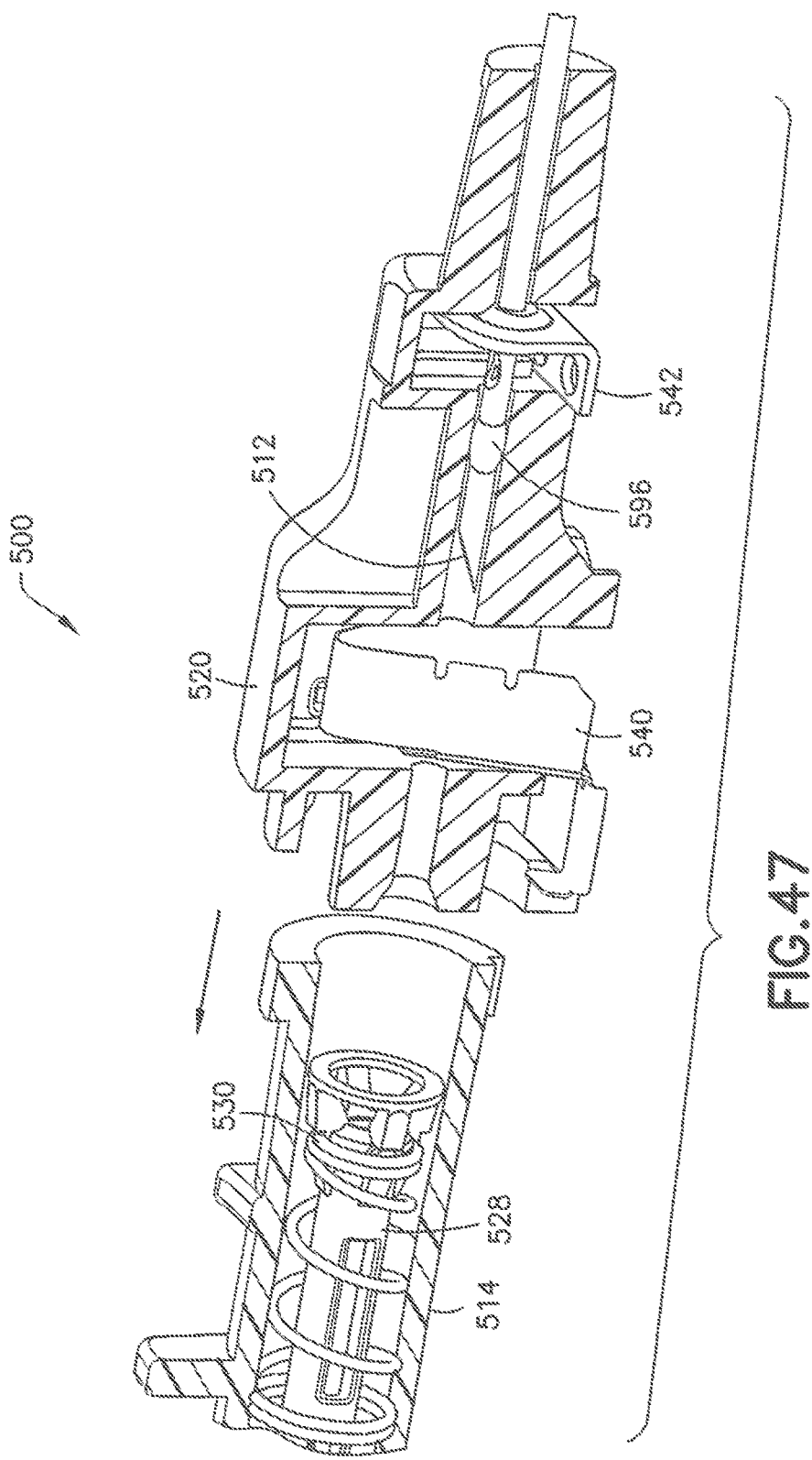
FIG. 47 illustrates a sectional view of the catheter hub assembly and the needle hub assembly of FIG. 46 in the needle retracted position.

FIG. 47 illustrates a cross sectional view of the catheter assembly 500 when the needle 512 is in a retracted position. When a distal tip of the needle 512 enters into the needle tip shield 520 and is positioned on the proximal end of the V-clip 540, the V-clip 540 is no longer biased. Rather, the V-clip 540 expands in the needle tip shield 520 into a closed position (the V-clip is expanded) to prevent the needle 512 from traveling beyond the V-clip 540. The expansion of the V-clip 540 in the needle tip shield 520 forms one or more barriers (as described below) that prevent the distal tip of the needle 512 from exiting the needle tip shield 520.

The needle tip shield 520 includes a metal washer 542 and the needle 512 includes a deformation 596 adjacent to the distal tip of the needle 512. In at least one radial direction, the diameter of the deformation is greater than the diameter of the remainder of the needle 512. In at least one radial direction, the diameter of the deformation 596 is bigger than a through-hole in the washer 542 where the needle 512 travels. Thus, the deformation 596 prevents the needle 512 from exiting the washer 542 during needle 512 retraction. Accordingly, when the needle 512 is in the retracted position, the distal tip of the needle 512 and the deformation 596 are enclosed via the washer 542 and the barrier of the V-clip 540.

Figure 48:
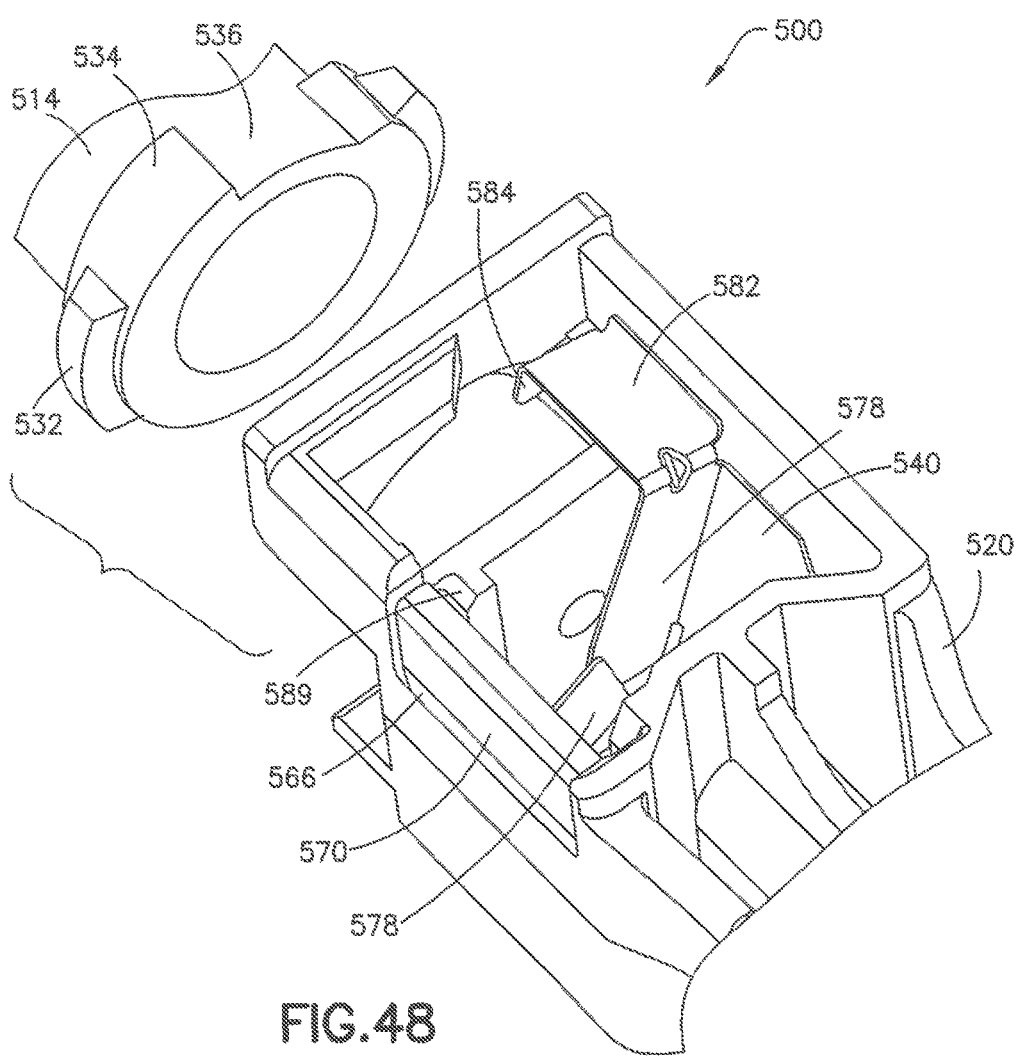
FIG. 48 illustrates a bottom plan view of the catheter hub assembly and the needle hub assembly of FIG. 46 in the needle retracted position.

FIG. 48 illustrates a bottom plan view of the catheter hub assembly and the needle hub assembly when the needle is retracted. The catheter hub 514 includes a collar 534 having a collar opening 536 and Luer threads 532. When the needle 512 biases the V-clip 540 into an open position as described above, a latch 584 that is connected to a foot 582 of the V-clip 540 engages the collar 534. The V-clip 540 being engaged with the collar 534 keeps the catheter hub 514 and the needle tip shield 520 connected.

On the other hand, when the needle 512 is in the retracted position and no longer biases the V-clip 540, the V-clip 540 moves to the closed position. In the closed position, the latch 584 and the foot 582 of the V-clip 540 move into axial alignment with the collar opening 536. The collar opening 536 thus allows the catheter hub 514 to disengage from the needle tip shield 520.

Additionally, when the V-clip 540 moves to the closed position, a barrier 578 in the V-clip 540 prevents the distal tip of the needle 512 from exiting the needle tip shield 520. Preferably, the barrier 578 includes two barriers although more or less are contemplated. The combination of the V-clip 540 and the washer 542 is an exemplary needle protection member.

The V-clip 540 further includes an outer wall 570 and a spade 566 that are configured to attach the V-clip 540 to an outer wall of the needle tip shield 520. The outer wall of the needle tip shield 520 includes projections 589 that secure the V-clip 540 by creating friction between the V-clip 540 and the needle tip shield 520. This configuration advantageously secures the V-clip 540 to the needle tip shield 520 and avoids the use of an outer housing for mounting. Accordingly, the width of the needle tip shield 520 is advantageously reduced.

Upon separation of the catheter hub assembly and the needle tip shield 520, the catheter hub assembly can be subsequently used as a multi-use blood control apparatus. Specifically, the actuator 528 can be engaged multiple times through the use of the Luer threads 532 in a similar manner as described in the above embodiments.

More information regarding the needle tip protection mechanism used in this embodiment can be found in U.S. Pat. Nos. 6,749,588, 7,604,616 and U.S. Patent Application Publication No. 2014/0364809, the contents of which are hereby incorporated by reference. The features described in this embodiment, including the passive needle protection features, can be used in combination with the features described throughout this application.

Needle protection members other than those disclosed herein may be used in the present invention. These may be needle tip shields as exemplified by the embodiments of FIGS. 27-37, 43-45, and 46-48, needle-enclosing tubes or barrels as exemplified by the embodiment of FIGS. 41-42, or other arrangements. They may operate passively (automatically) when the needle is removed from the catheter hub as in the embodiments of FIGS. 27-37, 43-45 and 46-48, or they may require active user actuation as in the embodiments of FIGS. 41-42.

Figure 49:
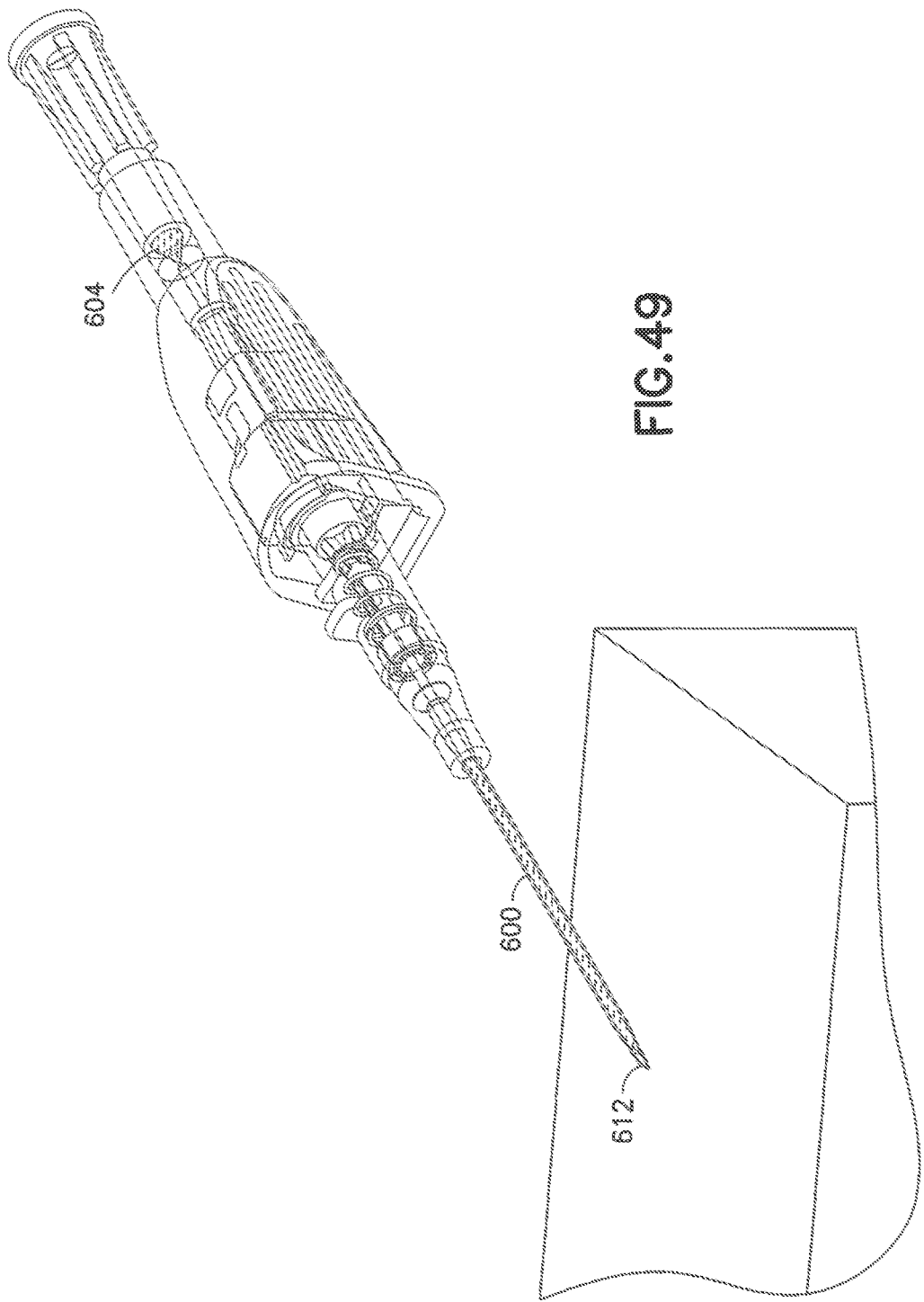
FIG. 49 illustrates an exemplary embodiment of a blood flashback feature of a catheter assembly.
Figure 50:
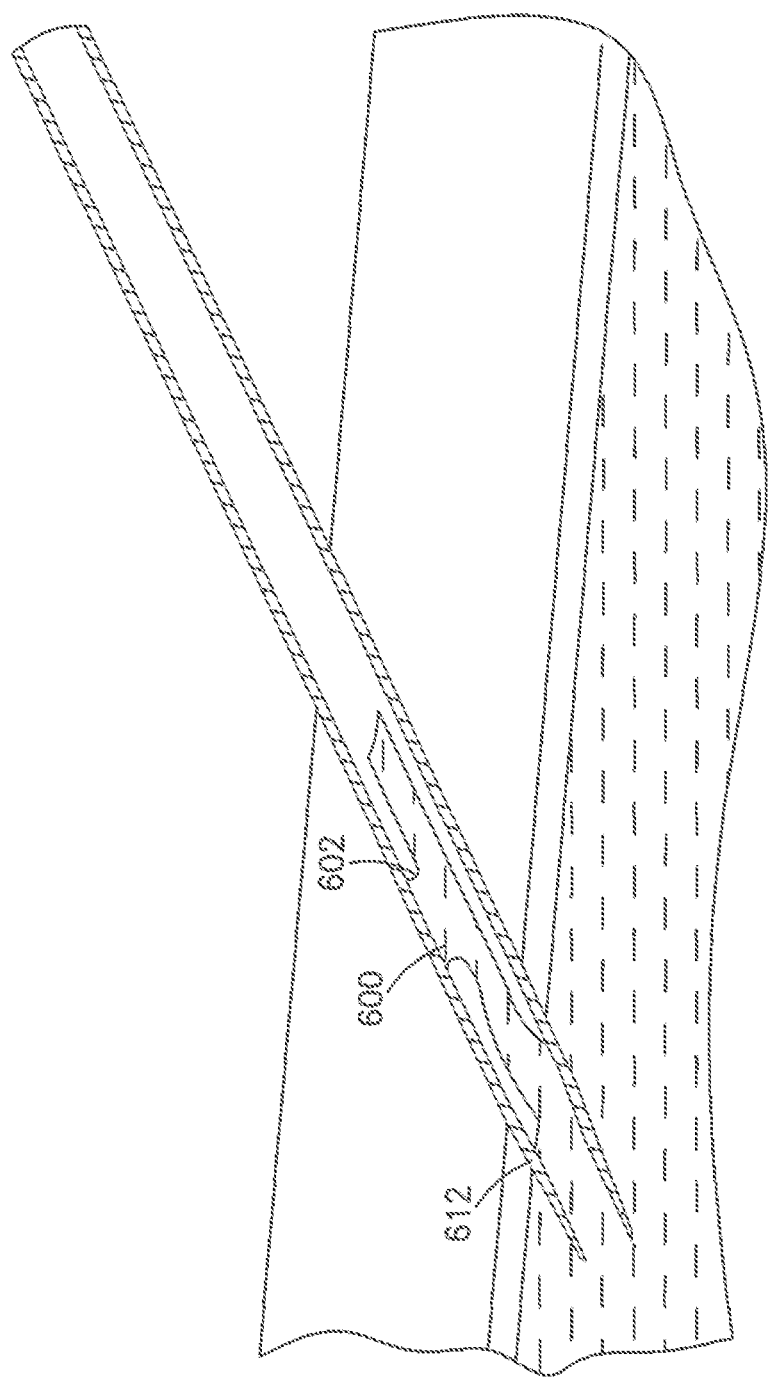
FIG. 50 illustrates a needle in the catheter assembly of FIG. 49.
Figure 51:
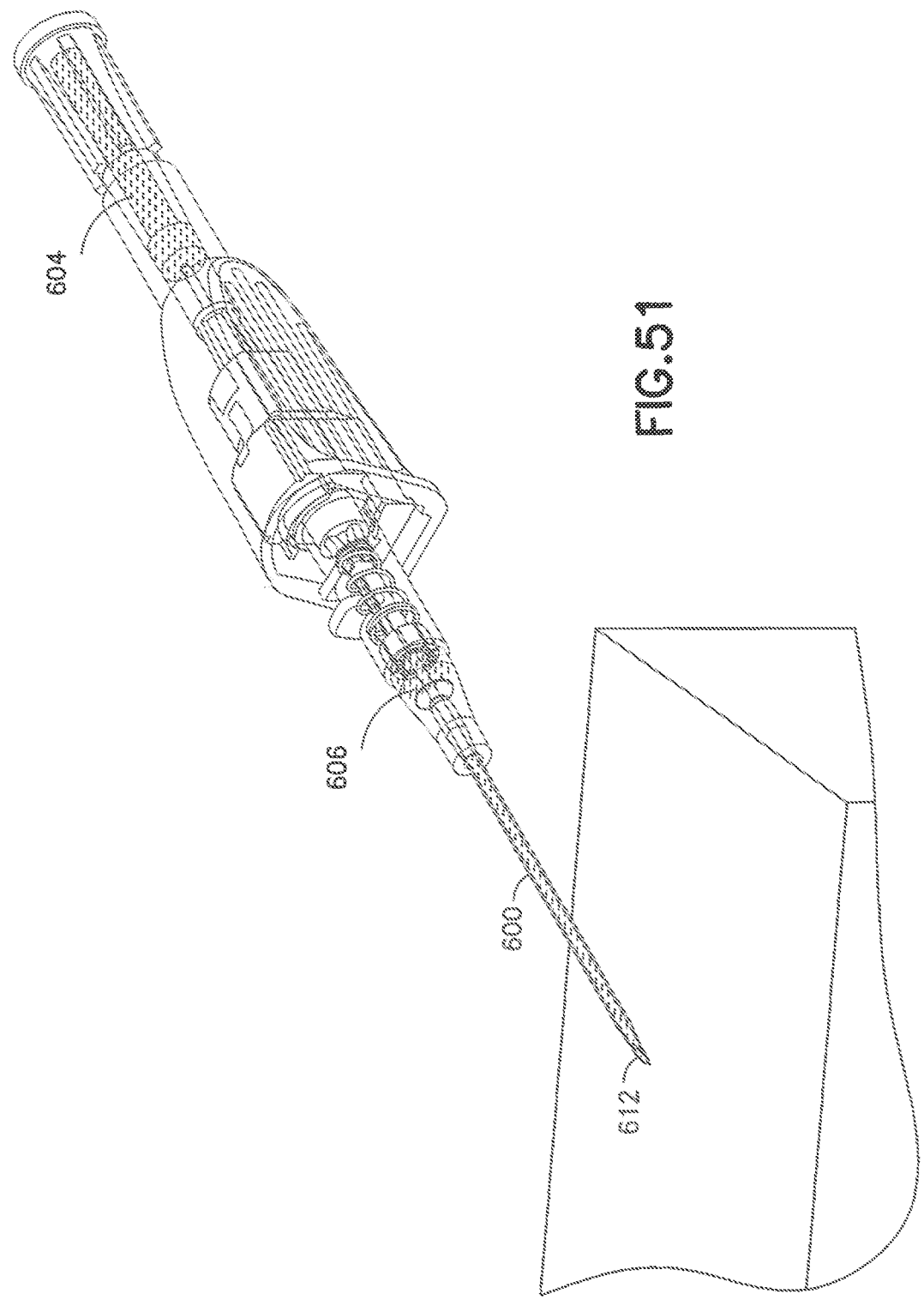
FIG. 51 illustrates another exemplary embodiment of a blood flashback feature of a catheter assembly.
Figure 52:
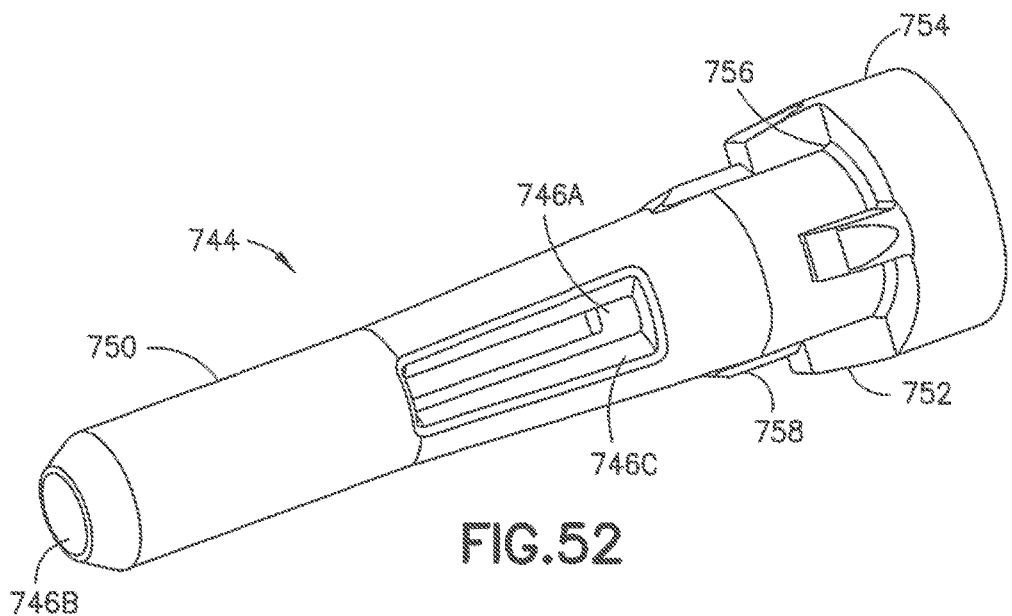
FIG. 52 illustrates a side perspective view of a valve actuator according to a further embodiment including a window in a diameter reduction region.
Figure 53:
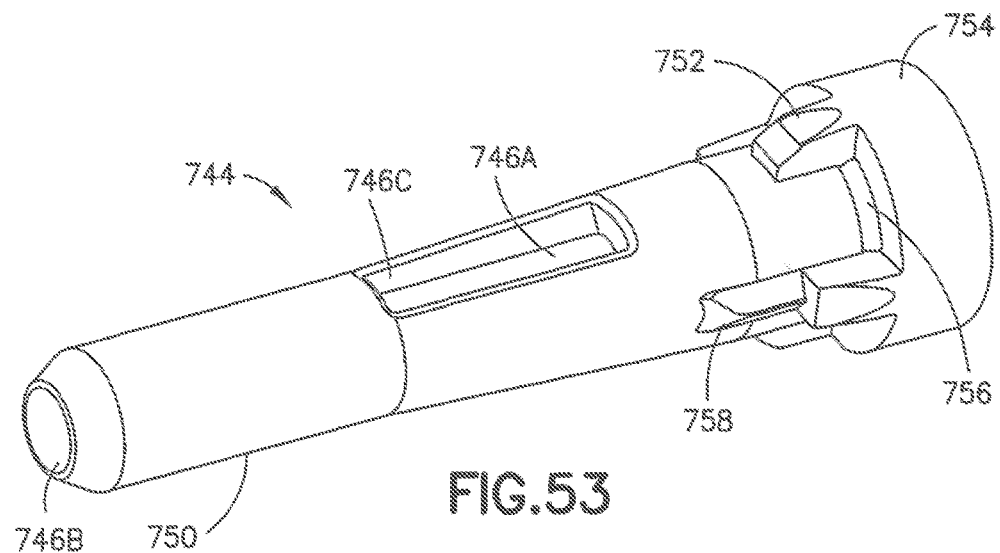
FIG. 53 illustrates a side perspective view of a valve actuator according to a still further embodiment including a window in a diameter reduction region.
Figure 55:
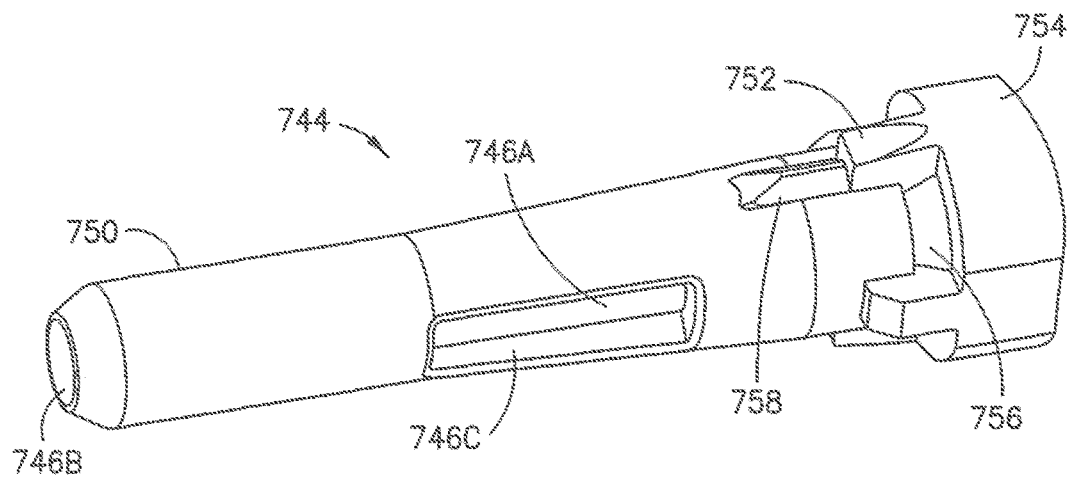
FIG. 55 illustrates a side perspective view of a valve actuator according to a still further embodiment including a window in a diameter reduction region.

FIGS. 49-51 illustrate various exemplary embodiments of blood flashback features in the catheter assembly. Flashback is the visibility of blood that confirms the entry of the needle tip into the vein. Primary flashback 600 is seen through the catheter tubing as blood travels into the open distal end of the hollow needle 612, out a notch or opening 602 in the needle 612 near the needle tip, and up through the internal annular space between the needle 612 and the inside of the catheter tubing. The secondary flashback 604 is seen in the needle hub/grip when it comes out of the back of the needle 612 and enters a flash chamber in the needle hub/grip. Air is vented by the plug in the back of the needle hub/grip by a porous membrane or micro grooves. Tertiary flashback 606 is visible in the catheter hub 614 when the blood from the primary flashback 600 flows into it and stops at the blood control septum Air is vented by the micro grooves in the periphery of the blood control septum. The features described in these embodiments, including the blood flashback features, can be used in combination with the features described throughout this application.

In another embodiment similar to the embodiment illustrated in FIGS. 3-8, the assembly 10 does not include a return member 56. Rather, as described earlier, the flaps defined by the slits 42 of the resilient septum 38 act as the return member 56. Prior to operation, the actuator 44 is in a free state and does not contact the septum 38 (first position of the actuator 44). In operation, the septum 38 is in an opened state where the actuator 44 (second position of the actuator 44) contacts or pushes against the slits 42 of the septum 38. The opened state of the septum 38 permits fluid communication. In the opened state of the septum 38, the actuator 44 does not extend through the septum 38. In other words, the actuator 44 does not penetrate the septum 38. As a result, the resilient flaps defined by the open slits 42 of the septum 38 cause the actuator 44 to retract to the first position when operation is complete and upon removal of the axial pressure on the actuator 44.

In another embodiment, as illustrated in FIGS. 52-55, the valve actuators 744 function in a similar manner to the valve actuators of the catheter assembly as described in the embodiments of FIG. 3-8. However, for the reasons described below, the valve actuators 744 of the following embodiments improve the flushing capability of the catheter assembly during a saline flush.

Similar to the embodiment of FIGS. 3-8, the valve actuators 744 include a shaft portion 750, a diameter reduction region 752 and a mating portion 754. The valve actuators 744 may be approximately 0.529 inches in length. The shaft portion 750 is configured to penetrate a septum of a catheter assembly. Specifically, the shaft portion 750 includes a distal opening 746b that provides an entrance into a hollow internal passage 746a that extends through a length of the valve actuator 744. When the valve actuator 744 penetrates the septum, fluid, such as blood or saline, travels through the hollow internal passage 746a. The valve actuator 744 also includes a plurality of openings 746c that provide a passageway for the fluid to exit the hollow internal passage 746a.

The mating portion 754 is disposed at a distal end of the valve actuator 744. An outer diameter of the mating portion 754 may be approximately 0.138 inches. The outer diameter of the mating portion 754 is larger than an outer diameter of the shaft portion 750 so that the mating portion 754 can engage and disengage with a Luer connector.

Figure 56:
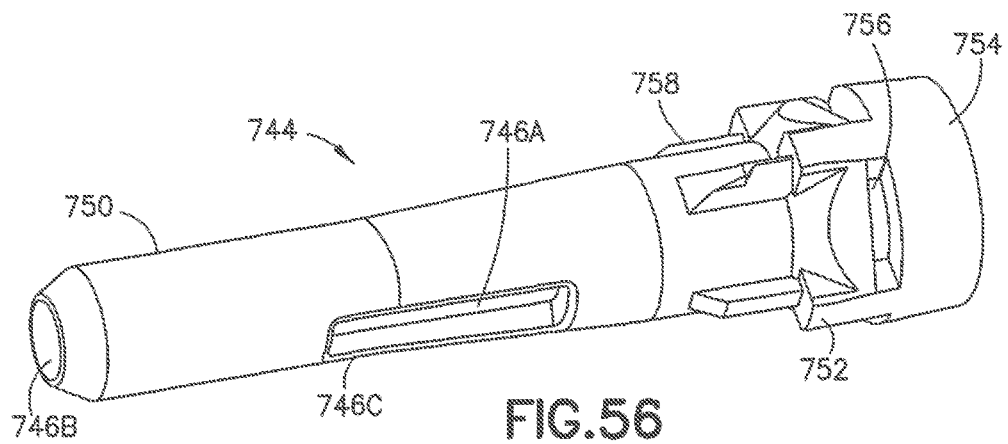
FIG. 56 illustrates a side perspective view of a valve actuator according to a still further embodiment including a window outside the diameter reduction region.
Figure 57:
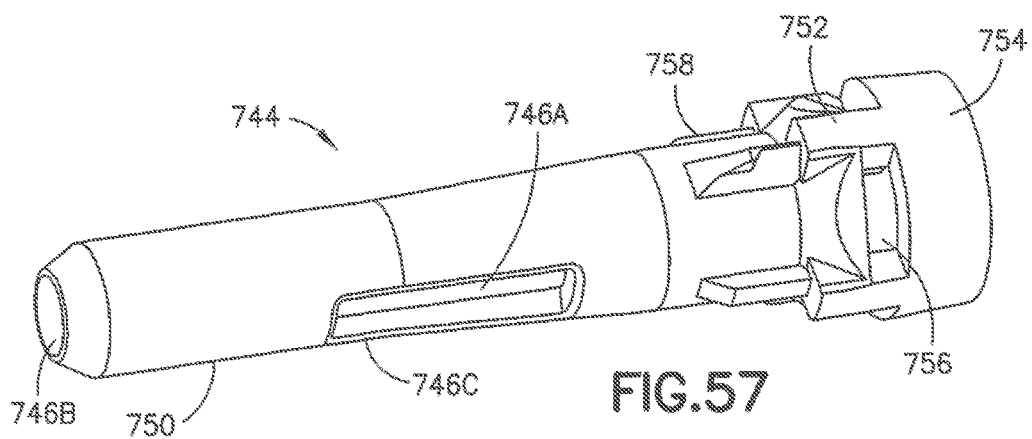
FIG. 57 illustrates a side perspective view of a valve actuator according to a still further embodiment including a window outside the diameter reduction region.
Figure 58:
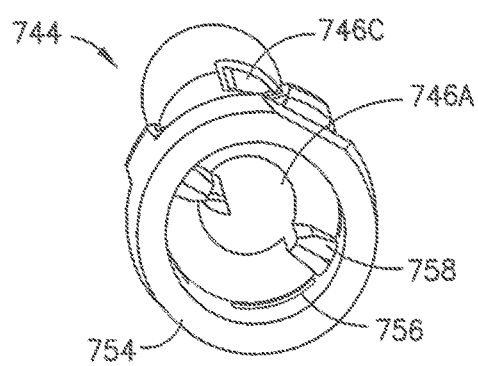
FIG. 58 illustrates a rear perspective view of the valve actuator in the embodiment of FIG. 57.

The diameter reduction region 752 is an inclined member disposed near a proximal end of an inner diameter of the valve actuator 744. The diameter reduction region 752 is disposed between the shaft portion 750 and the mating portion 754 to connect the shaft portion 750 and mating portion 754 and to provide a continuous outer surface of the valve actuator 744. The diameter reduction region 752 includes a plurality of protrusions 758 on an outer diameter as illustrated in FIGS. 52-57, as well as on an inner diameter as illustrated in FIG. 58. The protrusions 758 advantageously aid in assembling a spring and securing the spring in the catheter assembly during operation.

The diameter reduction region 752 further includes a plurality of windows 756. As illustrated in FIGS. 3-8, the windows can extend the full length of the diameter reduction region of the valve actuator. In a valve actuator 744 having a length of approximately 0.529 inches and a maximum outside diameter of approximately 0.138 inches, the full length (or height) of the diameter reduction region of FIGS. 3-8 can be 0.035-0.040 inches, for example. However, in FIGS. 52-55 the windows 756 extend only a portion of the diameter reduction region 752.

Specifically, FIGS. 52-55 illustrate that for an actuator of the overall size mentioned, the windows 756 can extend approximately 0.005 inches, 0.010 inches, 0.015 inches and 0.020 inches from a distal end of the diameter reduction region 752, respectively. Other embodiments include windows 756 at any length less than the full length of the diameter reduction region 752. Alternately, the windows 756 can extend approximately ½ or ⅓ of the length of the diameter reduction region 752. FIGS. 56 and 57 illustrate windows 756 adjacent to a distal end of the diameter reduction region 752 but outside the diameter reduction region 752. The windows 756 of FIGS. 56 and 57 are in the mating portion 754 of the valve actuator 756. The windows 756 of FIGS. 56 and 57 can extend at a length of approximately 0.010 inches and 0.020 inches, respectively, Advantages of the windows 756 are provided below.

During use, the valve actuator 756 is typically flushed with saline, for example, to remove any remaining blood or fluid. However, blood or fluid deposits can remain even after the saline flush. The windows 756 are reduced in size and placed at a proximal end of the diameter reduction region 752 to advantageously improve saline flushing.

Figure 54:
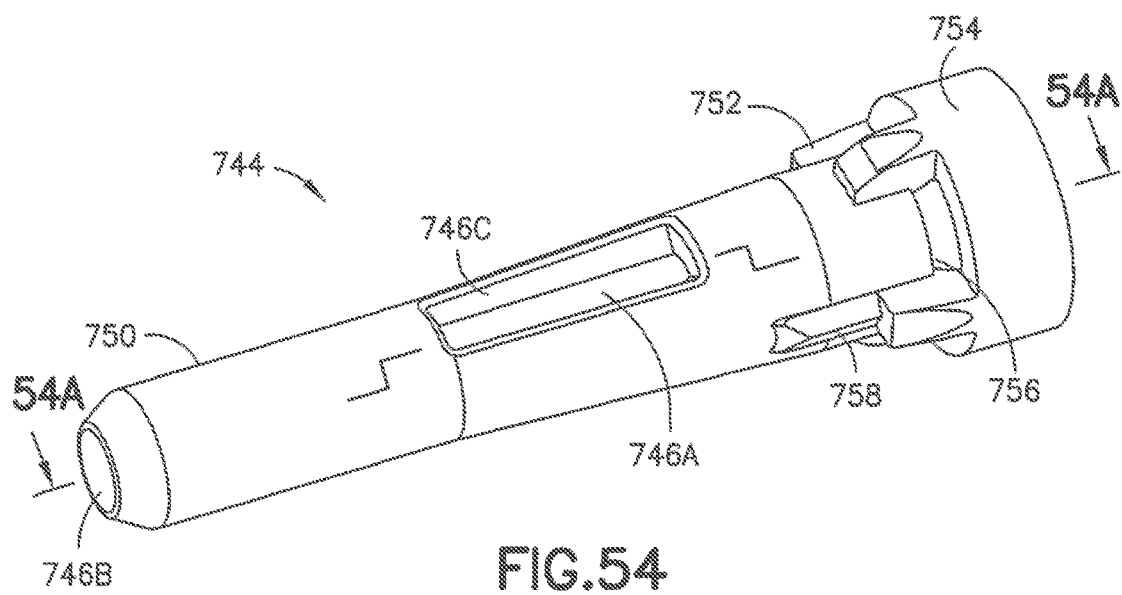
FIG. 54 illustrates a side perspective view of a valve actuator according to a still further embodiment including a window in a diameter reduction region.
Figure 54A:
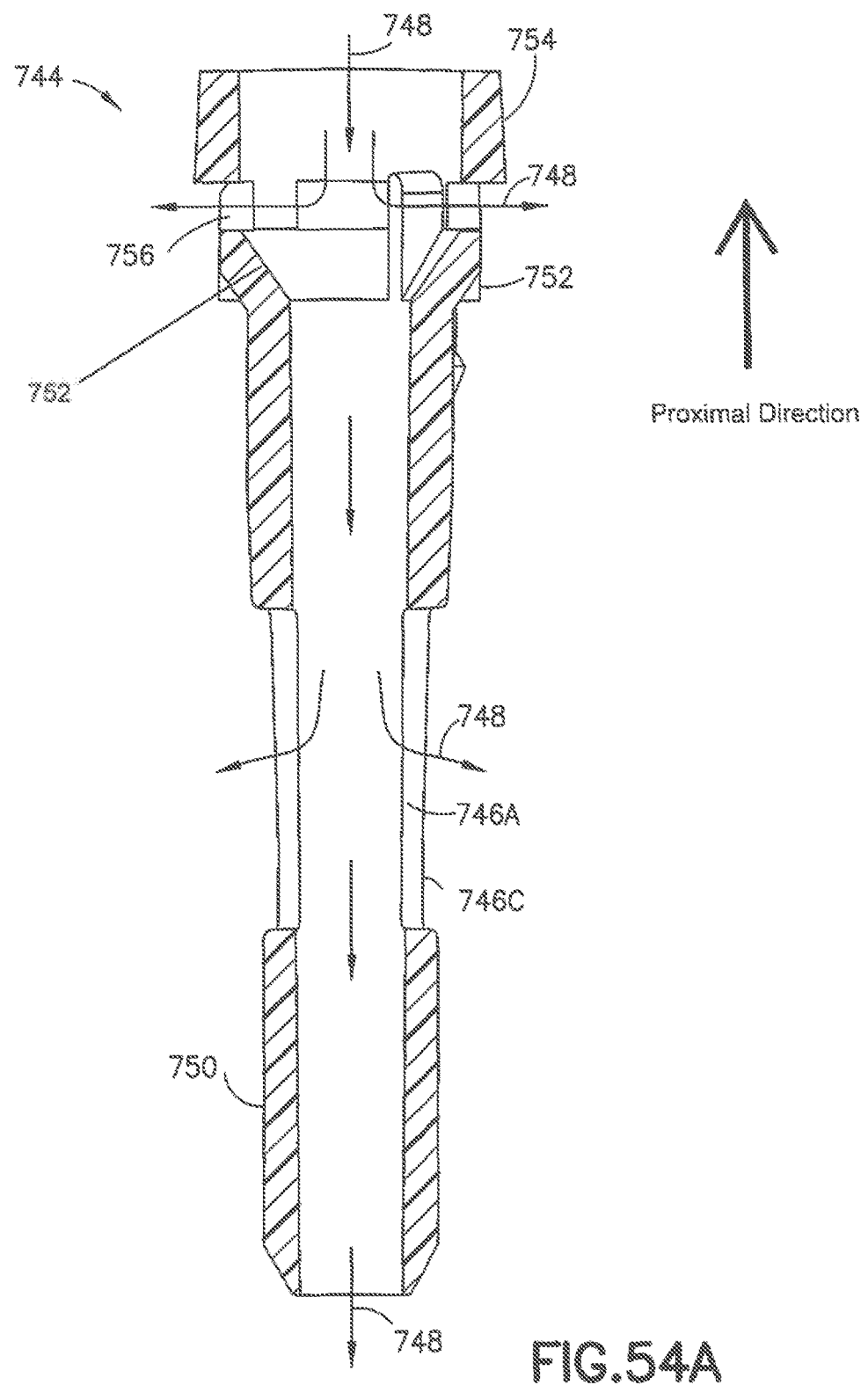
FIG. 54A illustrates a cross sectional view of the valve actuator in the embodiment of FIG. 54.

Specifically, the size (length or height) of the windows 756 increases the velocity of the saline flow. The saline flow 748 of FIG. 54A is representative of each of the windows 756 of FIGS. 52-55. As illustrated in FIG. 54A, the fluid flushing velocity of the saline flows almost entirely in a radial direction when exiting the windows 756. This is because the size of the windows 756 is smaller than the windows of the valve actuators in FIGS. 3-8. The size of the windows 756 causes the fluid that is traveling through the internal passage 746a in a longitudinal direction (axial direction) to shift into a perpendicular direction (radial direction) to exit the valve actuator 744. For an actuator of the overall size mentioned, the preferred optimal size (length or height) is approximately 0.0125±0.005 inches. The closer the size of the windows 756 to the preferred size, the more radial the direction of flow of fluid will exit out of the windows 756. The radial flow at a higher velocity will optimize flushing performance.

When compared to the embodiments of FIGS. 52-58, the flushing fluid velocity traveling through the windows of the valve actuators in FIGS. 3-8 has a higher axial component and travels at a lower velocity because of the large window size. As a result, a small section of reduced flushing can remain near a corner between the inner diameter of the adapter and the proximal end of the flushing window.

The placement of the windows 756 at the distal end of the diameter reduction region 752 improves the speed and direction of flow. The windows 756 outside the diameter reduction portion 752 cause the flow of fluid in the internal passage 746a to change direction more abruptly compared to the windows in the valve actuators of FIGS. 3-8. This is because the fluid flowing through the internal passage 746a travels shorter by the time the flow reaches the windows 756. Thus, the windows 756 outside the proximal end of the diameter reduction portion 750 forces flow to change into more of a radial direction when exiting the windows 756.

The fluid traveling through the windows 756 in the diameter reduction region 752 responds similarly. In these embodiments, the distance of the windows 756 from the centerline of the valve actuator 744 is variable between the distal end and the proximal end of the diameter reduction region 752. This variable flow travel length slightly alters the flushing performance of the windows 756. As described above, for an actuator of the overall size mentioned, the optimal window size (length or height) is approximately 0.0125±0.005 inches. The combination of the radial flow direction and the increased velocity advantageously enhances flushing.

FIGS. 59 and 60 are graphical illustrations of the improved flushing performance of the valve actuator. FIG. 59 represents the valve actuator with the windows of FIGS. 3-8 and FIG. 60 represents the valve actuator with the windows 756 of FIG. 53. The hash lines identified by a number represent the amount of blood remaining in the catheter hub after a saline flush. The remaining blood is measured by a ratio of blood mass to 3 milliliters of saline where 760 has a ratio of 1.0, 762 has a ratio of 0.9, 764 has a ratio of 0.8, 766 has a ratio of 0.7 and 764 has a ratio 0. As indicated in the window section of FIGS. 59 and 60, the amount of blood remaining in the reduced window design of FIG. 60 is significantly less than the amount of blood remaining in the normal window design of FIG. 59.

Figure 61:
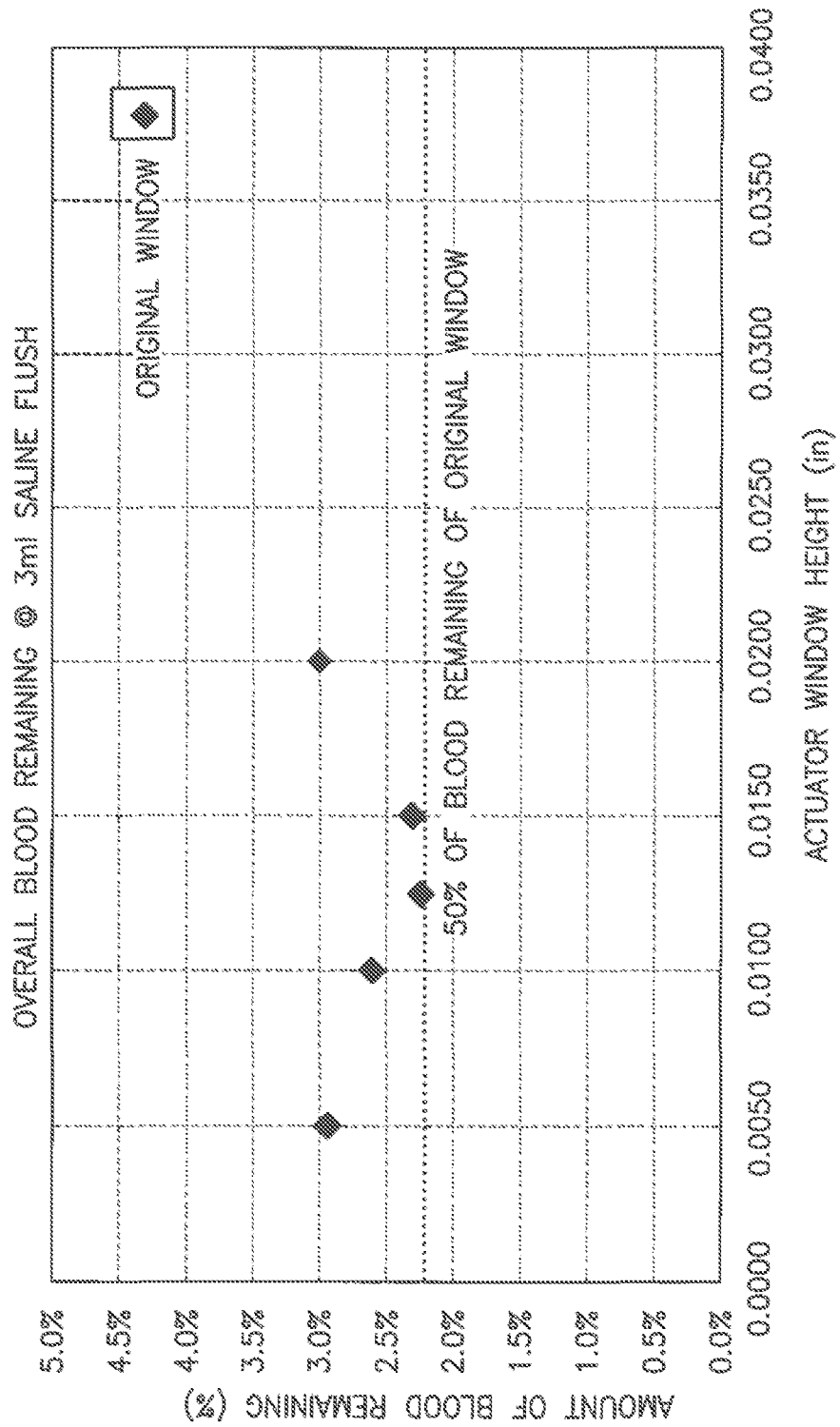
FIG. 61 illustrate a graphical comparison of the amount of blood remaining in the catheter hub with the valve actuators in the embodiments of FIGS. 3 and 53 after a saline flush.
Figure 62:
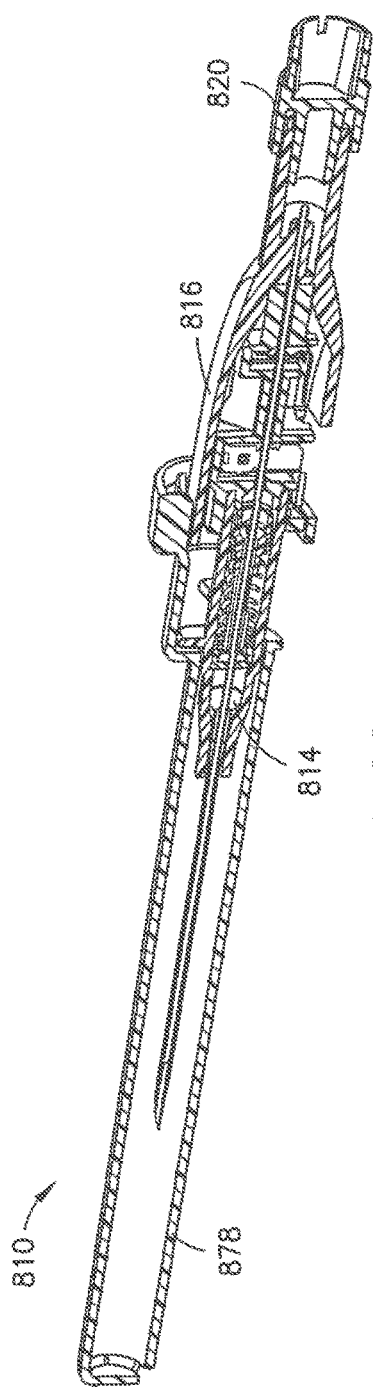
FIG. 62 illustrates a left perspective cross-sectional view of an alternate embodiment of the catheter assembly.

FIG. 61 shows another illustration of the amount of blood remaining after a 3 milliliter saline flush. Data points show the amount of blood remaining after a saline flush in the various sizes of the windows 756 in the valve actuators 744 of FIGS. 52-55 and in the window of the valve actuator of FIGS. 3-8. Specifically, the amount of blood remaining is approximately 2.2% with the 0.0125 inch window height. The amount of blood remaining is approximately 4.3% with the 0.0375 inch window height of FIGS. 3-8. Thus, as illustrated, the fluid flushing performance is approximately 50% improved when the window is approximately 0.0125 inches when compared to the windows in the valve actuators of FIGS. 3-8.

FIGS. 62-65 illustrate an alternate embodiment of the catheter assembly 810 with various components that function in a similar manner to the embodiments described above. In particular, a needle hub 816 operates in a similar manner as the embodiment of FIGS. 46-48. The catheter hub 814 operates in a similar manner as the embodiment of FIGS. 4-8 except for the differences detailed below.

The needle and catheter tubing of the catheter assembly 810 are enclosed by a needle cover 878 when not in use. The needle cover 878 is removed to begin operation of the catheter assembly 810. The catheter assembly 810 also includes a flow control plug 820 that is similarly described in FIG. 51. Specifically, the plug 820 includes a porous membrane or micro grooves being disposed at a proximal end of the needle hub 816 to vent air while containing blood.

Figure 63:
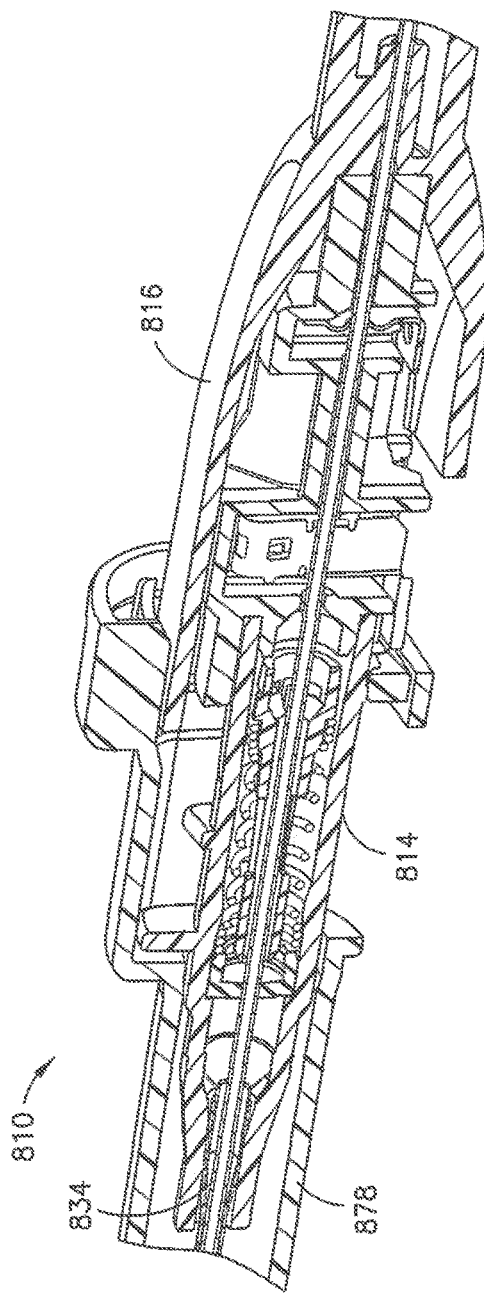
FIG. 63 illustrates a left perspective cross-sectional view of the catheter hub and the needle hub in the embodiment of FIG. 62.

FIG. 63 illustrates the catheter hub 814 and the needle hub 816 of the catheter assembly 810. Specifically, the catheter hub 814 includes a metal wedge 834 made of, for example, 302, 304 or 305 stainless steel in an annealed state. Alternately, the metal wedge 834 can be 302 or 304 stainless steel in the annealed or close to annealed state. 302 and 304 stainless steels have a very low magnetic susceptibility in the annealed state, which is advantageous when the catheter assembly is left in place on a patient during a magnetic resonance imaging (MRI) procedure.

Figure 64:
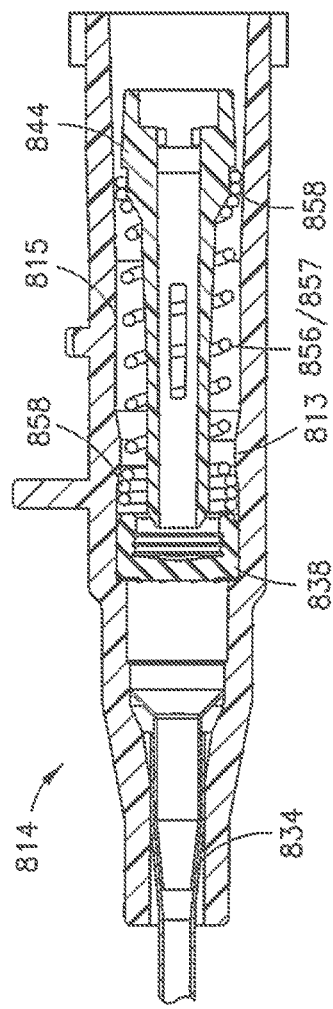
FIG. 64 illustrates a cross-sectional view of the catheter hub in the embodiment of FIG. 62.
Figure 65:
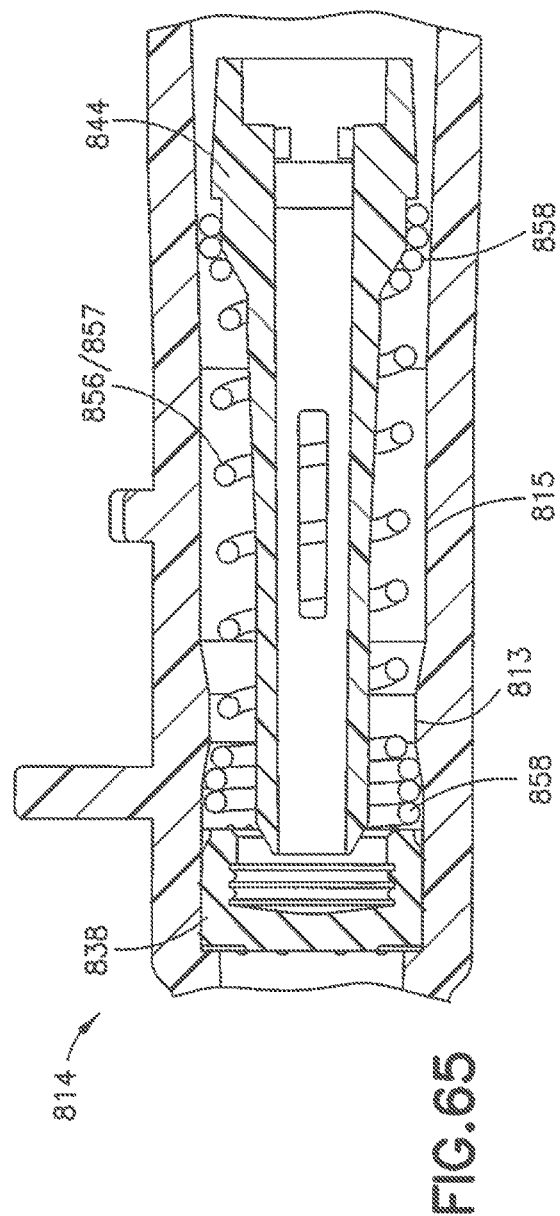
FIG. 65 illustrates a cross-sectional view of a valve actuator and a spring in the embodiment of FIG. 62.

FIG. 64 illustrates the catheter hub 814 and FIG. 65 illustrates a valve actuator 844 of the catheter hub 814 prior to operation. Specifically, the catheter hub 814 includes an inner diameter 815, as well as an undercut 813. The inner diameter 815 is larger than the undercut 813. The undercut 813 is used to secure a spring 856, as further described below.

The catheter hub 814 also includes a septum 838. The septum 838 is secured via an interference fit to the inner diameter 815 of the catheter hub 814 to ensure proper operation of the septum 838. The septum 838 contacts an inner wall of the catheter hub 814 for proper positioning. The septum 838 passes the undercut 813 when assembled from a proximal end of the catheter hub 814.

The valve actuator 844 is configured to penetrate the septum 838 during operation of the catheter assembly 810. The spring 856 is compressed when the valve actuator 844 penetrates the septum 838. Subsequently, the spring 856 retracts the valve actuator 844 after piercing the septum 838. The spring 856 includes center coils 857 and two or more end coils 858. The end coils 858 have a greater outer diameter than the center coils 857.

Tests show that the material of the metal wedge 834 does not cause magnetic problems during MRI procedures, but this is not necessarily the case for the spring 856. Either 302 or 304 stainless steel is the conventional material used for springs because of its higher carbon content and ease of manufacturability. However, the catheter assembly including the spring composed of 302 or 304 stainless steel has very high magnetic properties when hardened to the level that a spring requires. Specifically, the metal of the spring must be cold worked to spring temper in order to have the higher shear strength, which consequentially makes the metal more magnetically susceptible.

Accordingly, springs composed of 302 or 304 stainless steel in the catheter assembly may not be compatible for use during magnetic resonance imaging (MRI) procedures. This is because the magnets of an MRI device can cause susceptible metals in the catheter assembly to pull, twist and heat up. As a result, a catheter assembly with springs composed of 302 or 304 stainless steel should be removed from the patient prior to MRI procedures.

316 stainless steel is not commonly used as a spring material because of its low strength, high cost and difficulty in processing. However, 316 stainless steel is the preferred material for the spring 856 and advantageously improves in strength as the temper of the material changes. In this embodiment, the temper of 316 stainless steel is increased to satisfy an ASTM F138-08 material strength standard for stainless steel surgical implant devices. Preferably, the strength requirement for the spring 856 exceeds what is specified in ASTM F138.

As the temper of 316 stainless steel increases, the magnetic attraction also increases. However, the magnetic properties of 316 stainless steel are less than 302 or 304 stainless steel because of the lower carbon content. Specifically, the composition of the 316 series stainless steel or their equivalents, especially the chromium and nickel content and the ratio of Cr/Ni content in these alloys, helps the austenite phase remain stable through the cold working process and resist transformation to martensite. The low carbon content of an 'L' grade 316 stainless steel also aids in alloy stability. Thus, when 316 stainless steel achieves spring temper, the spring 856 in the catheter assembly 810 is compatible for use during MRI procedures.

In particular, the spring 856 is advantageously made of 316 stainless steel that is cold worked to a spring temper. Other preferred materials of the spring 856 include 316L stainless steel, 316 LVM stainless steel (bare wire with no nickel coating having a 240 ksi minimum tensile strength), titanium, beryllium, copper, magnesium and magnesium alloys such as Elgiloy. Alternatively, or in addition, the spring 856 is plated with a diamagnetic material, such as palladium, to reach the desired magnetic permeability. The spring 856 can be magnetically susceptible but plated with a diamagnetic material to substantially cancel out the overall magnetism of the material. Thus, the diamagnetic material can help achieve a zero net attraction force of the metal.

These material and process selections allow the spring 856 in the catheter assembly 810 to achieve a magnetic relative permeability that is less than 2.0 and preferably less than 1.1. The magnetic relative permeability is a dimensionless value that is commonly understood by one of ordinary skill in the art. The material and associated processing selection for the spring 856 advantageously allows the catheter assembly 810 to remain attached to the patient during MRI procedures. In other words, the correct alloys and tempers of metals are used in the catheter assembly 810 to keep magnetic susceptibility low enough so that there is no compatibility concern with the catheter assembly 810 during MRI procedures.

During assembly, one of the end coils 858 of the spring 856 travels past the undercut 813 and is snapped into place. Specifically, the end coil 858 is movably captured between the septum 838 and the undercut 813. The end coils 858 of the spring 856 advantageously do not have to be disposed at a precise location. The outer diameter of the end coils 858 is greater than the diameter of the undercut 813 to movably retain the spring 856. Thus, the spring 856 and catheter hub 814 advantageously prevent the inadvertent removal of the valve actuator 844. Also, the improved assembly advantageously causes less variation to the function of the catheter assembly 810.

An outer diameter of the center coils 857 is smaller than the diameter of the undercut 813. This advantageously prevents interference and allows the spring 856 to move axially in the catheter hub 814 by a limited amount, until a Luer connector is attached.

A clearance fit is present between the inner diameter 815 of the catheter hub 814 and the outer diameter of the end coils 858 of the spring 856. A clearance fit advantageously facilitates assembly and operation of the spring 856. Specifically, once the end coils 858 pass the undercut 813 during assembly, the spring 856 is properly located. The other end coil 858 is immovably fixed to the valve actuator 844. Thus, the spring 856 and the valve actuator 844 can axially move "or float" (within limits) inside the catheter hub 814 when no Luer connector is present. The actuator does not contact the inner diameter 815 of the catheter hub 814.

When an interference fit is present between the spring and the inner diameter of the catheter hub as described in the embodiment of FIGS. 3-8, it can be difficult to place the spring in the correct position. Specifically, it can be difficult to set the exact position of the spring because of the length of the inner diameter in the catheter hub. Also, the shoulder that the septum rests on is deep inside the length of the inner diameter of the catheter hub.

Moreover, an interference fit requires very tight tolerances on the outer diameter of the spring, as well as the inner diameter of the catheter hub. If the interference fit is too severe, the life of the spring may be compromised. If the interface between the spring and the inner diameter of the catheter hub becomes loose, then the spring and the valve actuator may be inadvertently removed.

The interference fit can also present problems in operation because the septum may move with the spring during retraction. This is because the interference fit between the spring and the inner diameter of the catheter hub may create a jam where the septum moves with the spring. The high forces in an interference fit can overcome the frictional forces of the septum and cause the septum to move with the spring. Additionally, the interference fit can cause undue pressure on the valve actuator 844 during retraction. Also, if the spring 856 is compressed too far distally such that the septum 838 is compressed, an interference fit may not allow the septum 838 to retract or relax. As a result, the septum 838 may leak over time due to the excessive and continuous compression.

On the other hand, when a clearance fit is present between the spring 856 and the inner diameter 815 of the catheter hub 814, the spring 856 can move axially when no Luer connector is present and can apply pressure to a proximal face of the septum 838 only when a Luer connector is inserted. Thus, the combination of the clearance fit and the undercut 813 advantageously improves the operation, the ability to position the spring 856, and the manufacturability of the catheter assembly.

Figure 66:
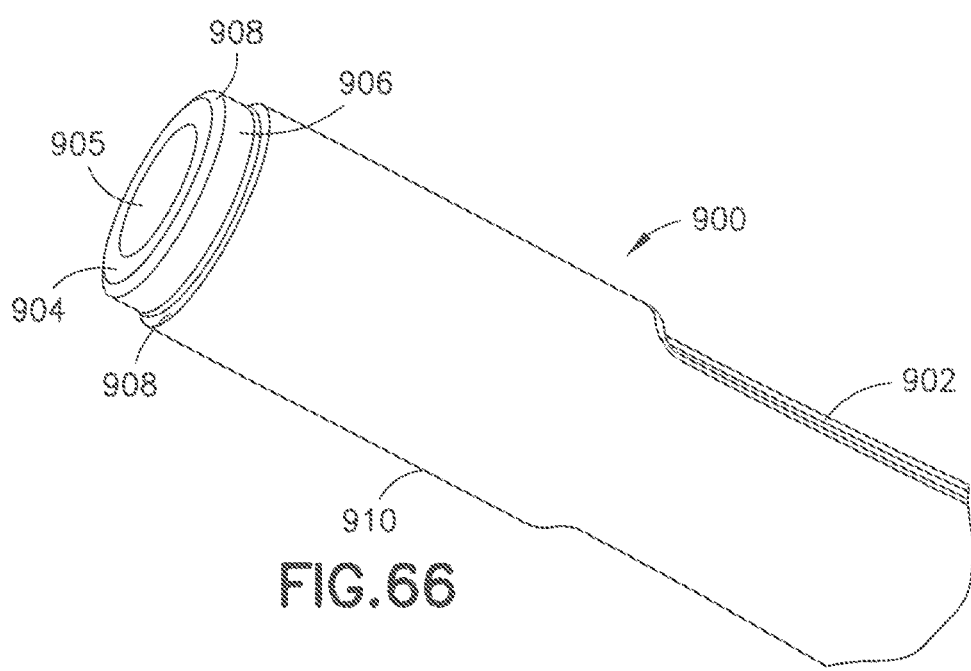
FIG. 66 illustrates a perspective view of another embodiment of the valve actuator.
Figure 67:
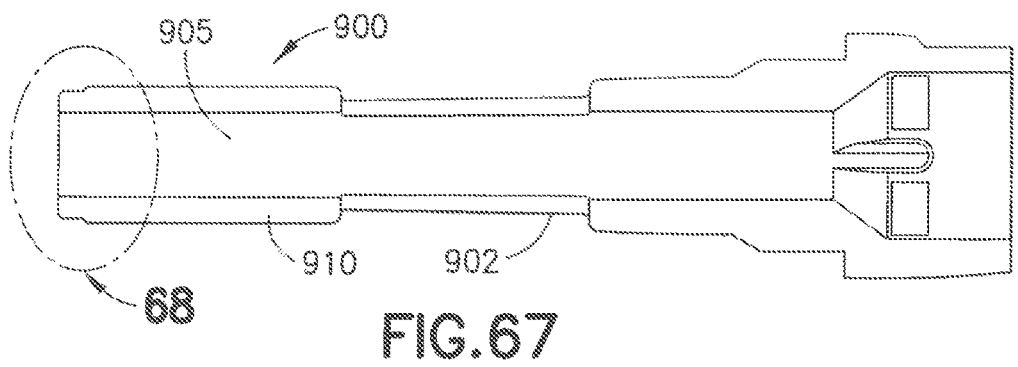
FIG. 67 illustrates a cross-sectional view of the valve actuator of FIG. 66.
Figure 68:
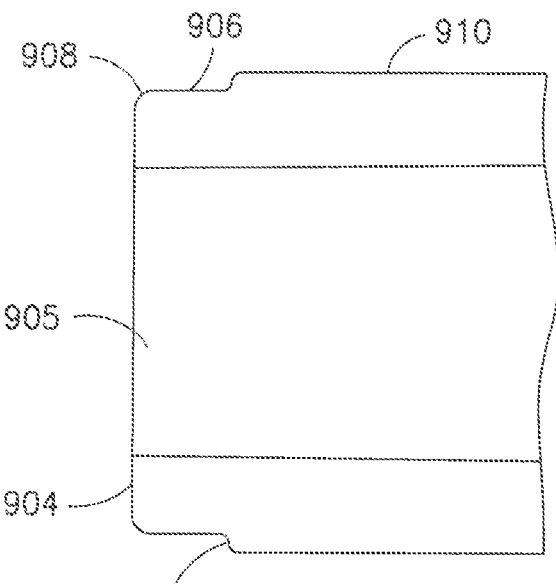
FIG. 68 illustrates an enlarged view of a distal end of the valve actuator of FIG. 67.

According to another embodiment, as illustrated in FIGS. 66-68, a valve actuator 900 with a single-stepped distal tip includes a side opening 902, a distal end 904, a distal end opening 905, a step 906, radii 908, and an outer diameter 910. The openings 902, 905 provide for fluid flushing and flow through the valve actuator 900 when engaged to a septum in a catheter hub. The openings 902, 905 operate in a similar manner described above in previous embodiments.

The step 906 is disposed between the distal end 904 and the outer diameter 910 of the valve actuator 900. Since the valve actuator 900 is injection molded, no sharp edges are formed on its outer surface. Instead, radii 908 are disposed on either end surface of the step 906. Specifically, a radius 908 is disposed at the interface of the step 906 and the distal end 904, as well as at the interface between the step 906 and the outer diameter 910. The step 906 at the distal end 904 of the valve actuator 900 replaces the taper at the distal end of the valve actuators of previous embodiments. The radii 908 advantageously allow for ease of manufacturability during injection molding.

Figure 69:
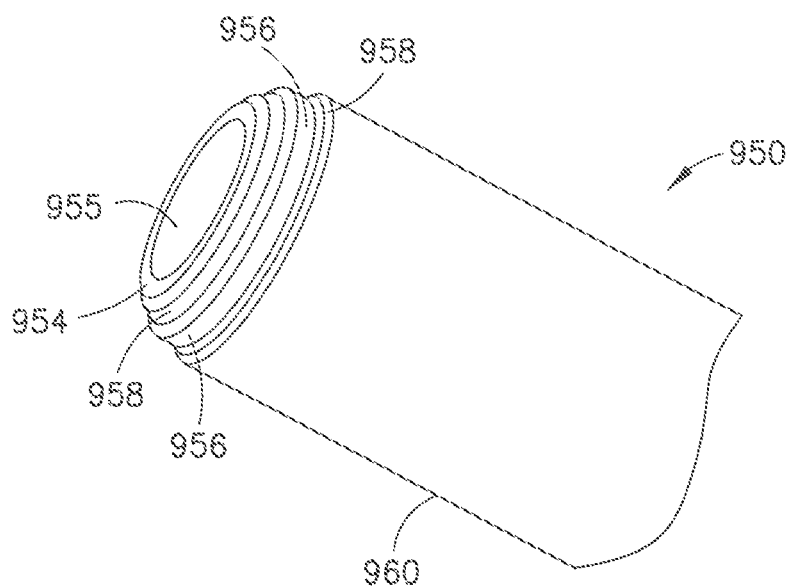
FIG. 69 illustrates a perspective view of another embodiment of the valve actuator.
Figure 70:
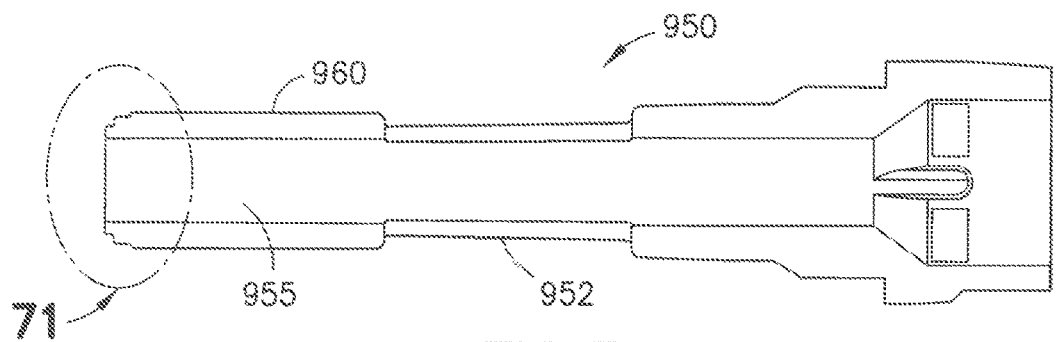
FIG. 70 illustrates a cross-sectional view of the valve actuator of FIG. 69.
Figure 71:
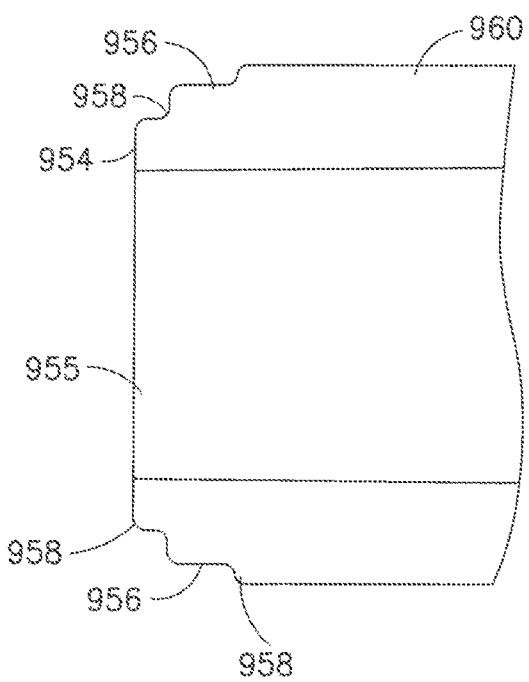
FIG. 71 illustrates an enlarged view of a distal end of the valve actuator of FIG. 70.

FIGS. 69-71 illustrate a valve actuator 950 with a double-stepped distal tip according to another embodiment. In this embodiment, the valve actuator 950 includes an opening 952, a distal end 954, a distal end opening 955, radii 958, and an outer diameter 960 in a similar manner as described in the embodiment of FIGS. 66-68. However, the valve actuator 950 has two steps 956 between the outer diameter 960 and the distal end 954. The two steps 956 have two different diameters with appropriate radii 95$ on each end surface. Likewise, the radii 908 advantageously allow for ease of manufacturability during injection molding.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. A valve actuator that moves in a catheter assembly between a first position where a valve is closed and a second position where the valve is open, the valve actuator comprising:
   a shaft portion at a distal end of the valve actuator that is configured to open the valve;
   a mating portion at a proximal end of the valve actuator that is configured to engage a Luer device;
   a diameter reduction region that connects the shaft portion and the mating portion; and
   a plurality of windows that extend through the valve actuator for flushing fluid, the plurality of windows being disposed in the diameter reduction region, wherein
   each of the plurality of windows does not extend a full length of the diameter reduction region; and
   each of the plurality of windows is elongated in a circumferential direction.

2. A valve actuator that moves in a catheter assembly between a first position where a valve is closed and a second position where the valve is open, the valve actuator comprising:
   a shaft portion at a distal end of the valve actuator that is configured to open the valve;
   a mating portion at a proximal end of the valve actuator that is configured to engage a Luer device;
   a diameter reduction region that connects the shaft portion and the mating portion; and
   a plurality of windows that extend through the valve actuator for flushing fluid, the plurality of windows being disposed in the diameter reduction region, wherein
   each of the plurality of windows does not extend a full length of the diameter reduction region; and
   the plurality of windows extends to a length of approximately half of the length of the diameter reduction region from a proximal end of the diameter reduction region.

3. A valve actuator that moves in a catheter assembly between a first position where a valve is closed and a second position where the valve is open, the valve actuator comprising:
   a shaft portion at a distal end of the valve actuator that is configured to open the valve;
   a mating portion at a proximal end of the valve actuator that is configured to engage a Luer device;
   a diameter reduction region that connects the shaft portion and the mating portion; and
   a plurality of windows that extend through the valve actuator for flushing fluid, the plurality of windows being disposed in the diameter reduction region, wherein
   each of the plurality of windows does not extend a full length of the diameter reduction region; and
   the plurality of windows extends to a length of approximately a third of the length of the diameter reduction region from a proximal end of the diameter reduction region.

4. A valve actuator that moves in a catheter assembly between a first position where a valve is closed and a second position where the valve is open, the valve actuator comprising:
   a shaft portion at a distal end of the valve actuator that is configured to open the valve;
   a mating portion at a proximal end of the valve actuator that is configured to engage a Luer device;
   a diameter reduction region that connects the shaft portion and the mating portion; and
   a plurality of windows that extend through the valve actuator for flushing fluid, the plurality of windows being disposed in the diameter reduction region, wherein
   each of the plurality of windows does not extend a full length of the diameter reduction region; and
   the plurality of windows extends to a length of approximately 0.0125 inches.

5. The valve actuator of claim 1, further comprising one or more openings that extends through the valve actuator, wherein
   the one or more openings is disposed in the shaft portion.

6. A valve actuator that moves in a catheter assembly between a first position where a valve is closed and a second position where the valve is open, the valve actuator comprising:
 a shaft portion at a distal end of the valve actuator that is configured to open the valve;
 a mating portion at a proximal end of the valve actuator that is configured to engage a Luer device;
 a diameter reduction region that connects the shaft portion and the mating portion; and
 a plurality of windows that extends through the valve actuator for flushing fluid, wherein
 the plurality of windows is disposed outside the diameter reduction region; and
 each of the plurality of windows is elongated in a circumferential direction.

7. The valve actuator of claim 6, wherein the plurality of windows is adjacent to a proximal end of the diameter reduction region.

8. A valve actuator that moves in a catheter assembly between a first position where a valve is closed and a second position where the valve is open, the valve actuator comprising:
 a shaft portion at a distal end of the valve actuator that is configured to open the valve;
 a mating portion at a proximal end of the valve actuator that is configured to engage a Luer device;
 a diameter reduction region that connects the shaft portion and the mating portion; and
 a plurality of windows that extends through the valve actuator for flushing fluid, wherein
 the plurality of windows is disposed outside the diameter reduction region; and
 the plurality of windows extends to a length of approximately 0.0125 inches.

9. The valve actuator of claim 6, wherein
 the valve actuator further includes one or more openings that extends through the valve actuator, and
 the openings are disposed in the shaft portion.

10. A catheter assembly comprising:
 a catheter;
 a needle having a sharp distal tip disposed within the catheter;
 a catheter hub connected to the catheter having the needle passing therethrough, the catheter hub including:
  a valve that selectively permits or blocks a flow of fluid through the catheter;
  a valve actuator that moves between a first position and a second position; and
  a return member that returns the valve actuator from the second position to the first position; and
  a needle protection member that encloses the sharp distal tip of the needle, wherein
 the valve actuator includes a diameter reduction region having a plurality of windows, and
 each of the plurality of windows does not extend a full length of the diameter reduction region.

11. A catheter assembly comprising:
 a catheter;
 a needle having a sharp distal tip disposed within the catheter;
 a catheter hub connected to the catheter having the needle passing therethrough, the catheter hub including:
  a valve that selectively permits or blocks a flow of fluid through the catheter;
  a valve actuator that moves between a first position and a second position;
  a return member that returns the valve actuator from the second position to the first position; and
  a needle protection member that encloses the sharp distal tip of the needle, wherein
 the valve actuator including
  a diameter reduction region, and
  a plurality of windows that extends through the valve actuator for flushing fluid,
 the plurality of windows being disposed outside the diameter reduction region.

12. The valve actuator of claim 1, wherein
 the shaft portion at the distal end of the valve actuator includes a step;
 the step includes a first outer diameter adjacent to the distal end of the valve actuator and a second outer diameter proximal to the first outer diameter; and
 the second outer diameter is greater than the first outer diameter.

13. A valve assembly including a valve and a valve actuator that moves in a catheter assembly between a first position where the valve is closed and a second position where the valve is open, the valve actuator comprising:
 a shaft portion at a distal end of the valve actuator that is configured to open the valve; and
 a mating portion at a proximal end of the valve actuator that is configured to engage a Luer device;
 wherein the shaft portion at the distal end of the valve actuator includes a step;
 the step includes a first outer diameter adjacent to the distal end of the valve actuator and a second outer diameter proximal to the first outer diameter; and
 the second outer diameter is greater than the first outer diameter.

14. A valve actuator comprising:
 a shaft portion at a distal end of the valve actuator that is configured to open a valve; and
 a mating portion at a proximal end of the valve actuator that is configured to engage a Luer device;
 wherein the shaft portion at the distal end of the valve actuator includes a step;
 the step includes a first outer diameter adjacent to the distal end of the valve actuator and a second outer diameter proximal to the first outer diameter; and
 the second outer diameter is greater than the first outer diameter.

15. The valve actuator of claim 14, wherein the step includes a radius between the first and second outer diameters.

16. The valve actuator of claim 15, wherein the radius includes:
 a first radius disposed at an interface between the step and a distal surface of the valve actuator; and
 a second radius disposed at an interface between the step and the second outer diameter of the valve actuator.

17. The valve actuator of claim 14, wherein:
 the step includes a first step and a second step; and
 the first and second steps each includes a radius.

18. The valve actuator of claim 17, wherein the first and second steps are adjacent to each other.

19. The valve actuator of claim 17, wherein the first step is adjacent to a distal surface of the valve actuator.

* * * * *